(12) United States Patent
Ross et al.

(10) Patent No.: US 9,561,129 B2
(45) Date of Patent: Feb. 7, 2017

(54) TISSUE REMOVAL DEVICES, SYSTEMS AND METHODS

(76) Inventors: Rodney L. Ross, Mission Viejo, CA (US); James Dennewill, Laguna Hills, CA (US); Gregg Hughes, Mission Viejo, CA (US)

( * ) Notice: Subject to any disclaimer, the term of this patent is extended or adjusted under 35 U.S.C. 154(b) by 536 days.

(21) Appl. No.: 13/602,925

(22) Filed: Sep. 4, 2012

(65) Prior Publication Data
US 2013/0060210 A1 Mar. 7, 2013

Related U.S. Application Data

(63) Continuation-in-part of application No. 13/234,672, filed on Sep. 16, 2011, now abandoned, which is a continuation-in-part of application No. 12/683,893, filed on Jan. 7, 2010, now Pat. No. 9,370,611.

(60) Provisional application No. 61/143,010, filed on Jan. 7, 2009.

(51) Int. Cl.
*A61F 9/007* (2006.01)
*A61M 1/00* (2006.01)
*A61B 18/08* (2006.01)

(52) U.S. Cl.
CPC .......... *A61F 9/00736* (2013.01); *A61M 1/008* (2013.01); *A61M 1/0035* (2014.02); *A61M 1/0037* (2013.01); *A61B 18/082* (2013.01); *A61M 2205/3653* (2013.01); *A61M 2210/0612* (2013.01)

(58) Field of Classification Search
CPC A61B 18/082; A61F 9/00736; A61M 1/0035; A61M 1/0037; A61M 1/008; A61M 2205/3653; A61M 2210/0612
See application file for complete search history.

(56) References Cited

U.S. PATENT DOCUMENTS

2008/0319374 A1* 12/2008 Zacharias ........... A61M 1/0035
604/22

* cited by examiner

*Primary Examiner* — Imani Kayman

(57) ABSTRACT

A tissue removal device includes a rigid aspiration cannula, a valve communicating with the aspiration cannula in a fluid-sealed manner, and a pneumatically-driven actuator configured for moving the valve between an open position and a closed position, wherein at the open position the valve defines an aspiration path through the aspiration cannula and the valve, and at the closed position the valve prevents vacuum from being applied at the distal tip.

34 Claims, 37 Drawing Sheets

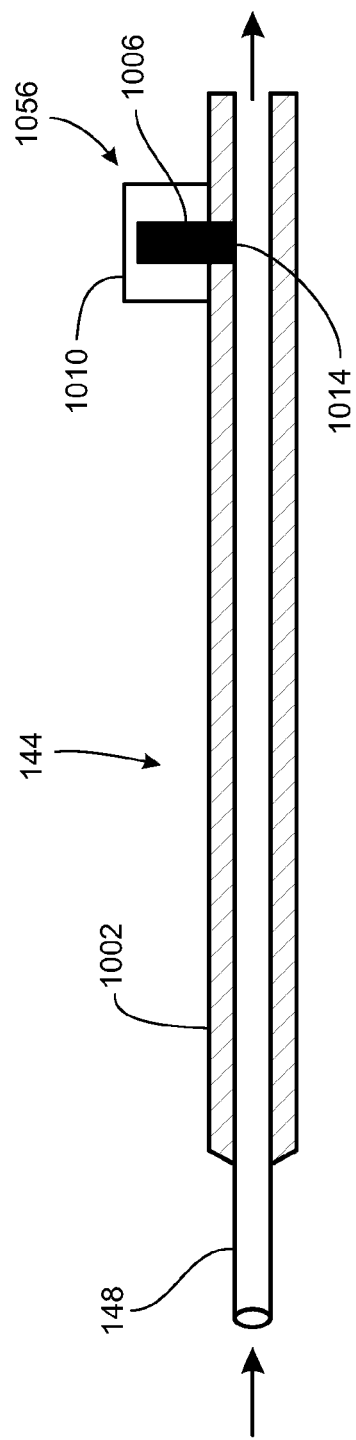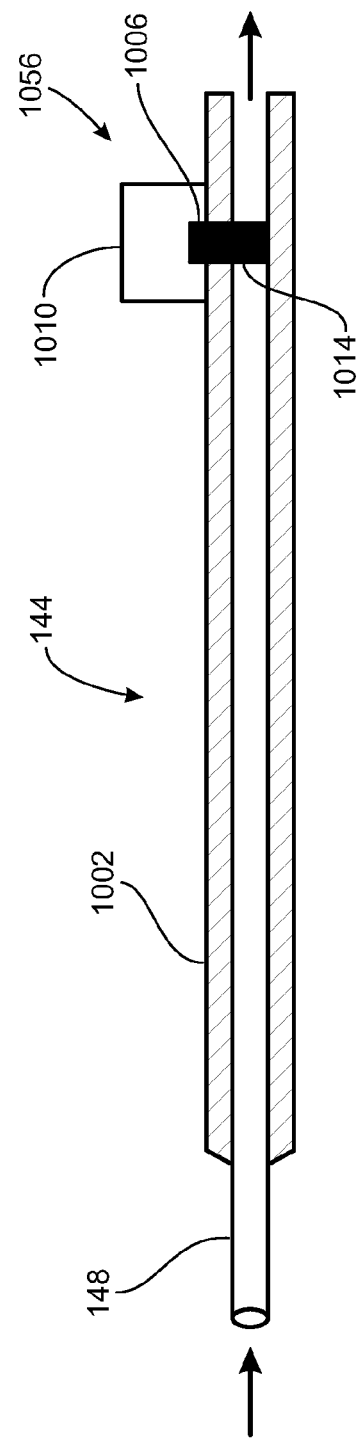

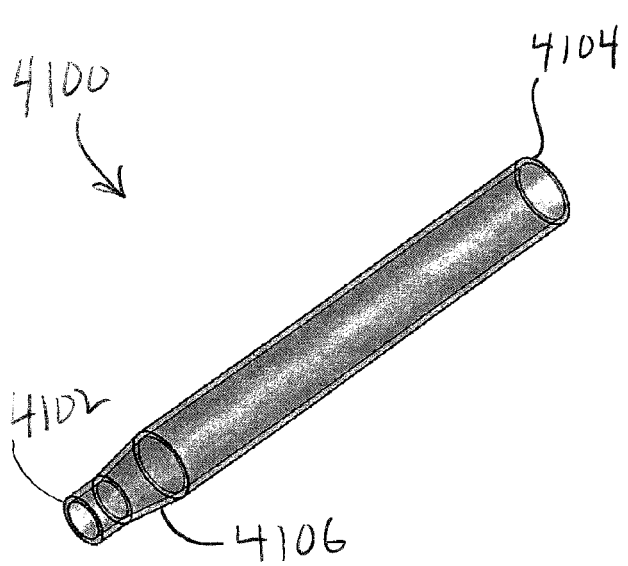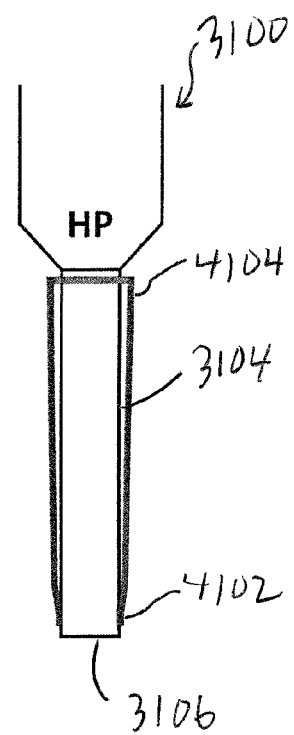
Fig. 41
Fig. 42

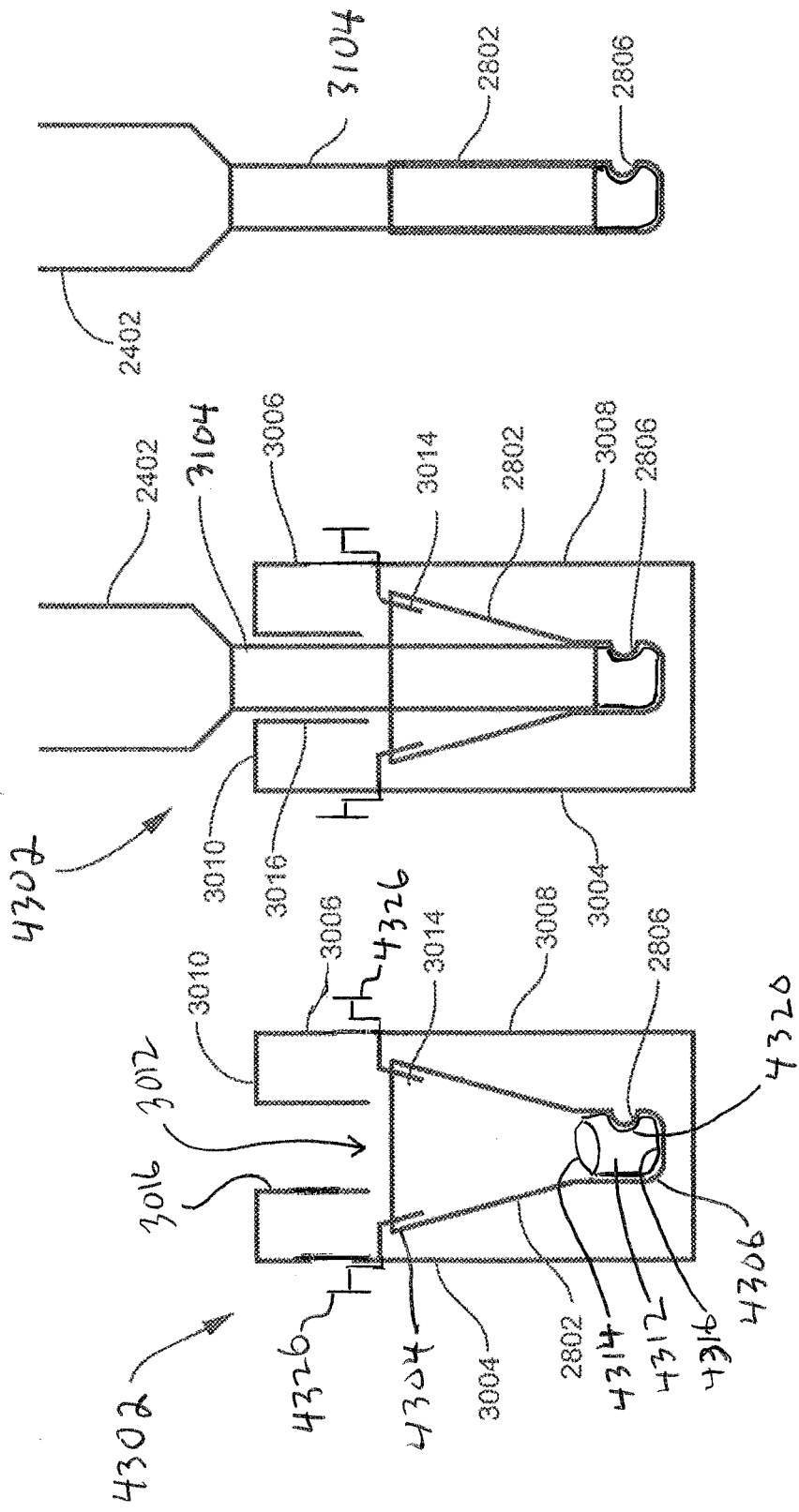

TISSUE REMOVAL DEVICES, SYSTEMS AND METHODS

RELATED APPLICATIONS

This application is a continuation-in-part of and claims priority to U.S. application Ser. No. 13/234,672, filed on Sep. 16, 2011, titled "TISSUE REMOVAL DEVICES, SYSTEMS AND METHODS"; which is a continuation-in-part of and claims priority to U.S. application Ser. No. 12/683,893, filed on Jan. 7, 2010 now U.S. Pat. No. 9,370,611, titled "TISSUE REMOVAL DEVICES, SYSTEMS AND METHODS"; which claims priority to U.S. Provisional Patent Application Ser. No. 61/143,010, filed Jan. 7, 2009; the contents of each of which are incorporated by reference herein in their entireties.

TECHNICAL FIELD

The present invention relates generally to the removal of tissue, a non-limiting example of which is the removal of cataract material from the eye of a patient. The invention also relates to utilizing vacuum pulses to fragment and/or degrade tissue to be removed.

BACKGROUND

Many surgical procedures entail the removal of tissue from the surgical site of operation, including various kinds of ophthalmological procedures. One example of a frequently performed procedure is cataract surgery. The instrument of choice for removing cataracts has been the phacoemulsification ("phaco") device. Phaco technology utilizes ultrasound as the energy modality to fragment and remove the cataract. Specifically, phaco technology uses mechanical ultrasound energy to vibrate a small titanium needle that fragments the cataract material. Aspiration is applied through the titanium needle to remove the cataract material from the eye. A coaxial sleeve supplies irrigation fluid to the eye during the procedure to help neutralize the large amount of heat generated by the vibrating needle.

Phaco technology has many shortcomings. The high ultrasonic energy utilized may result in thermal damage to ocular tissue at the incision site. Moreover, phaco technology is expensive and the phaco procedure is complex and known to have an extended learning curve. Developing nations have been attempting to adopt phaco technology for a number of years, but progress has been slow in many of these countries because of the high cost of the phaco devices and the difficulty surgeons experience in learning the phaco surgical method. There is also a desire on the part of surgeons to make the incision smaller than the current 3.0-mm standard to reduce the surgically induced astigmatism that can be created at the incision site during the phaco procedure. The phaco technique has a tendency to cause a thermal burn at the incision site if the incision is too snug around the phaco tip and its silicone-irrigating sleeve. Regardless of the degree of snugness, the high level of ultrasonic energy employed may cause a thermal burn at the incision or a corneal burn. Also, some of the new foldable intraocular lenses (IOLs) being developed can be inserted into the eye through a 2.5-mm incision. If the surgeon tries to remove the cataract through an incision of this size, there is a higher likelihood that he may experience a thermal effect resulting from the friction created from the ultrasound titanium tip and the silicone irrigation sleeve. This thermal effect can result in tissue shrinkage and cause induced astigmatism.

Moreover, the mechanical ultrasound energy delivered through the titanium tip of the phaco device creates a cavitation field that is intended, along with the mechanical movement of the tip, to fragment the cataract material but it may damage the iris or any ocular tissue or structure it comes in contact with during surgery. The surgeon must be very cautious when activating the ultrasound energy inside the eye. Due to the difficulty in controlling the ultrasound energy, the surgeon often tries to draw the cataract particles to the titanium tip through relatively high fluid flow. Most surgeons try to minimize the movement of the phaco tip in the eye because the high fluid flow and ultrasound energy field reaches well beyond the phaco tip itself. The broad propagation of ultrasonic waves and the cavitation are unavoidable byproducts of the phaco technique; both are potentially harmful and currently are limitations of conventional phacoemulsification.

In addition, ultrasound energy has a tendency to cause corneal edema, especially at higher levels. Many surgeons inject viscoelastic material into the eye prior to inserting the phaco tip into the anterior chamber of the eye to protect the cornea. Some surgeons use viscoelastic material during the stage of the cataract procedure where the IOL is inserted into the eye. Viscoelastic material is expensive and so any reduction in its use would reduce the cost of the cataract procedure.

Moreover, the ultrasound energy created by the phaco device also is known to damage the endothelial cells, located on the inner lining of the cornea. These cells are critical for quality of vision. The harder the cataract, the greater the endothelial cell loss due to the higher level of ultrasound required to emulsify the cataract. It has been reported that in the use of phaco technology, there is an average endothelial cell loss of 13.74% (1.5 to 46.66%) with cataracts that are from a one-plus to a three-plus hardness. It has also been reported that there is an average endothelial cell loss of 26.06% (6.81 to 58.33%) when removing four-plus hardness cataracts with a phaco device.

The amount of fluid utilized in cataract surgery can have a significant impact on the clarity of the cornea post-operatively and on the overall effectiveness of the surgical procedure. Current phaco devices operate with a partially closed phaco incision due to thermal heat concerns. This incision produces significant amount of fluid outflow from the eye during surgery. To compensate many systems must use higher aspiration flow rates to attract the lens material to the titanium needle. In combination with the higher flow rates, there is a tendency to create higher turbulence and compromise overall ocular chamber stability. It would therefore be more advantageous to be able to operate with a completely closed incision whereby outward fluid flow is directed only through the extraction cannula. With a non-ultrasonic device, such as the device taught in the present disclosure that instead operates on an occlusion principle, fluid use may be minimal and surgical performance enhanced with reduced surgical time.

Moreover, in the future a smaller incision (approximately 1 mm) will be required in order to perform an endocapsular cataract removal to accommodate the injectable IOLs that are being developed by a number of IOL manufacturers. Current phaco technology will not be able to perform an endocapsular procedure due to the limitations in managing heat caused by the mechanical ultrasound.

In view of the foregoing, there is an ongoing need for apparatus and methods for tissue removal that are more cost effective; reduce the risk of damage and cause less damage to surrounding tissues of the surgical site such as a patient's eye, including reducing or eliminating ultrasound thermal energy; reduce the risk of post-operative complications; simplify and reduce the time of the procedure; and reduce the size of the incision site necessary for a given procedure, including accommodating the new Intraocular Lens (IOL) technologies currently under development.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a tissue removal device includes: a housing; a rigid aspiration cannula extending from the housing to a distal tip outside the housing; a valve disposed in the housing and configured for communicating with a vacuum source, the valve comprising a valve port communicating with the aspiration cannula in a fluid-sealed manner, wherein an inside diameter of the valve port is greater than an inside diameter of the distal tip; and a pneumatically-driven actuator configured for moving the valve between an open position and a closed position, wherein: at the open position, the valve port is open wherein the valve defines an aspiration path through the aspiration cannula and the valve; and at the closed position, the valve port is closed wherein the valve prevents vacuum from being applied at the distal tip.

According to another implementation, a tissue removal system includes: the tissue removal device; an aspiration line communicating with the valve and passing through the housing of the tissue removal device; and a cassette comprising a cassette interior, an aspiration inlet communicating with the aspiration line and the cassette interior, and a vacuum outlet communicating with the cassette interior and configured for communication with the vacuum source, wherein the cassette is configured for being operated in an installed position at which the cassette is removably inserted into a console, and at the installed position the vacuum outlet communicates with the vacuum source, wherein the aspiration path runs from the inner cannula, through the aspiration line and into the cassette interior.

According to another implementation, a device for applying a resilient membrane to a distal end of a cannula includes: an enclosure comprising a top surface, an interior, and a canal extending from the top surface into the interior along a canal axis; a support member disposed in the interior at a distance from the top surface, and circumscribing a support member opening of greater cross-sectional area than the canal; a resilient membrane disposed in the interior and comprising an open membrane end, an opposing closed membrane end, a membrane wall of nominally cylindrical cross-section between the open membrane end and the closed membrane end, and a membrane side port in the membrane wall, wherein the open membrane end is held by the support member in a stretched position such that the open membrane end is of greater cross-sectional area than the closed membrane end; and a rigid cannula extension comprising an open extension end, an opposing closed extension end, an extension wall between the open extension end and the closed extension end, and an extension side port between the open extension end and the closed extension end, wherein: the rigid cannula extension is disposed in the resilient membrane such that the membrane side port is aligned with the extension side port, the membrane wall is compressed around the extension wall, and the closed membrane end is compressed against the closed extension end; and the open extension end is generally aligned with the canal along the canal axis such that a cannula is insertable through the canal, through the resilient member, and into contact with the open extension end.

According to another implementation, a method for removing tissue from an eye includes: inserting a distal tip of an aspiration cannula of a tissue removal device through an incision formed in the eye and into an interior of the eye; breaking up tissue in the interior by applying a series of vacuum pulses to the tissue via the aspiration cannula, wherein applying the vacuum pulses includes pneumatically actuating a valve between an open position in which a valve port communicating with the aspiration cannula in a fluid-sealed manner is open and a closed position in which the valve port is closed, and wherein the aspiration cannula is rigid between the distal tip and the valve port; and aspirating the broken-up tissue through the aspiration cannula and to a tissue collection receptacle disposed remotely from the tissue removal device.

According to another implementation, the method includes, prior to breaking up tissue, placing the distal tip against a structure of the eye while applying a continuous vacuum pressure in the aspiration cannula, switching from applying the continuous vacuum pressure to applying a single vacuum pulse to the structure to form an incision through the structure, and inserting the distal tip through the structure.

According to another implementation, the method includes adjusting a pulse rate of the vacuum pulses by operating a control communicating with the valve and disposed remotely therefrom, wherein the control is selected from the group consisting of a user-operated console input and a user-operated foot switch.

According to another implementation, the method includes switching operation of the tissue removal device between a pulsed-vacuum mode and a continuous-vacuum mode by operating a control communicating with the valve and disposed remotely therefrom, wherein the control is selected from selected from the group consisting of a user-operated console input and a user-operated foot switch.

According to another implementation, the method includes controlling a rate of flow of broken-up tissue through the aspiration cannula by adjusting a frequency of the vacuum pulses.

According to another implementation, the method includes, prior to inserting the distal tip, inserting the aspiration cannula into a cylindrical cannula seal, wherein after inserting the distal tip the cylindrical cannula seal establishes a fluid seal between the incision and the aspiration cannula.

According to another implementation, the tissue collection receptacle is a cassette and the aspiration cannula communicates with the cassette via an aspiration line, and the method includes, prior to inserting the distal tip, establishing communication between the aspiration line and a vacuum source by inserting the cassette into a console of which the vacuum source is a part.

According to another implementation, the valve is actuated by an actuator of the tissue removal device that communicates with a gas line, and the method includes, prior to inserting the distal tip, establishing communication between the gas line and a pressurized gas source of the console by inserting the cassette into the console.

According to another implementation, the cassette includes a first collection chamber communicating with the aspiration line and a second collection chamber communicating with the first collection chamber via a cassette valve, and the method includes opening the cassette valve to transfer broken-up tissue from the first collection chamber to the second collection chamber.

According to another implementation, the method includes sensing when a level of broken-up tissue has reached a threshold in the first collection chamber and, in response, opening the cassette valve.

According to another implementation, the method includes, after aspirating the broken-up tissue, removing the distal tip from the incision; applying a resilient membrane to the aspiration cannula such that the distal tip contacts a rigid cannula extension in the resilient membrane and a side port of the rigid cannula extension is aligned with a side port of the resilient membrane; inserting the distal tip into the eye; and removing additional material from the eye via aspirating through the side ports of the rigid cannula extension and the resilient membrane.

According to another implementation, a method for applying a resilient membrane to a distal end of a cannula includes: inserting the distal end through a canal of an enclosure and into an open end of a resilient membrane disposed in the enclosure, wherein the open end is supported in a stretched state by a support member disposed in the enclosure; continuing to insert the distal end until the distal end makes contact with a rigid cannula extension disposed in the resilient membrane, wherein the rigid cannula includes a side port aligned with a side port of the resilient membrane; continuing to insert the distal end until the open end moves out of contact with a support member of the enclosure, wherein the resilient membrane surrounds the distal end and at least a portion of the cannula proximal to the distal end in a fluid-sealed manner; and removing the cannula from the enclosure.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 10 is a cross-sectional view of an example of a structure of a tissue removal device forming its internal aspiration line, with a vacuum pulsing device in an open position.

FIG. 11 is another cross-sectional view of structure illustrated in FIG. 10, with the vacuum pulsing device in a closed position.

FIG. 41 is a perspective view of an example of a cylindrical cannula seal according to an implementation.

FIG. 42 is a side view of the cannula seal illustrated in FIG. 41.

FIG. 43A is a cut-away view of a device for applying a resilient membrane to the distal end of the aspiration cannula, according to an implementation.

FIG. 43B is a cut-away view of the device illustrated in FIG. 43A, showing a cannula being inserted therein.

FIG. 43C is a side view of the cannula with the resilient membrane installed thereon.

DETAILED DESCRIPTION

Figure 1:
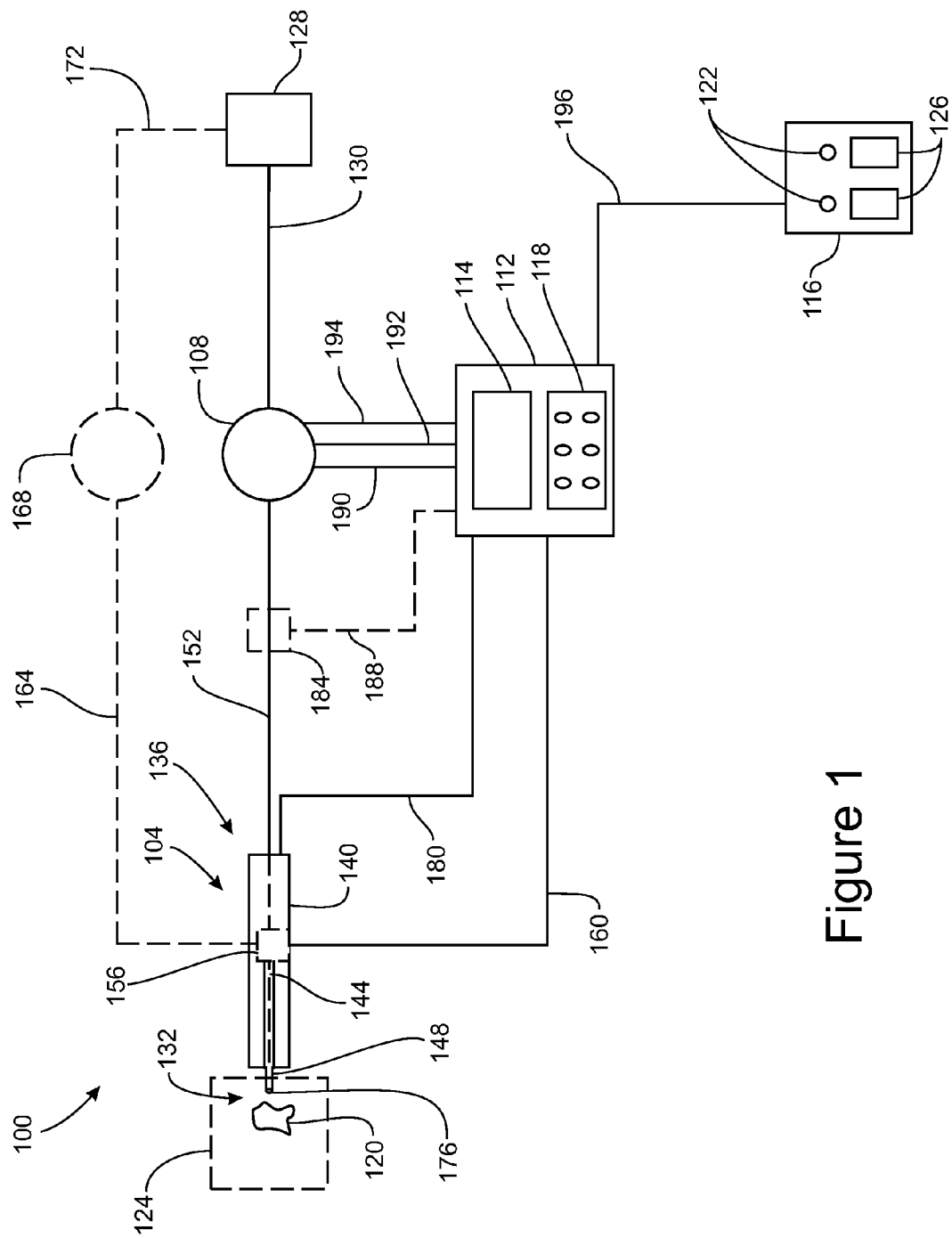
FIG. 1 is a block diagram illustrating an example of a tissue removal system according an implementation of the present invention.

FIG. 1 is a block diagram illustrating an example of a tissue removal system 100 according an implementation disclosed herein. The tissue removal system 100 generally includes a tissue removal device 104, a vacuum pump 108, and one or more system control devices such as a control console 112 and a foot-operated control device 116. In typical implementations, the tissue removal device 104 is structured and sized to be comfortably handheld by a user, and thus may be referred to as a hand piece, a handheld instrument, or a handheld device. Other components of the tissue removal system 100 may be stationary or portable and desired or appropriate for a particular procedure for which the tissue removal system 100 is utilized. The tissue removal device 104 and various other components may be provided to a surgeon in a sterile, preassembled form adapted to be quickly and easily interconnected to complete the tissue removal system 100. The tissue removal device 104 and various other components may be constructed of disposable materials.

Generally, the tissue removal system 100 is adapted for use by a surgeon (or other type of user) to remove target tissue 120 from a surgical site 124 through controlled application of vacuum or both vacuum and thermal energy at a distal tip of the tissue removal device 104. In the present context, target tissue 120 generally encompasses any tissue desired to be removed from the surgical site 124. As an example, the target tissue 120 may be cataract material to be removed from a patient's eye. Vacuum may be utilized not only for aspirating target tissue 120 from the surgical site 124 but also as a modality for breaking up the target tissue 120. Thermal energy may also be utilized for assisting in breaking up the target tissue 120. The tissue removal system 100 may also include a tissue collection site 128 such as may be embodied by any suitable receptacle, container or the like, communicating with the vacuum pump 108 via an outlet line 130, for enabling collection and disposal of aspirated tissue in a sterile manner. Depending on the particular application, the tissue removal system may also be configured to add certain types of materials to the surgical site via the tissue removal device. For example, the tissue removal system may be adapted to apply irrigation fluid to the surgical site, or such function may be performed by a separate instrument. As other examples, the tissue removal device may be configured to inject a material that absorbs cortical material, or a gel or other refractive material that replaces a human lens, a flowable IOL material, etc.

The tissue removal device 104 generally includes an open distal end 132 adapted to be positioned and operated at the surgical site 124, and an opposing proximal end 136. The tissue removal device also includes a housing 140 enclosing various components. As noted above, the housing 140 may be configured (sized, shaped, etc.) to be held in the hand of a surgeon. In advantageous implementations, the housing 140 is constructed of a material that is both electrically and thermally insulating to protect the surgeon, non-limiting examples of which are various thermoplastics and other polymeric compositions. One or more components of the tissue removal device 104 (conduits, tubing, chambers, etc.) provide an internal vacuum (or aspiration) line 144 that runs through the housing 140 generally from the open distal end 132 to or at least toward the proximal end 136. Part of the internal aspiration line 144 is established by a cannula 148 that may extend from a distal opening of the housing 140 over a short distance and terminate at an open distal tip corresponding to the open distal end 132 of the tissue removal device 104. By way of an appropriate fitting (not shown) of the tissue removal device 104 typically located at or near the proximal end 136 (i.e., a proximal opening of the housing 140), the internal aspiration line 144 may be placed in fluid communication with the vacuum pump 108 via connection with an external aspiration line 152 of any suitable length.

The tissue removal device 104 may also include a vacuum pulsing device 156 located within the housing 140 in operative communication with the internal aspiration line 144. With the vacuum pump 108 establishing a controlled level of vacuum, the vacuum pulsing device 156 may be operated to generate vacuum pulses of controlled frequency and duration. For this purpose, the vacuum pulsing device 156 may be placed in electrical communication with the control console 112 via a vacuum pulse control signal line 160. The vacuum pulsing device 156 may be configured in any manner suitable for generating vacuum pulses, some examples of which are described below. To optimize the effect of the vacuum pulsing, the part of the internal aspiration line 144 between the vacuum pulsing device 156 and the open distal end 132 should be rigid so that the as-generated pulsed energy is preserved as it is transferred to the distal end 132. That is, soft conduit materials (e.g., flexible tubing) should be avoided in this part of the internal aspiration line 144 as such materials might provide an undesired damping effect on the pulsed energy. The cannula 148 should thus be constructed from rigid material(s). Depending on the design of the tissue removal device 104, the illustrated cannula 148 may extend from its distal tip to the vacuum pulsing device 156, i.e., over the entire portion of the internal aspiration line 144 that should be rigid. Alternatively, one or more other distinct conduits may be provided between the cannula 148 and the vacuum pulsing device 156, in which case such other conduits should likewise be rigid.

In operation, the vacuum pump 108 provides a base level of vacuum for the tissue removal device 104. This vacuum level may be controlled and adjusted as needed by the surgeon for aspirating tissue. Over any given time period during a tissue removal procedure, the surgeon may set the level of vacuum to be constant or may vary the vacuum level. The vacuum pulsing device 156 may be operated to pulse the vacuum generated by the vacuum pump 108. Vacuum pulsing may be performed for any number of purposes, an example of which is to break up target tissue 120 prior to its aspiration. In one particular example, the pulsed vacuum energy is utilized to break up cataract material. The overall duration of the vacuum pulsing (i.e., the time during which the vacuum pulsing device 156 is active), as well as the pulsing parameters (e.g., the magnitude and duration/frequency of the pulses), may be determined by the surgeon. As examples, the surgeon may be allowed to select among various preset (predetermined, preprogrammed, etc.) vacuum pulsing programs, and/or may be allowed to adjust the vacuum pulsing parameters in real time (on the fly). The surgeon may control the operating parameters of the vacuum pump 108 and the vacuum pulsing device 156 by utilizing the control console 112 and/or the foot control device 116.

Figure 2:
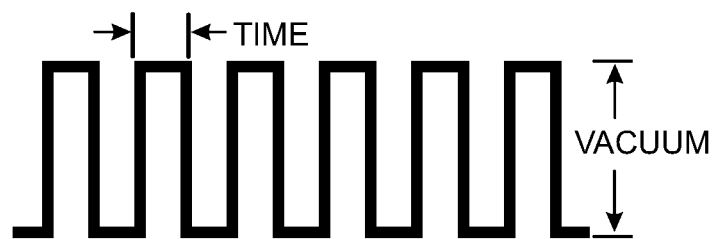
FIG. 2 is an example of a pulsed vacuum signal that may be applied by the tissue removal system.
Figure 3:
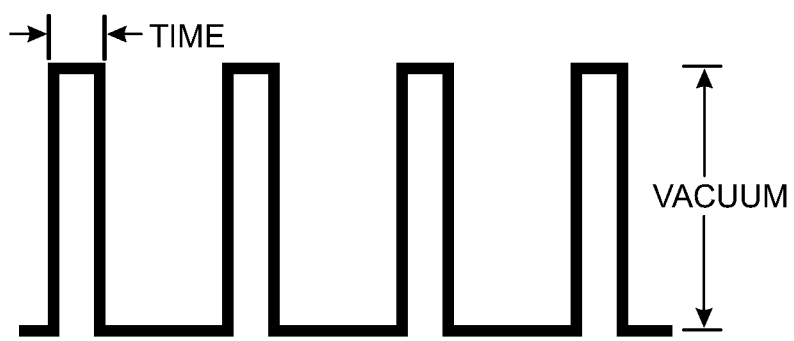
FIG. 3 is another example of a pulsed vacuum signal that may be applied by the tissue removal system.

A few examples of vacuum pulsing programs (or profiles) that may be implemented by the vacuum pulsing device 156 are illustrated in FIGS. 2 and 3. Specifically, FIG. 2 is an example of a pulsed vacuum signal characterized by a relatively high-frequency pulse and moderate vacuum level. FIG. 3 is an example of a pulsed vacuum signal characterized by a relatively low-frequency pulse and high vacuum level. In advantageous implementations, the pulse trains have a stepped profile (i.e., are step functions or square waves) as shown in FIGS. 2 and 3, in which the vacuum level abruptly switches between a high value and a low value (which may correspond to zero vacuum or very low vacuum). That is, the transitions between the high and low values are not ameliorated by ramps or curved functions. By this manner, the pulses in effect constitute a sequence of discrete impacts that are effective for breaking up target tissue 120.

For certain specific purposes of vacuum pulsing, such as the breaking up of certain types of tissue, it may be desirable or necessary for the magnitude of the vacuum pulses to be significantly higher than the magnitude of the base vacuum provided by the vacuum pump 108. Hence, the operation of the vacuum pulsing device 156 may be coordinated with the operation of the vacuum pump 108, which may be done automatically by the control console 112. For instance, the control console 112 may be configured to step up the vacuum level generated by the vacuum pump 108 upon activation of the vacuum pulsing device 156, and likewise to step down the vacuum level upon deactivation of the vacuum pulsing device 156. Moreover, as a safety feature, the control console 112 may be configured to shut down the vacuum pump 108 upon deactivation of the vacuum pulsing device 156, or upon sensing a failure of the vacuum pulsing device 156. This type of coordination is particularly useful for certain types of tissue removal procedures such as cataract removal and other ophthalmological procedures. In such operating environments, the higher vacuum level at which the vacuum pulsing operates could, in the absence of the pulsing, create a potentially harmful high fluid flow-rate condition. That is, when the distal tip of the tissue removal device 104 is located in a fluid environment such as the interior of a patient's eye, the vacuum established by operation of the vacuum pump 108 establishes a fluid flow in the direction from the fluid environment toward the vacuum pump 108, through the cannula 148 and all other fluid conduits comprising the aspiration line. When the vacuum pulsing device 156 is not being operated, the flow rate primarily depends on the level of vacuum applied by the vacuum pump 108. The tissue removal system 100 is configured to operate the vacuum pump 108 so as to apply vacuum within a range of magnitudes determined to be effective for aspirating target tissue 120 without damaging or otherwise detrimentally affecting nearby tissue or other structures. On the other hand, when the vacuum pulsing device 156 is also active, the vacuum pulses—i.e., the cyclical breaking and restoring of the vacuum applied at the distal tip—significantly affects the fluid flow rate. Generally, the higher the vacuum pulse rate the lower the fluid flow rate, and the lower the vacuum pulse rate the higher the fluid flow rate. Thus, high-frequency vacuum pulses may be applied at a relatively high magnitude to very effectively break up target tissue 120 in a safe manner because the resultant fluid flow rate remains within a safe range. If, however, the vacuum were to remain at that high magnitude after pulsing ceases—due to either deactivation or failure of the vacuum pulsing device 156—then fluid flow rate might quickly increase to an unsafe level. For certain critical surgical sites such as a patient's eye, this sudden jump in fluid flow and/or sudden transition to a continuously applied (non-pulsed) high-magnitude vacuum could cause rapid fluid loss and injury to the patient. Therefore, to eliminate the risk of injury, it is advantageous to coordinate the respective operations of the vacuum pump 108 and the vacuum pulsing device 156.

As just noted, higher vacuum pulse rates result in lower fluid flow rates, and lower vacuum pulse rates result in higher fluid flow rates. Thus, while the tissue removal device 104 is operating in the vacuum-pulse mode the surgeon can control the fluid flow rate, and hence the flow rate of the broken up tissue being aspirated through the tissue removal device 104, by varying the frequency of the vacuum pulses being applied by the vacuum pulsing device 156. The vacuum pulse frequency may be varied by, for example, manipulating an appropriate adjustment knob located on the control console 112 or the foot control device 116. As a safety feature similar to that just described, circuitry provided with the control console 112 or the foot control device 116 may be configured to detect whether a predetermined lower threshold of the vacuum pulse frequency has been reached, and if so respond by automatically lowering the magnitude of the applied vacuum to avoid a dangerously high flow rate. As another safety feature, the foot control device 116 may be configured so as to require a foot switch of the foot control device 116 to remain depressed in order for the vacuum pulsing mode to remain active. By this configuration, if the surgeon intentionally or accidentally removes his foot from the foot switch, the tissue removal system 100 is automatically switched to a continuous vacuum mode with a low vacuum level, or the vacuum pump 108 is automatically shut off, or a valve mechanism of the vacuum pulsing device 156 automatically closes off the aspiration line 144 so as to cut-off application of the vacuum to the distal tip of the cannula 148, etc.

As further shown in FIG. 1, in some implementations the tissue removal system 100 may include a low-vacuum line and a separate high-vacuum line. The above-described first aspiration line 152 is utilized as the low-vacuum line and a second aspiration line 164 is utilized as the high-vacuum line. The first aspiration line 152 and the first vacuum pump 108 are active during the continuous or steady-state vacuum mode in which the surgeon may vary the vacuum level within a range of relatively low vacuum levels. The high-pressure aspiration line 164 interconnects the vacuum pulsing device 156 and a fluid inlet of a second vacuum pump 168 configured for applying relatively higher levels of vacuum associated with the vacuum pulsing mode. Similar to the first vacuum pump 108, the second vacuum pump 168 is controlled by the control console 112 or the foot control device 116 via appropriate electrical signal lines (not shown). The first vacuum pump 108 and the second vacuum pump 168 may be the same type of pump or different types of pumps. The control console 112 or the foot control device 116 is configured to switch between operating the first vacuum pump 108 and the second vacuum pump 168 in accordance with the surgeon's selection of the continuous vacuum mode or the vacuum pulsing mode, or automatically in response to certain events as described elsewhere in the present disclosure. The vacuum pulsing device 156 may be configured to switch the flow path from the cannula 148 into either the first aspiration line 152 or the second aspiration line 164 depending on the mode selected. Thus, fluid and removed tissues flow through either the first aspiration line 152 or the second aspiration line 164. An outlet line 172 may interconnect a fluid outlet of the second vacuum pump 168 and the tissue collection site 128.

The tissue removal device 104 may also include a thermal element 176 located at the distal tip of the cannula 148. The thermal element 176 is adapted to apply localized heat energy to the target tissue 120. The heat energy has the effect of degrading the target tissue 120. In the present context, "degrading" generally means that the target tissue 120 is transformed to a state different from its original state and the different state facilitates the target tissue's removal from the surgical site 124 and/or aspiration through the tissue removal device 104. The precise mechanism of degradation will depend on the nature or composition of the target tissue 120. As a few non-limiting examples, degradation may entail breaking up the target tissue 120 into smaller fractions, denaturing the target tissue 120, depolymerizing the target tissue 120, melting the target tissue 120, etc. In some implementations, the thermal element 176 is an electrically resistive heating element responsive to DC current. The thermal element 176 may be controlled by the control console 112 via a heating signal line 180 that passes a desired magnitude of DC current to the thermal element 176 through one or more electrically conductive components of the tissue removal device 104. As one non-limiting example, the control console 112 may be configured to energize the thermal element 176 over a current range that allows the temperature of the thermal element 176 to be varied within a range of about 40-70° C. The control console 112 may also be configured to transmit pulsed DC current over the heating signal line 180 so as to cause the thermal element 176 to apply pulsed thermal energy. The heating signal line 180 may represent two electrical lines respectively communicating with two terminals or contact points of the thermal element 176, thereby establishing a circuit in which current passes through one electrical line, through the thermal element 176 and through the other electrical line. One or more operating parameters of the thermal element 176 may alternatively or additionally be controlled by the foot control device 116, as described further below.

The thermal element 176 may generally be constructed of any electrically conductive yet electrically resistive material, i.e., a material effective for converting a substantial portion of the electrical energy passing through it to heat energy. Thus, a variety of metals and metal alloys may be utilized. Preferably, the thermal element 176 is composed of a material highly responsive to electrical current, i.e., a highly resistive (or poorly conductive) material, or stated in another way, a material that readily dissipates heat in response to electrical current. One non-limiting example is nichrome. In some implementations, the thermal element 176 may be coated with a material that gives the thermal element 176 a non-stick quality to prevent adhesion or retention of target tissue 120 to the thermal element 176. Non-limiting examples of suitable non-stick coatings include various polymer compositions of the Parylene family as well as chemical derivatives and relatives thereof.

Figure 4:
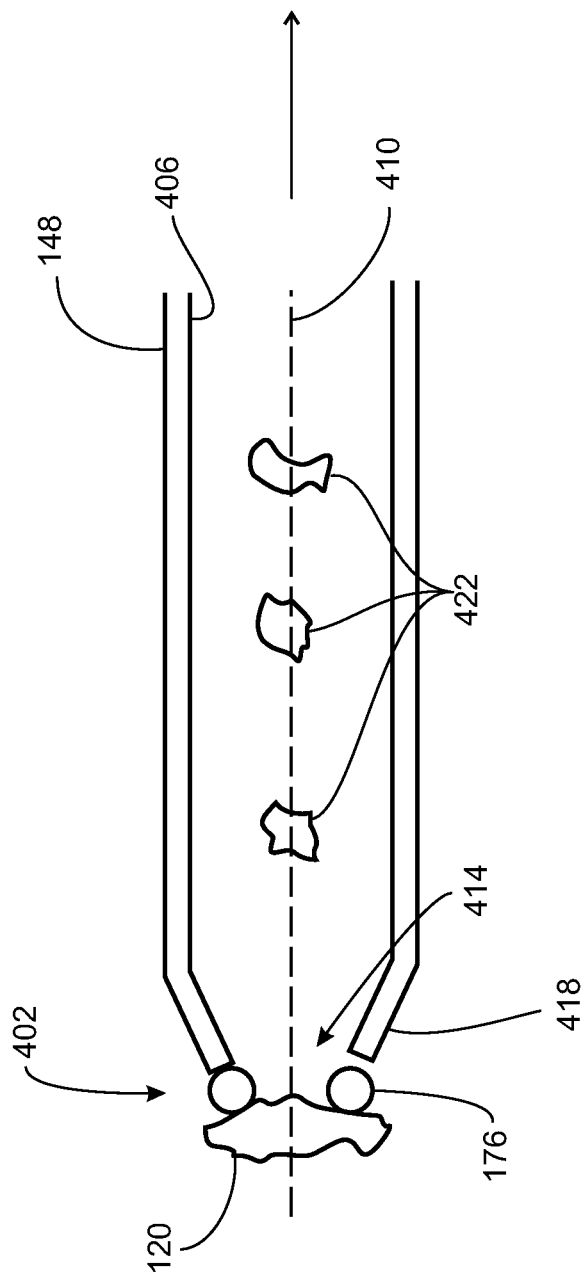
FIG. 4 is a cross-sectional view of an example of a thermal element and a cannula that may be provided by a tissue removal device according to an implementation disclosed herein.
Figure 5:
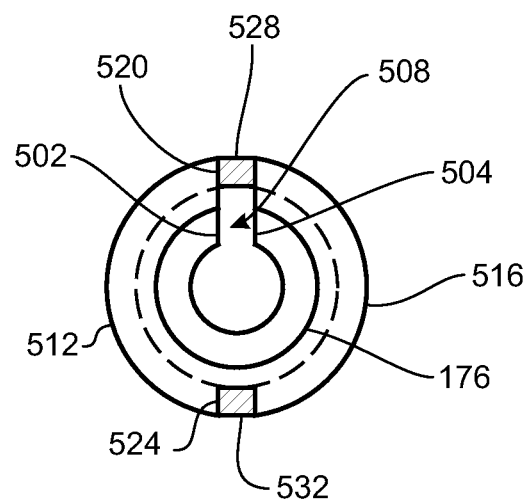
FIG. 5 is an end view of the thermal element and cannula from an outside perspective.

FIG. 4 is a cross-sectional view of an example of a distal region of the tissue removal device 104. More specifically FIG. 4 illustrates, in cross-section, a distal region of the cannula 148 and the thermal element 176 positioned at a distal tip 402 of the cannula 148. An inner surface 406 of the cannula 148 circumscribes the interior of the cannula 148. The inside diameter of the inner surface 406 dictates the cross-sectional flow area through the cannula 148. In this example, the thermal element 176 and the cannula 148 are coaxially arranged about a longitudinal axis 410. An arrow collinear with the longitudinal axis 410 generally depicts the direction of the pressure gradient established by the applied vacuum and thus the direction of fluid flow and tissue aspiration. In this example, the thermal element 176 is provided in the form of a wire loop that defines an opening that serves as a fluid inlet 414 into the cannula 148 and thus corresponds to the open distal end 132 (FIG. 1) of the tissue removal device 104. Accordingly, the thermal element 176 is annular and coaxially surrounds the flow path for aspirated fluid and tissue. The size (internal diameter) of the fluid inlet 414 dictates the flow area into the cannula 176. This is also illustrated in FIG. 5, which is an end view of the thermal element 176 and cannula 148 from an outside perspective. The internal diameter of the thermal element 176 may be the same or substantially the same as the internal diameter of the cannula 148, in which case the flow area is preserved along the axial length of the cannula 148. In other implementations, as illustrated in FIGS. 4 and 5, the internal diameter of the thermal element 176 may be less than the internal diameter of the cannula 148, with the diametrical transition being provided by a tapered (or conical) section 418 of the cannula 148. This configuration may be useful for preventing the cannula 148 from clogging because any tissue small enough to traverse the fluid inlet 414 defined by the smaller-diameter thermal element 176 carries little risk of clogging the larger cross-sectional flow area defined by the cannula 148. As shown in FIG. 5, the thermal element 176 may be C-shaped in that it has two terminal ends 502, 504 separated by a gap 508. By this configuration, respective electrical leads may be attached or otherwise placed in electrical contact with the terminal ends 502, 504 to complete the circuit for passing DC current through the thermal element 176. The electrical leads may in turn communicate with the control console 112 via the heating signal line 180 diagrammatically depicted in FIG. 1.

The tissue removal device 104 may be utilized in a variety of procedures that entail inserting the cannula 148 into a surgical site via an incision. For instance, in various ophthalmological procedures, an incision may be made through a membrane of a patient's eye. The incision may be made by various techniques such as, for example, a laser procedure. To minimize damage to the eye and minimize post-surgery recovery and healing periods, the incision should be as small as possible. Therefore, the cannula 148 should be as small as practicably possible. The design of the cannula 148 and thermal element 176 disclosed herein enables the sizes of these components to be minimized without adversely affecting their functions. In some implementations, the outer diameter of the cannula 148 ranges from about 1.0-3.0 mm. In some examples, the outer diameter of the cannula 148 is about 3.0 mm, 2.5 mm, 2.0 mm, 1.5 mm, or 1.0 mm. As noted elsewhere, the outer diameter of the thermal element 176 may be about the same or less than the outer diameter of the cannula 148. In some examples, the outer diameter of the thermal element 176 is about 1.7 mm or less. The size of the cannula 148 is able to be minimized in part because the tissue removal device 104 itself is not required to provide a means for supplying irrigation fluid to the surgical site. The utilization of the vacuum pulsing effect and the thermal effect disclosed herein does not require nearly as much irrigation fluid as tissue removal techniques of the prior art. Any irrigation fluid needed to be added to the surgical site may be supplied by a separate hand-held device. This may be referred to as a bimanual technique in which the surgeon wields the tissue removal device 104 in one hand and an irrigating device in the other hand as needed. Alternatively, the tissue removal device 104 may be configured for performing a coaxial technique in which irrigation fluid is supplied by the tissue removal device 104 through an annular sleeve (not shown) coaxial with the cannula 148. This latter alternative would require a larger incision, although the incision may still be less than 3.0 mm.

FIG. 4 also illustrates an example of the thermal effect implemented by the thermal element 176. In this example, the target tissue 120 (such as, for example, a cataract or portion of a cataract) has been drawn to the fluid inlet 414 under the influence of the applied vacuum. The target tissue 120, however, is larger than the fluid inlet 414 and hence initially comes into contact with the thermal element 176 and occludes the fluid inlet 414. In some situations, the applied vacuum may be sufficient to deform the target tissue 120 enough to enable the target tissue 120 to traverse through the fluid inlet 414 and flow through the cannula 148, out from the tissue removal device 104, and through associated aspiration lines to a desired destination (e.g., the collection site 128 illustrated in FIG. 1). In other situations, the target tissue 120 may be too large and/or not sufficiently deformable to be aspirated solely under the influence of the applied vacuum, and/or the implementation of the vacuum pulsing effect may not be effective enough to break up the target tissue 120. In these latter situations, the thermal element 176 may be energized to apply heat energy to the target tissue 120 and thereby break up the target tissue 120 into smaller fragments 422 more easily transported through the fluid inlet 414 and cannula 148.

Additionally, the tissue removal system 100 may be configured to detect the occurrence of occlusion and automatically activate the thermal element 176. Various approaches may be taken for detecting the occluding event.

As one non-limiting example, the tissue removal system 100 may provide a pressure transducer 184 (FIG. 1), operatively interfaced with the aspiration line 152 at an appropriate location thereof, which provides continuous or intermittent pressure feedback signals to the control console 112 via a pressure feedback signal line 188. The detection of an abrupt change in pressure (or vacuum) level in the aspiration line 152 may be interpreted as the occurrence of an occluding event at the fluid inlet 414 (FIG. 4) and automatically trigger activation of the thermal element 176. Likewise, when the tissue removal system 100 is operating in continuous vacuum mode, the detection of an occluding event may trigger activation of the vacuum pulsing mode. The control console 112 may be configured to decide whether to automatically trigger the vacuum pulsing mode and/or the thermal application mode, and whether to activate both modes simultaneously or sequentially, depending on the current state of operation of the tissue removal device 104 at the time of detection of an occlusion. When it is subsequently detected that the occlusion has been lost, the control console 112 may be configured to deactivate the vacuum pulsing device 156 and/or the thermal element 176, and/or may shut down the vacuum pump(s) 108, 168 or otherwise cause vacuum to be cut off at the distal tip 402. For the purpose of detecting occlusions, the pressure transducer 184 may be positioned in the housing 140 (FIG. 1) of the tissue removal device 104 in operative communication with some portion of the internal aspiration line 144. Alternatively, as shown in FIG. 1 the pressure transducer 184 may be positioned in operative communication with the external aspiration line 152 or 164, or within the housing of the vacuum pump 108 or 168.

It will be noted that the effectiveness of the thermal effect does not in all situations require actual contact between the target tissue 120 and the thermal element 176. For instance, upon inserting the distal tip 402 of the cannula 148 into a surgical site, the thermal element 176 may be located at a small distance from the target tissue 120. The thermal element 176 may then be activated while it is in proximity to, but not contacting, the target tissue 120. Heat energy from the thermal element 176 may be transferred to the target tissue 120 through a small portion of the fluid medium existing between the thermal element 176 and the target tissue 120 such as air or fluid (e.g., intraocular fluid in the case of an ophthalmologic procedure, and/or irrigation fluid as may be applied in a variety of surgical procedures). A sufficient amount of heat energy may be transferred through the fluid medium to cause the target tissue 120 to begin to break up prior to the target tissue 120 being drawn to the fluid inlet 414 surrounded by of the thermal element 176. Alternatively or additionally, the target tissue 120 may begin to break up while in transit toward the fluid inlet 414 due to the transfer of heat from the thermal element 176.

In all such situations, it is evident that the thermal effect is highly localized. The thermal element 176 is shaped so as to present an outer surface area that concentrates the emitted heat energy directly into the fluid inlet 414 and the immediate vicinity of the fluid inlet 414. The thermal effect is effective and rapid enough that no substantial portion of fluid volume in which the target tissue 120 resides needs to become heated to any appreciable degree. The thermal effect is also effective and rapid enough that the heat energy need only be applied for a very brief period of time. This period of time is insufficient for surrounding non-targeted tissue to be adversely affected by the applied heat energy. This is particularly so in procedures entailing the circulation of irrigation fluid through the surgical site as the irrigation fluid absorbs excess heat energy deposited by the thermal element 176. The period of time for heat activation may also be minimized by applying pulses of heat energy as noted above, in procedures where a pulsed thermal effect is found to be more effective than a constant application of heat. Moreover, the thermal element 176 is positioned, sized and shaped such that the surgical site is exposed to a minimal surface area of the thermal element 176. As an example, the distance over which the thermal element 176 extends axially outward from the distal tip 402 of the cannula 148 may be about 2 mm or less. In other implementations, the thermal element 176 may be positioned so as to be partially or fully recessed within the distal tip 418 of the cannula 148.

Figure 6:
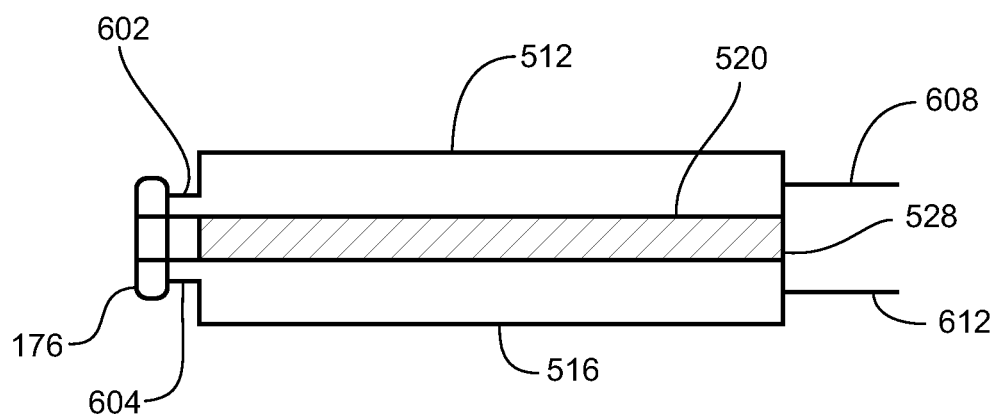
FIG. 6 is a top view of the thermal element and cannula illustrated in FIGS. 4 and 5.

FIGS. 4 and 5 additionally illustrate an implementation in which the structure of the cannula 148 itself is utilized to conduct DC current to the thermal element 176. This implementation is also illustrated in FIG. 6, which is a top view of the thermal element 176 and cannula 148 illustrated in FIGS. 4 and 5. In this case, the cannula 148 has a split-structured design in which the cannula 148 includes two C-shaped or semicircular, electrically conductive structural members 512, 516 extending along the longitudinal axis 410. The structural members 512, 516 may be composed of any suitable conductive material. In advantageous implementations, the structural members 512, 516 are composed of a material that is a very good conductor, i.e., conducts electricity very efficiently and thus without generating undue amounts of resistive heat. In this manner, the thermal effect imparted by the thermal element 176 remains localized at the distal tip 402 of the cannula 148 and very little heat is emitted by the cannula 148. This is particularly useful for avoiding thermal damage to membranes or other tissues through which an incision has been made and which may therefore be in direct contact with the outer perimeter of the cannula 148 extending through the incision. Non-limiting examples of materials suitable for the cannula members 512, 516 include aluminum, copper, nickel, and various precious metals (e.g., gold, silver, platinum, etc.).

From the perspective of FIG. 5, the structural members 512, 516 of the cannula 148 are separated from each other by an upper gap 520 and a diametrically opposing lower gap 524. As shown in FIG. 6, the gaps 520, 524 are axially elongated and continue along the entire axial distance of the cannula 148. By this configuration, the two members 512, 516 are electrically isolated from each other and hence may be utilized as electrical conduits for passing DC current to the thermal element 176. For this purpose, the two members 512, 516 may include respective extensions 602, 604 (or projections, tabs, or the like) in electrical contact with the terminal ends 502, 504 of the thermal element 176. All other conductive portions of the cannula 148 are physically separated from the thermal element 176. As diagrammatically depicted in FIG. 6, the two members 512, 516 may respectively communicate with two other electrical conductors 608, 612 that may be provided in the tissue removal device 104, which in turn may communicate with or form a part of the heating signal line 180 shown in FIG. 1.

To fully enclose the fluid volume circumscribed by the cannula 148 and seal this part of the aspiration line, axially elongated seals 528, 532 may be positioned so as to respectively fill the gaps 520, 524 between the cannula members 512, 516. The axial seals 528, 532 may be composed of any suitable electrically insulating material. In other implementations, the seals 528, 532 may be radial projections extending from a structure of the tissue removal device 104 external to the cannula 148, such as a cylinder that partially or fully surrounds the two members 512, 516 of the cannula 148. The seals 528, 532 may also extend from or be supported by an internal portion of the housing 140 of the tissue removal device 104.

Figure 7:
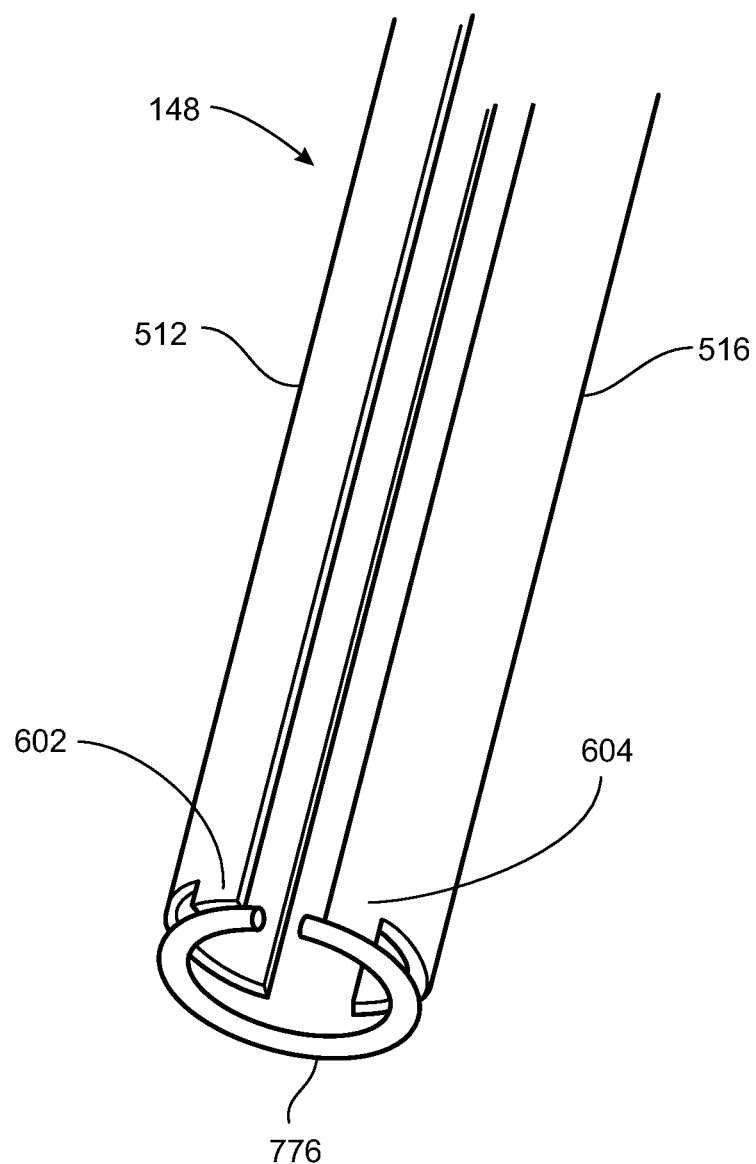
FIGS. 7, 8 and 9 are perspective views of the cannula and respective examples of how the thermal element may be structured.
Figure 8:
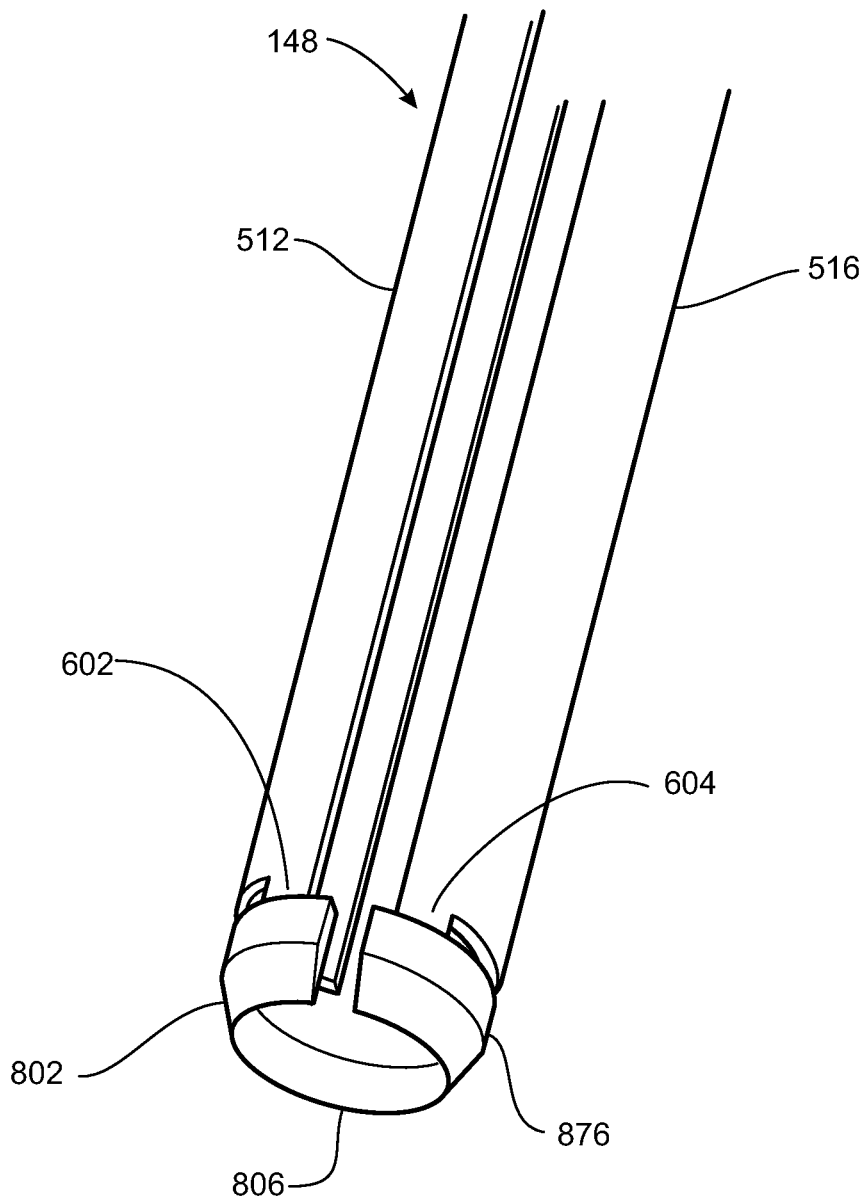
Figure 9:
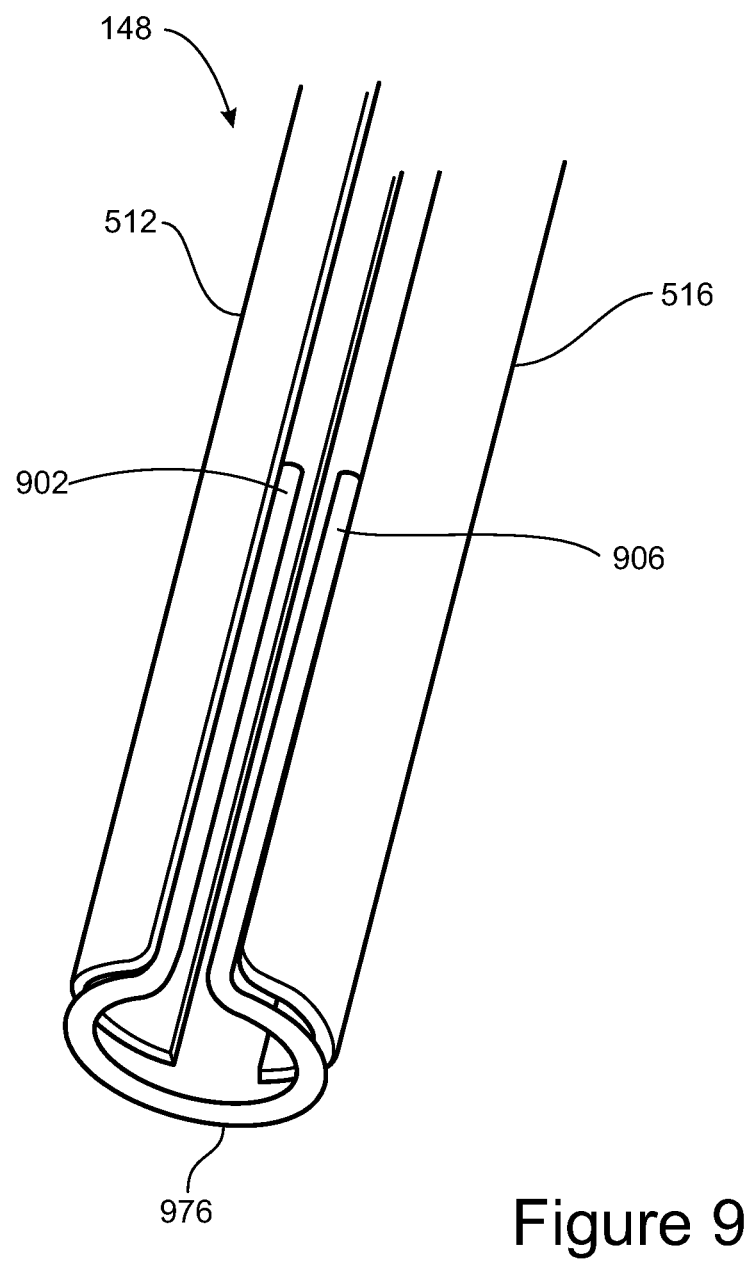

FIGS. 7, 8 and 9 are perspective views of the distal portion of the cannula 148 and respective examples of how the thermal element may be structured. In each of these examples, the cannula 148 has the above-described split design with two curved members 512, 516 electrically isolated from each other. For ease of illustration, seals interposed between the members 512, 516 are not shown. Also, in these examples, the cannula 148 has a constant diameter. FIG. 7 illustrates a thermal element 776 that is ring-shaped with a gap 508, similar to that described above and illustrated in FIGS. 4, 5 and 6. FIG. 8 illustrates a thermal element 876 that is also ring-shaped with a gap 508. In comparison to FIG. 7, the thermal element 876 of FIG. 8 has a larger axial dimension. This facilitates shaping the thermal element 876 for specific purposes. For instance, as shown in FIG. 8, a distal-most portion 802 of the thermal element 876 may taper down to a sharp edge 806, which may assist in breaking up large target tissue drawn into contact with the thermal element 876 and/or provide an even more localized thermal effect at the sharp edge 806. In addition, the inside diameter of distal-most portion 802 may taper down from the inside diameter of the cannula 148 to prevent clogging in a manner similar to the tapered section 418 of the cannula 148 illustrated in FIGS. 4, 5 and 6. FIG. 9 illustrates a thermal element 976 that includes two axial legs 902, 906 extending in the axial direction along at least a portion of the length of the cannula 148. The axial legs 902, 906 may, for example, be positioned in one of the gaps between the split members 512, 516 of the cannula 148. The axial legs 902, 906 may be provided to extend the thermal effect over a desired length of the distal region of the cannula 148.

The positions of the thermal elements 776, 876, 976 may be fixed relative to their respective cannulas 148 in any suitable manner. For example, in FIG. 7 the terminal ends of the thermal element 776 may be placed in electrical communication with the respective cannula extensions 602, 604 by welding, soldering, or an electrically conductive adhesive. In FIG. 8, the thermal element 876 may be attached to its cannula 148 in a similar manner. In FIG. 9, the axial legs 902, 906 (serving as terminal ends) of the thermal element 976 may be attached to respective inside edges of its cannula 148 in a similar manner. Alternatively in FIG. 9, the axial legs 902, 906 may be attached to respective insulated wires (not shown) that run along the cannula 148 and in communication with the heater signal line 180 (FIG. 1). In this latter case, the structural members 512, 516 of the cannula 148 are composed of an electrically insulating material instead of a conductive material.

While the various cannulas 148 described thus far are oriented along a straight axis, this is not a limitation of the present teachings. In some implementations, the cannula 148 provided with the tissue removal device 104 may be curved or angled. In other implementations, the radius of curvature or the angle of the cannula 148 may be adjustable. That is, the surgeon may elect to utilize a straight-shaped cannula 148 or be able to bend the cannula 148 to conform to a desired curved or angled shape. This adjustability of the cannula 148 may be implemented in a variety of ways, such as by selecting a material that is malleable (yet still rigid so as not to dampen vacuum pulses), providing the cannula 148 in the form of a series of segments that are movable relative to each other, etc. An adjustable cannula 148 may be useful in certain surgical sites that are difficult to access, do not have straight boundaries, or have unpredictable boundaries. A few examples include blood vessels, various biological ducts, and various anatomical cavities.

FIGS. 10 and 11 are cross-sectional views of an example of a structure of the tissue removal device 104 forming its internal aspiration line 144. FIG. 10 shows the aspiration line 144 in an open position, while FIG. 11 shows the aspiration line 144 in a closed position. The structure includes the cannula 148, another suitable fluid conduit such as a tube 1002 in fluid communication with the cannula 148, and a vacuum pulsing device 1056 in operative communication with the aspiration tube 1002. The cannula 148 may be structured according to any of the implementations described herein. As noted above, the cannula 148 and at least that portion of the aspiration tube 1002 between the vacuum pulsing device 1056 and the cannula 148 should be rigid so as to optimize the vacuum pulsing effect. The vacuum pulsing device 1056 may have any design suitable for alternately closing and opening the fluid path through the aspiration tube 1002 and hence alternately breaking and restoring vacuum. For this purpose, in some implementations the vacuum pulsing device 1056 includes a movable member 1006 that may be actuated to alternately extend into and retract from the fluid path. The movable member 1006 may be configured to obstruct all or part of the fluid path when extended therein such that the cycling of the movable member 1006 between its extended and retracted positions generates vacuum pulses. As noted above, the vacuum pulsing effect may be utilized to break up target tissue. The vacuum pulsing effect may be implemented alternatively or in conjunction with the thermal effect. Moreover, the vacuum pulsing effect and the thermal effect may be implemented in sequence or simultaneously. When implemented in sequence, the vacuum pulsing effect may follow the thermal effect, or vice versa. The sequencing of the two effects may be repeated over one or more alternating cycles. Accordingly, in a given tissue removal procedure, a surgeon may elect to activate the vacuum pulsing effect only, or the thermal effect only, or both effects according to a desired sequence, or both effects simultaneously to achieve a synergistic effect.

In the example specifically illustrated in FIGS. 10 and 11, the vacuum pulsing device 1056 is a solenoid-based device that includes a solenoid actuator 1010. The movable member 1006 serves as the plunger that is translated by the actuator 1010. The movable member 1006 translates through an opening 1014 in the aspiration tube 1002. A seal of any suitable design may be provided at the physical interface between the movable member 1006 and the tube opening 1014 as needed to maintain the aspiration tube 1002 in a fluid-tight condition. As one non-limiting example, the seal may be an elastic material that covers the tube opening 1014. As the movable member 1006 translates into the aspiration tube 1002 through the tube opening 1014, the seal stretches and deforms around the movable member 1006, thereby covering the movable member 1006 as well as the tube opening 1014 and maintaining fluid isolation between the interior and exterior of the aspiration tube 1002.

Figure 12:
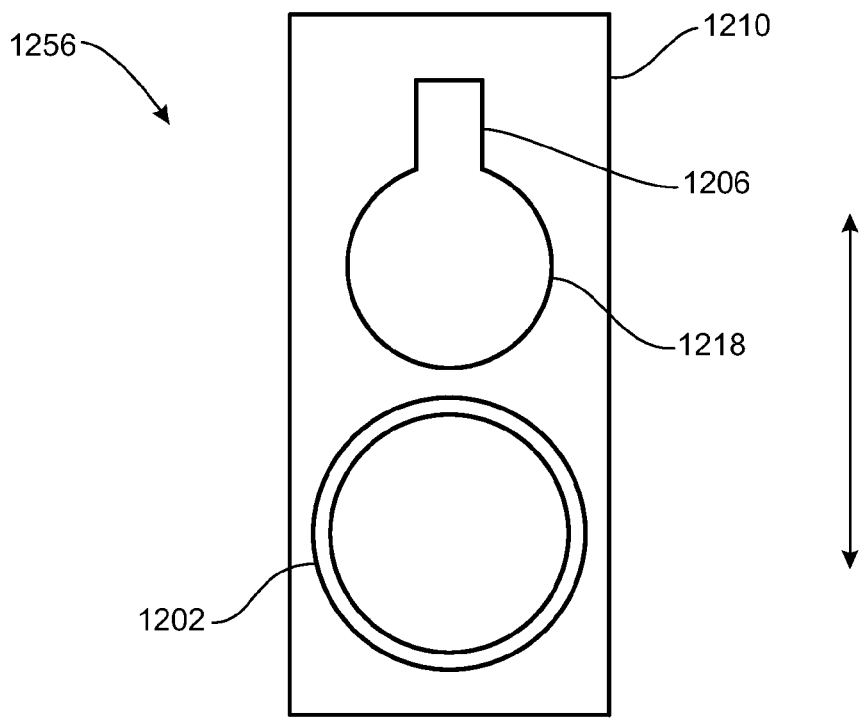
FIG. 12 is a cross-sectional view of another example of a vacuum pulsing device with a movable member thereof in a retracted position.
Figure 13:
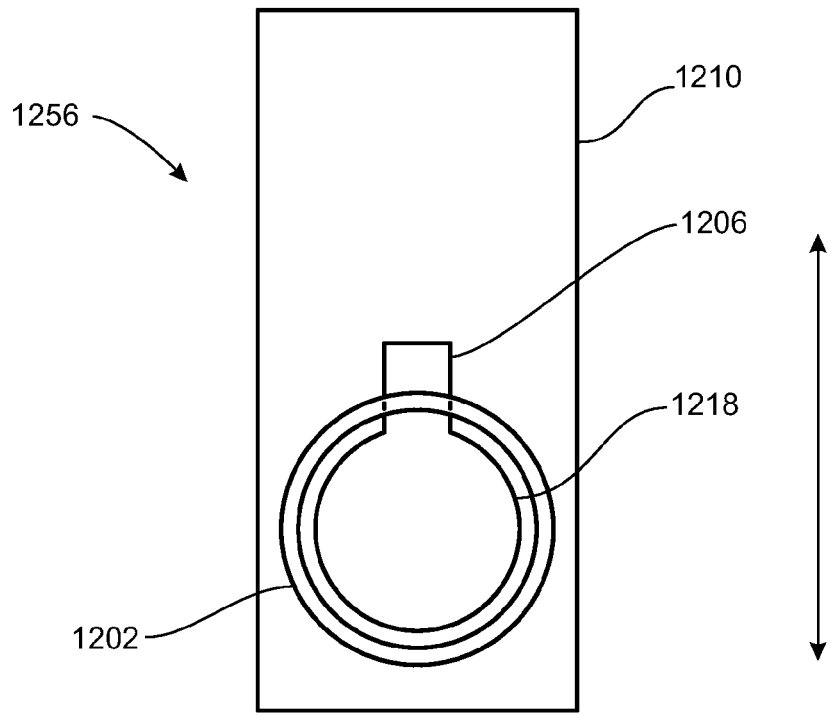
FIG. 13 is a cross-sectional view of the vacuum pulsing device illustrated in FIG. 12, with the movable member in its extended position.

FIGS. 12 and 13 are cross-sectional views of another example of a solenoid-based vacuum pulsing device 1256. The vacuum pulsing device 1256 includes a solenoid actuator 1210 and a movable member 1206 reciprocated by the actuator 1210 into and out from the flow path of an aspiration tube 1202 of the tissue removal device 104. FIG. 12 illustrates the movable member 1206 in its refracted position and FIG. 13 illustrates the movable member 1206 in its extended position. In this example, the movable member 1206 includes a distal section 1218 having a cross-sectional area substantially equal to the cross-sectional area of the aspiration tube 1202. By this configuration, the vacuum pulsing device 1256 effects complete or nearly complete occlusion of the flow path through the aspiration tube 1202 when the movable member 1206 is in the fully extended position.

Figure 14:
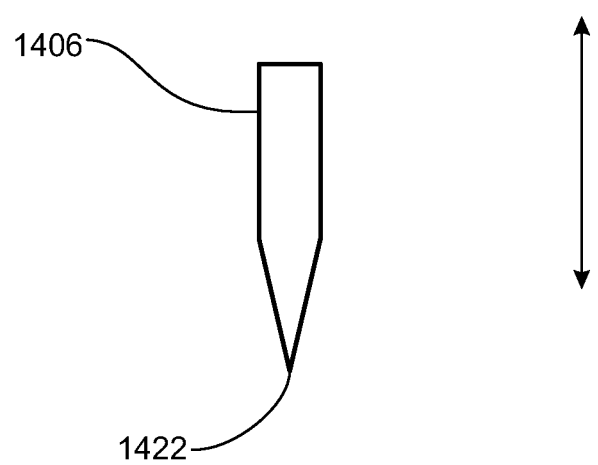
FIG. 14 is a side elevation view of an example of a movable member that may be provided in a vacuum pulsing device.

FIG. 14 is a side elevation view of a movable member 1406 from a perspective transverse to the direction of fluid flow in an aspiration tube. The movable member 1406 may be provided in a solenoid-based vacuum pulsing device such as described above in conjunction with FIGS. 10 and 11 or FIGS. 12 and 13. In this example, the movable member 1406 tapers down to a sharp edge 1422. By this configuration, the movable member 1406 may be utilized to further break up any tissue flowing through the aspiration tube while the movable member 1406 is being cycled into the aspiration tube.

Figure 15:
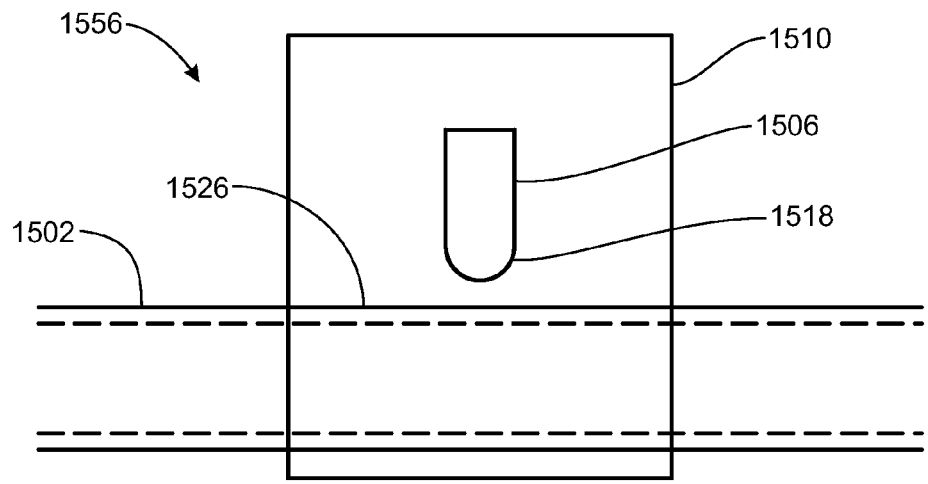
FIG. 15 is a cross-sectional view of another example of a vacuum pulsing device with a movable member thereof in a retracted position.
Figure 16:
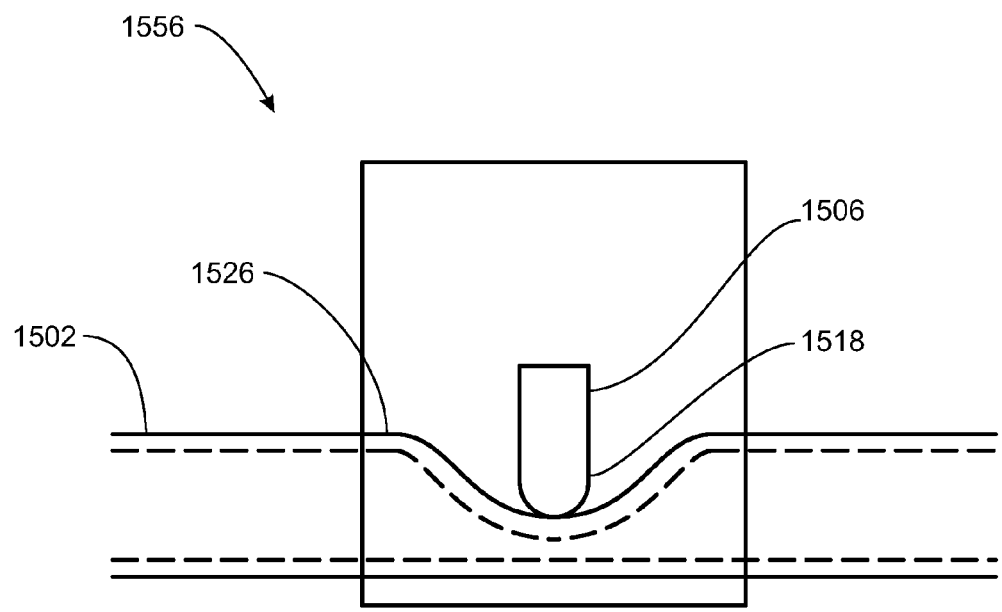
FIG. 16 is a cross-sectional view of the vacuum pulsing device illustrated in FIG. 14, with the movable member in its extended position.

FIGS. 15 and 16 are cross-sectional views of another example of a solenoid-based vacuum pulsing device 1556. The vacuum pulsing device 1556 includes a solenoid actuator 1510 and a movable member 1506 reciprocated by the actuator 1510 toward and away from the flow path of an aspiration tube 1502 of the tissue removal device 104. FIG. 15 illustrates the movable member 1506 in its retracted position and FIG. 16 illustrates the movable member 1506 in its extended position. In this example, the vacuum pulsing device 1556 is designed as a pinch valve. The movable member 1506 includes a distal section 1518 having a rounded end. A section 1526 of the aspiration tube 1502 immediately underneath the movable member 1506 is constructed from a deformable material (e.g., flexible tubing). As the movable member 1506 is translated to its fully extended position, the movable member 1506 comes into contact with the outside surface of the flexible section 1526 and deforms the flexible section 1526 until opposing regions of the inner wall of the flexible section 1526 come into contact with each other, thereby pinching off the flow path through the aspiration tube 1502.

Referring back to FIG. 1, the vacuum pump 108 generally includes a housing, a fluid inlet, a fluid outlet, and vacuum-generating components (not shown). The fluid inlet may be placed in fluid communication with the tissue removal device 104 via the (first) external aspiration line 152. The fluid outlet may be placed in fluid communication with the tissue collection site 128 via the outlet line 130. The external aspiration lines 152, 130, 164, 172 may have any suitable fluid-conducting structure (e.g., tubing), may be of any suitable length, and may be either rigid or flexible. The vacuum pump 108 may be any suitable pump for generating a controlled level of vacuum at the distal end 132 of the tissue removal device 104. The magnitude (or level) of vacuum may be set high enough to enable target tissue 120 to be aspirated through the cannula 148, the internal aspiration line 144, the first external aspiration line 152, the vacuum pump 108, the outlet line 130, and to the tissue collection site 128.

In some implementations, the vacuum pump 108 has a dual-cylinder configuration in which a pair of motorized syringe-type pumping units is disposed in the housing. In this case, the vacuum generating components may include a pair of cylinders, a pair of pistons reciprocating in the respective cylinders, and a pair of motors controlling the reciprocal movement of the respective pistons. The internal passages of the vacuum pump 108 may include a pair of inlet passages interconnecting the first aspiration line 152 and the respective cylinders, and a pair of outlet passages interconnecting the respective cylinders and the outlet line 130. Actively controlled valves may be provided in each inlet passage and outlet passage. The pistons are reciprocated at or about 180 degrees out-of-phase with each other. Accordingly, while one piston is executing a suction stroke the other piston is executing a discharge stroke. Consequently, while fluid from the first aspiration line 152 is being drawn into one cylinder, fluid previously drawn into the other cylinder is being discharged into the outlet line 130. In addition, a pair of pressure transducers may be disposed in fluid communication with the respective cylinders to measure the vacuum in each cylinder. An example of this type of dual-cylinder pump is described in U.S. Patent Application Pub. No. 2005/0234394, which is incorporated by reference herein in its entirety.

Continuing with this example, the motors of the vacuum pump 108 are in signal communication with the control console 112 via a motor control signal line 190. The valves are in signal communication with the control console 112 via a valve control signal line 192. The pressure transducers are in signal communication with the control console 112 via a pressure feedback signal line 194. By this configuration, the control console 112 is able to monitor and adjust the respective speeds of the pistons and their relative positions (i.e., relative timing or phasing), switch the positions of the valves between ON and OFF positions and possibly intermediate positions between the ON and OFF positions, and monitor the vacuum levels in each cylinder so as to make control decisions based on measured vacuum levels. By this configuration, the control console 112 is able to synchronize the respective operations of the motors and valves to maintain a constant vacuum level in the aspiration line 152. The vacuum level may be selected by the surgeon by manipulating controls on the control console 112 or the foot control device 116. This configuration also enables the vacuum pump 108 to respond quickly to real-time adjustments to the vacuum level made by the surgeon while minimizing transitory instabilities in the vacuum level caused by changing the vacuum level.

As diagrammatically illustrated in FIG. 1, the control console 112 may include a display 114 for outputting information to the surgeon. The control console 112 may also include a variety of controls or input mechanisms 118 (switches, knobs, keypad, etc.) for enabling the surgeon to input information, set and adjust various operating parameters of the tissue removal system 100 (e.g., vacuum pump(s) 108 and 168, vacuum pulsing device 156, thermal element 176, etc.), and program or adjust the control mechanisms provided by the foot control device 116. The control console 112 also includes electronic hardware (circuitry) and memory for storing software. The circuitry includes interface circuitry for enabling the respective operations of the display 114 and the input mechanisms 118, and for interfacing with the foot control device 116. The circuitry and software are configured for supporting the various functions of the tissue removal system 100. As examples, the circuitry may be configured for monitoring the operations of the vacuum pump(s) 108 and 168, the vacuum pulsing device 156, and the thermal element 176 and sending appropriate control signals to these components. Software may be provided for programming the circuitry for controlling these components in a manner appropriate for the particular tissue removal procedure to be performed. In some implementations, one or both vacuum pump(s) 108 and 168 may be mounted at or within the control console 112. In other implementations, one or both vacuum pump(s) 108 and 168 may be mounted at or within the foot control device 116.

By utilizing the input mechanisms of the control console 112 the surgeon may, as examples, switch the vacuum pump(s) 108 and 168 ON or OFF, set and vary the vacuum level generated by the vacuum pump(s) 108 and 168, switch the vacuum pulsing device 156 ON or OFF, set and vary the pulse frequency of the vacuum pulsing device 156 (thereby also controlling the flow rate of aspirated tissue), set and vary the magnitude of the vacuum pulses, switch the thermal element 176 ON or OFF, set and vary the amount of current fed to (and thereby control the operating temperature of) the thermal element 176, switch the thermal element 176 between a continuous heating mode and a pulsed heating mode, set and vary the frequency and magnitude of pulses of applied heat energy, etc. The control console 112 may also be configured to enable the surgeon to switch between a mode in which the surgeon can control the vacuum pulse rate and vacuum pulse magnitude (or the thermal pulse rate and thermal pulse magnitude) together as a single operating parameter by making a single adjustment, and a mode in which the surgeon can control the vacuum pulses rate and vacuum pulse magnitude (or the thermal pulse rate and thermal pulse magnitude) independently by manipulating two separate input mechanisms. Similarly, the control console 112 may be configured to enable the surgeon to switch between a mode in which the surgeon can control one or more operating parameters of the thermal element 176 together with one or more parameters of the vacuum pulsing device 156, and a mode in which the surgeon can control the operating parameters of the thermal element 176 independently of the operating parameters of the vacuum pulsing device 156.

The control console 112 may also be configured to enable the surgeon to switch the vacuum pulsing device 156 to a single-pulse mode that activates the vacuum pulsing device 156 only momentarily so as to apply a single pulse at a predetermined vacuum pulse magnitude. The single-pulse mode may be useful, for example, in an ophthalmological procedure that calls for creating an entry into the anterior capsule of a patient's eye. In this example, prior to breaking up target tissue, the distal tip of the cannula 148 may be placed into contact with the exterior of the anterior capsule. During this time, the tissue removal device 104 may be operated in the continuous-vacuum mode to assist in bringing the distal tip into contact with anterior capsule. The vacuum pulsing device 156 is then switched to the single-pulse mode, whereby the impact imparted by the single pulse is sufficient to create an entry into the anterior capsule through the thickness of its exterior structure. The distal tip is then inserted through the entry, at which time a tissue removal procedure may be performed. This technique enables the creation of an entry having a size and shape precisely conforming to the size and shape of the cannula 148, thereby providing a superior seal between the anterior capsule and the cannula 148.

The foot control device 116 may be configured for controlling one or more of the same functions controllable by the control console 112, such as those just described. Accordingly, the foot control device 116 may include one or more input mechanisms such as adjustable knobs 122 and depressible foot pedals 126. The foot pedals 126 may include foot switches and/or pivoting foot pedals. Foot switches may be operated to switch components of the tissue removal system 100 between ON and OFF states, or for clicking through incremental adjustments to operating parameters (e.g., selecting a high, medium or low setting for the applied vacuum or electrical energy). Pivoting foot pedals may be utilized to vary operating parameters between minimum and maximum values. The adjustable knobs 122 on the foot control device 116 or those on the control console 112 may be configured to enable the surgeon to set the minimum and maximum values of the pivoting foot pedal, and/or the rate (e.g., linear or exponential) by which an operating parameter changes in response to the pivoting travel of the foot pedal. As an example, pivoting the foot pedal forward from its base position to its halfway position may cause the associated operating parameter to be adjusted to a value that is exactly 50% of the preset maximum value. As another example, pivoting the foot pedal forward from its base position to its halfway position may result in adjusting the associated operating parameter to a value that is 75% of its preset maximum value, in which case adjusting the operating parameter over the other 25% up to the maximum value would require pivoting the foot pedal forward from the halfway position through the remaining portion of the pedal's travel. The control console 112 and/or the foot control device 116 may be configured to enable the surgeon to select which functions or operations are to be controlled by the control console 112 and which functions or operations are to be controlled by the foot control device 116. For simplicity, the foot control device 116 is diagrammatically illustrated in FIG. 1 as communicating with the control console 112 over a wired or wireless communication link 196. It will be understood, however, that depending on the functions controllable by the foot control device 116, various electrical signal lines may run directly to the foot control device 116 as an alternative or additionally to those communicating with the control console 112.

Figure 17:
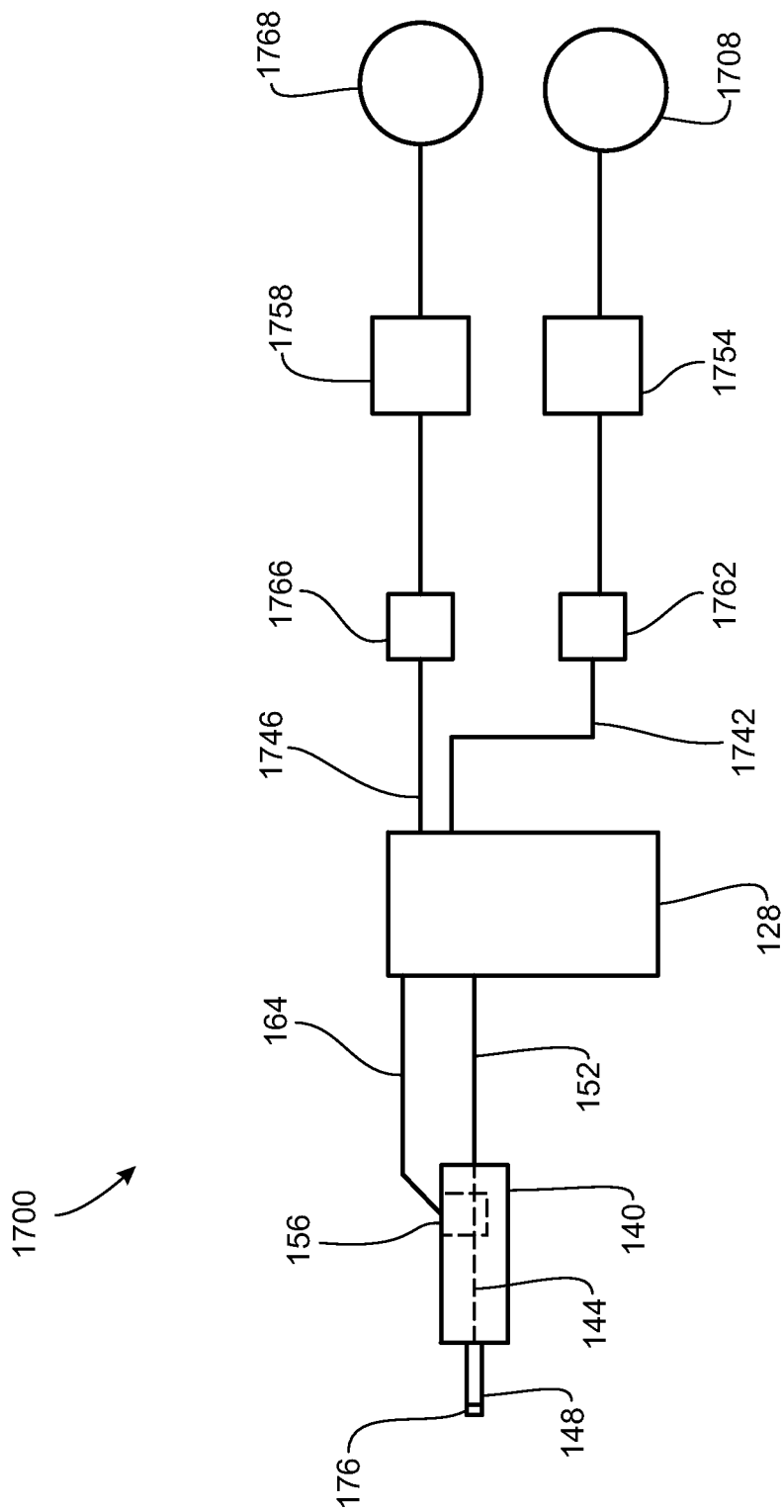
FIG. 17 is a block diagram illustrating an example of a tissue removal system according to another implementation of the present invention.

FIG. 17 is a block diagram illustrating an example of a tissue removal system 1700 according to another implementation. For simplicity, the control console 112 and foot control device 116 (FIG. 1) are not illustrated in FIG. 17. The tissue removal system includes a first vacuum pump 1708 providing adjustable vacuum on the first aspiration line 152 during the continuous vacuum mode, and a second vacuum pump 1768 providing adjustable vacuum at relatively higher levels on the second aspiration line 164 during the pulsed vacuum mode. As noted previously, the vacuum pulsing device 156 or other component of the tissue removal device 104 may be configured for switching the aspiration path from the cannula 148 between the first aspiration line 152 and the second aspiration line 164 in accordance with vacuum mode selected. In this example, the vacuum pumps 1708, 1768 are configured as gas (e.g., air) pumps instead of the liquid pumps described earlier in this disclosure. The tissue collection device 128 is interconnected between the tissue removal device 104 and the vacuum pumps 1708, 1768 via the aspiration lines 152, 164 and respective outlet lines 1742, 1746. The tissue collection device 128 may be configured in a conventional manner for removing aspirated fluid and tissue such that only gas is routed through the outlet lines 1742, 1746. Alternatively, separate tissue collection devices may be provided for the two aspiration lines 152, 164. Typically, vacuum reservoirs 1754, 1758 are provided upstream of the respective vacuum pumps 1708, 1768 to assist in building vacuum. Alternatively, both vacuum pumps 1708, 1768 may communicate with a single vacuum reservoir. One or more pressure regulators 1762, 1766 of any suitable design may be provided in fluid communication with the respective vacuum pumps 1708, 1768 as needed. The pressure regulators 1762, 1766 may be of the type that can be controlled by the control console 112 or the foot control device 116. One or more of the foregoing components (vacuum pumps 1708, 1768, vacuum reservoirs 1754, 1758, pressure regulators 1762, 1766, tissue collection device 128) may be mounted at or within the control console 112 or the foot control device 116. The tissue removal system 1700 illustrated in FIG. 17 may operate in a manner similar to that described above for the tissue removal system 100 illustrated in FIG. 1.

Figure 18:
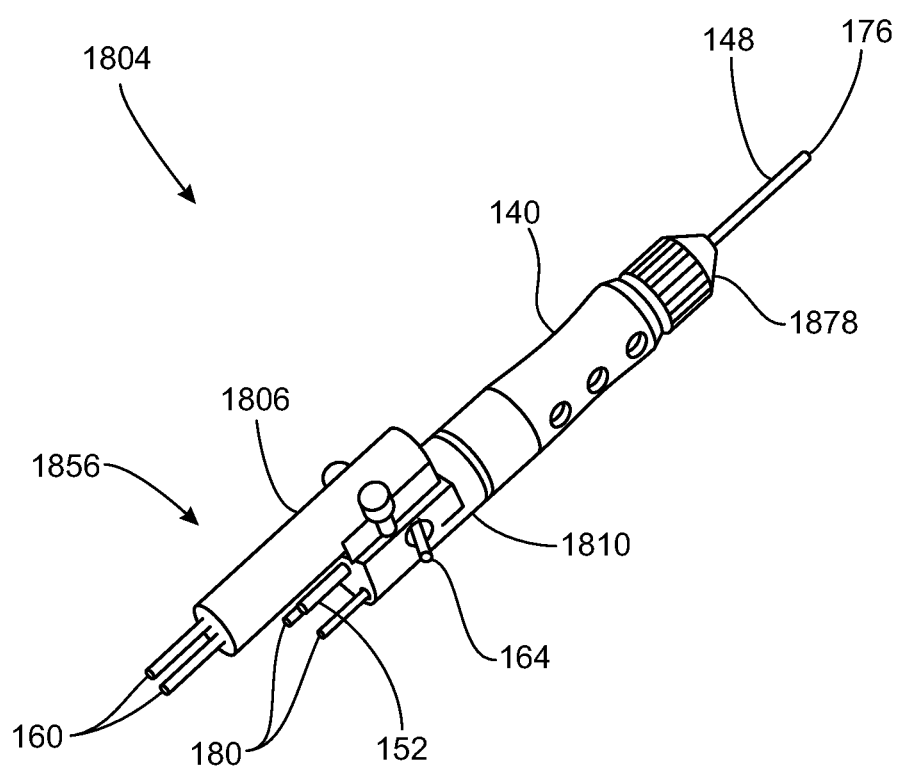
FIG. 18 is a perspective view of an example of a tissue removal device according to another implementation of the present invention.
Figure 19:
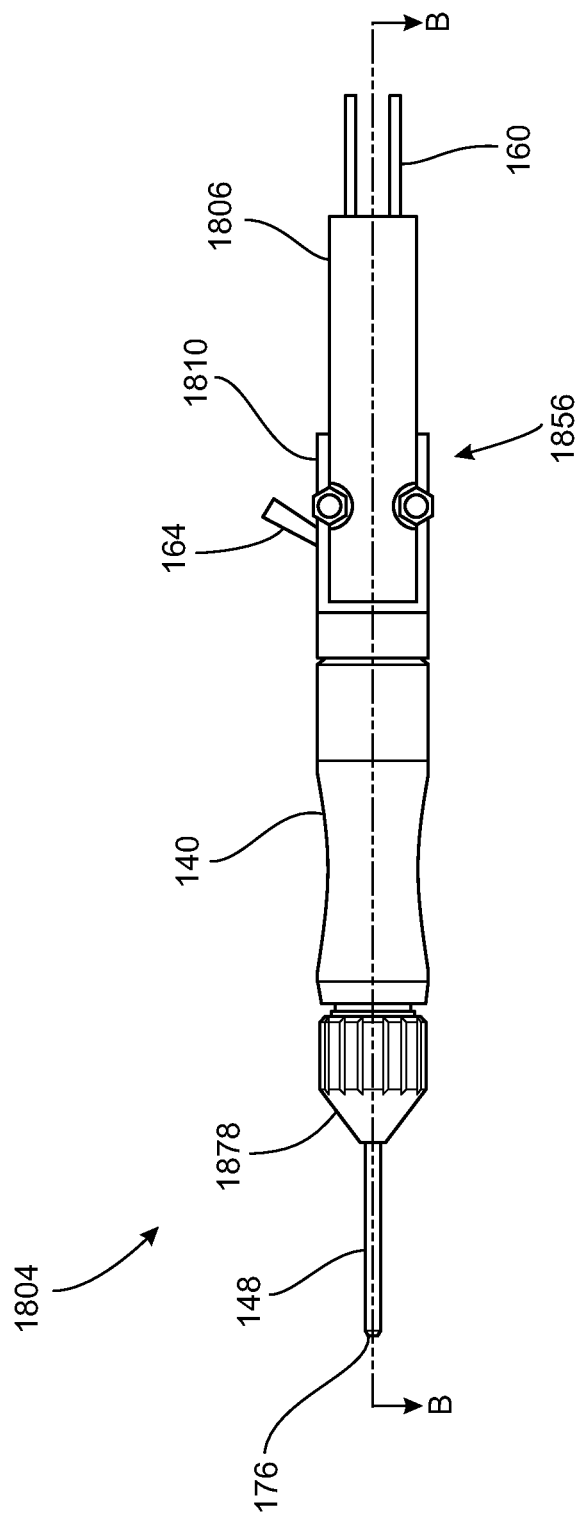
FIG. 19 is a top plan view of the tissue removal device illustrated in FIG. 18.
Figure 20:
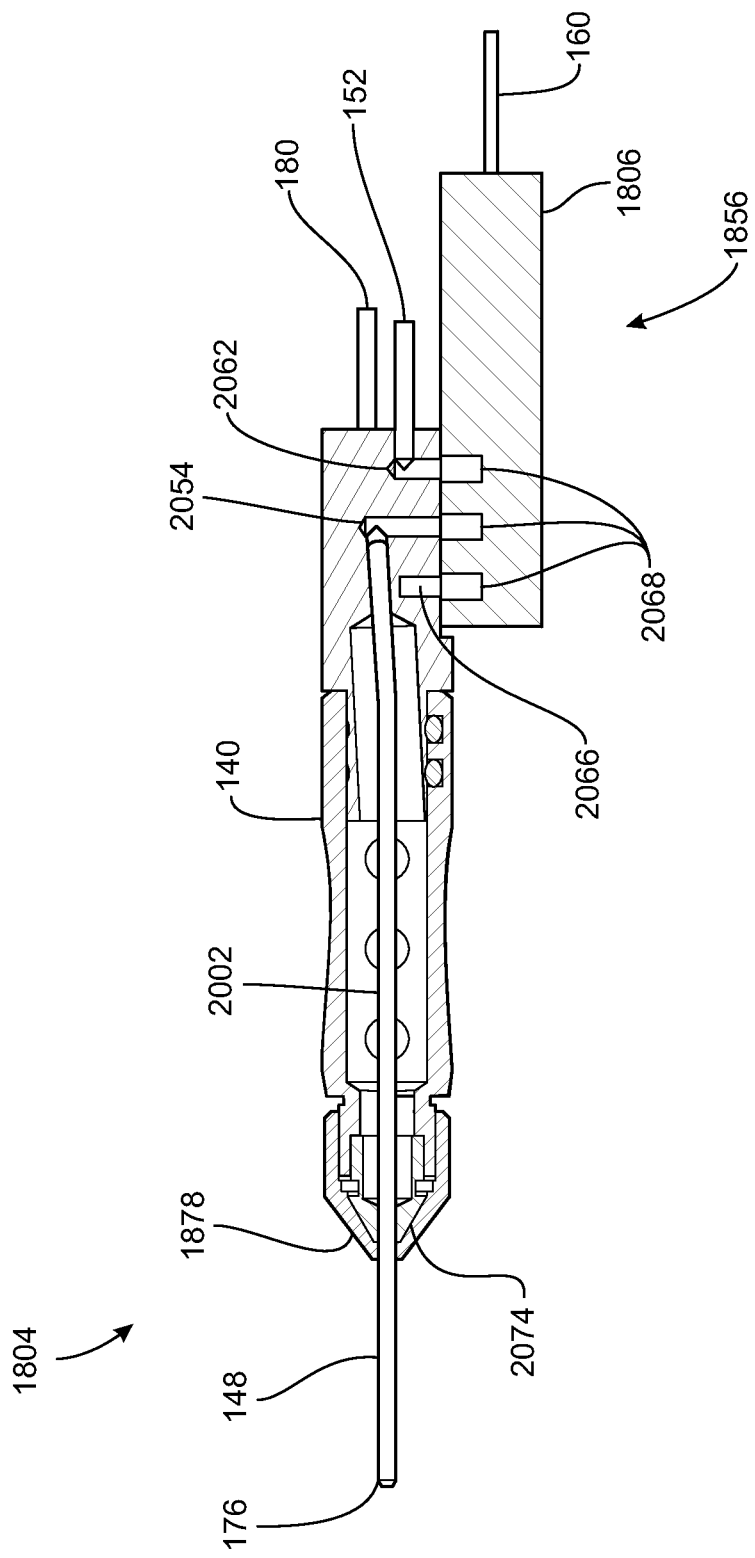
FIG. 20 is a cross-sectional view of the tissue removal device taken along line B-B of FIG. 19.

FIGS. 18, 19 and 20 illustrate an example of a tissue removal device 1804 according to another implementation. Specifically, FIG. 18 is a perspective view of the tissue removal device 1804, FIG. 19 is a top plan view of the tissue removal device 1804, and FIG. 20 is a cross-sectional view of the tissue removal device 1804 taken along line B-B of FIG. 19. In this example and as described earlier, the tissue removal device 1804 is configured for operation with two aspiration lines 152, 164 extending from proximal openings of the housing 140, in which one aspiration line 152 is utilized during the continuous vacuum mode and the other aspiration line 164 is utilized during the pulsed vacuum mode. Alternatively, the tissue removal device 1804 may be configured for operation with only a single aspiration line. In this example, the cannula 148 is connected to an internal aspiration tube 2002 within the housing 140. The cannula 148 may have the split design described earlier in this disclosure, with structural halves of the cannula 148 connected to respective insulated wires that run through the housing 140 to respective outbound wires serving as the heating signal line 180. The cannula 148 may extend outward from a distal opening of the housing 140 formed by an internal hub 2074 and a coaxial, threaded locking mechanism 1878 to enable quick assembly and disassembly of the tissue removal device 1804.

Also in the example illustrated in FIGS. 18, 19 and 20, the tissue removal device 1804 includes a solenoid-based vacuum pulsing device 1856. The vacuum pulsing device 1856 includes a solenoid block 1810 attached to the proximal end of the housing 140 and a solenoid actuator 1806. The solenoid block 1810 includes a common port 2054 in fluid communication with the internal aspiration tube 2002, a low-vacuum port 2062 in fluid communication with the first aspiration line 152, and a high-vacuum port 2066 in fluid communication with the second aspiration line 164. The actuator 1806 may be provided in the form of a spool valve, the general operation of which is known to persons skilled in the art. In this case, the movable member that is actuated by the actuator 1806 is a spool that translates back and forth relative to the solenoid block 1810. The position of the spool determines whether the common port 2054 is in fluid communication with either the low-vacuum port 2062 or the high-vacuum port 2066, by means of interconnecting passages or channels 2068 that are active or inactive depending on the spool position. The spool is thus utilized to switch the tissue removal device 1804 between the continuous vacuum mode and the pulsed vacuum mode. In the continuous vacuum mode, the common port 2054 is in fluid communication with the low-vacuum port 2062 and aspirated material is routed from the cannula 148 to the first aspiration line 152 under the influence of the first vacuum pump. In the pulsed vacuum mode, the common port 2054 is in fluid communication with the high-vacuum port 2066 and aspirated material is routed from the cannula 148 to the second aspiration line 164 under the influence of the second vacuum pump. In this example, the vacuum pulsing device 1856 may be configured to generate vacuum pulses by rapidly translating the spool back and forth so as to alternately open and close the fluid path between the common port 2054 and the high-vacuum port 2066.

Figure 21:
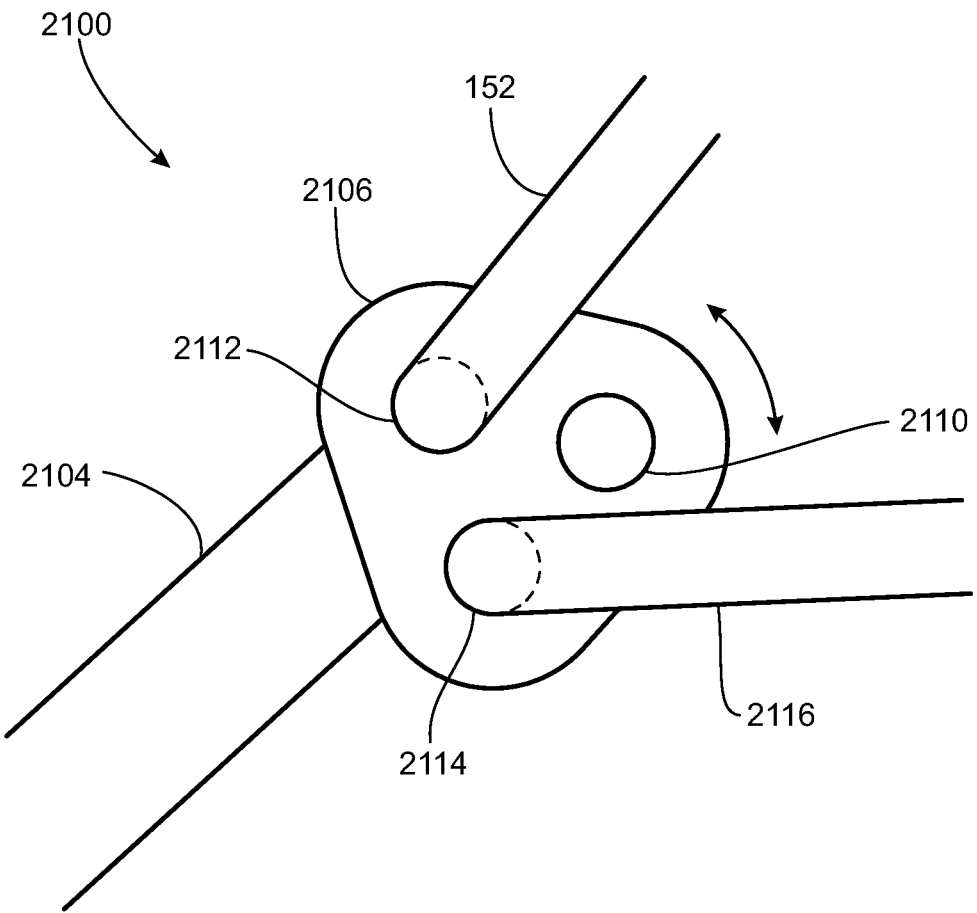
FIG. 21 is a perspective view of an example of a hand-held surgical instrument according to another implementation of the present invention.

FIG. 21 is a perspective view of example of a hand-held surgical instrument 2100 according to another implementation. The surgical instrument 2100 is configured as a multi-function instrument in which one or more functions in addition to tissue aspiration may be selected by the surgeon. For this purpose, the surgical instrument 2100 includes a rotatable hub 2106 located at its proximal end. The rotatable hub 2106 may be rotated by the surgeon about a pivot 2110 supported by the surgical instrument 2100. The rotatable hub 2106 includes a vacuum port or bore 2112 connectable to vacuum tubing 152 and one or more additional ports or bores 2114 connectable to corresponding additional tubing 2116. The additional ports 2114 may be utilized as injection bores for adding specific types of materials to the surgical site as noted previously in this disclosure, by flowing such materials through the surgical instrument 2100 and the same cannula utilized for tissue aspiration. The interface between the rotatable hub 2106 and the surgical instrument 2100 is configured such that incremental rotation locks a desired port 2112 or 2114 into fluid communication with the internal passages of the surgical instrument 2100 normally employed for vacuum application and fluid and tissue flow. In one implementation, the additional port 2114 and tubing 2116 are utilized for injecting liquid IOL material as part of an endocapsular procedure. After the vacuum port 2112 has been employed to remove a cataract, the surgeon rotates the hub 2106 to switch in the additional port 2114 that is connected to a source of IOL material. The surgeon then utilizes the surgical instrument 2100 to inject the liquid IOL material into the capsular bag of the eye via the tubing 2116 that serves as the IOL material supply line. This configuration avoids requiring the surgeon to remove the vacuum cannula from the eye and subsequently insert—through the previously created, small anterior capsule incision—another separate cannula for the purpose of injecting the liquid IOL material. This is advantageous because in order to perform the endocapsular procedure, the incision made in the anterior capsule must perfectly match the cannula being utilized. Any movement of the cannula might tear or damage the incision, which would compromise the incision and make it more difficult to seal the incision to prevent the liquid IOL material from leaking out from the capsular bag.

Figure 22:
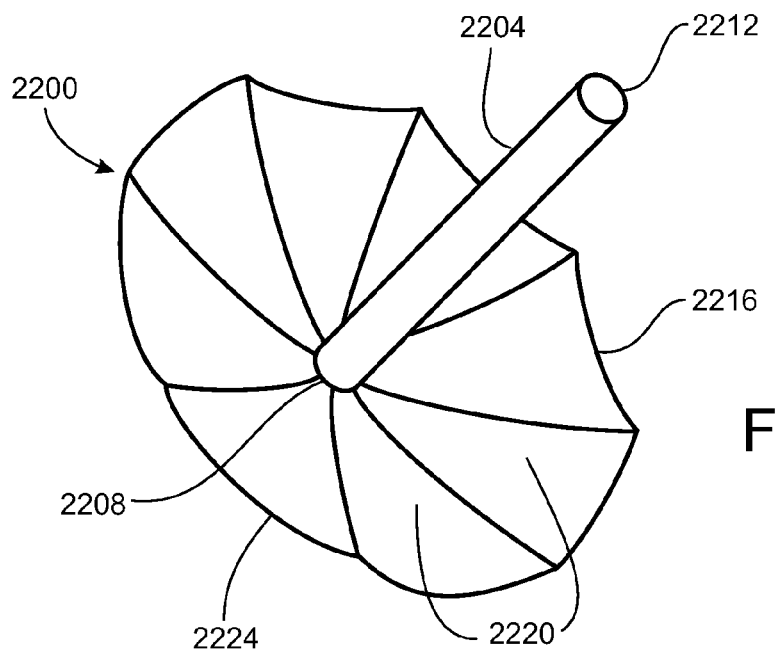
FIG. 22 is a perspective view of an example of an expandable incision seal according to an implementation disclosed herein, with the seal in an expanded position.
Figure 23:
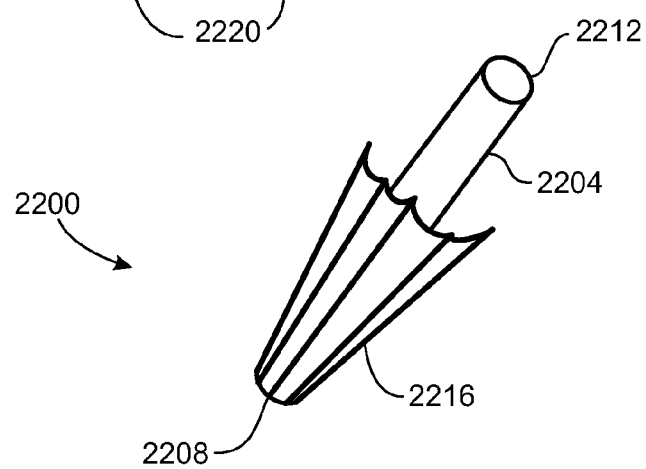
FIG. 23 is a perspective view of the expandable seal illustrated in FIG. 22, with the seal in a retracted position.

FIGS. 22 and 23 are perspective views of an example of an expandable incision seal 2200 that may be utilized to seal an incision made during an endocapsular procedure or other type of procedure. FIG. 22 shows the incision seal 2200 in an expanded position, while FIG. 23 shows the incision seal 2200 in a retracted position. The incision seal 2200 includes a shaft 2204 sized to fit into and completely fill the opening defined by an incision. The shaft 2204 includes a distal end 2208 and a proximal end 2212. The incision seal 2200 also includes an expandable portion 2216 adjoining the distal end 2208. The expandable portion 2216 is configured in the manner of an umbrella. Accordingly, the expandable portion 2216 includes a plurality of radial segments or panels 2220 extending outward in radial directions from the distal end 2208, with adjacent segments 2220 being adjoined at radial fold lines 2224. The expandable portion 2216 is movable from the retracted position shown in FIG. 23 at which the segments 2220 are oriented at a first angle relative to the shaft 2204, to the expanded position shown in FIG. 22 at which the segments 2220 are disposed at a second angle relative to the shaft 2204 greater than the first angle. In addition to functioning as a seal, the incision seal 2200 may be utilized as a plunger to push viscous materials through a tissue removal device or other surgical instrument (e.g., the surgical instrument 2100 shown in FIG. 21) and into the surgical site.

In the example of an IOL procedure, the incision seal 2200 may initially be lightly (or loosely, etc.) attached at its proximal end 2212 to an elongated rod or wire of a separate instrument. The proximal end 2212 may be configured by any suitable means to effect this attachment. With the surgical instrument 2100 set such that the IOL material line 2116 (FIG. 21) fluidly communicates with the cannula of the surgical instrument 2100, the surgeon injects the IOL material into the IOL material line 2116. With the shaft 2204 of the incision seal 2200 attached to the rod of the separate instrument, the surgeon may then insert the incision seal 2200 into the IOL material line 2116 and push the incision seal 2200 therethrough by pushing the rod of the separate instrument. The incision seal 2200 easily travels through the IOL material line 2116 in the retracted position shown in FIG. 23. The IOL material may be highly viscous and require assistance in being inserted through the incision into the capsular bag. Accordingly, the distal end 2208 may be utilized to push the IOL material through the IOL material line 2116. The surgeon may push the incision seal 2200 through the cannula of the surgical instrument 2100 and into the incision. The surgeon may push the incision seal 2200 far enough through the incision that the expandable portion 2216 clears the incision and is disposed completely in the capsular bag. At this time, the shaft 2204 of the incision seal 2200 extends through the incision and the tissue boundary defining the incision fits tightly around the shaft 2204. The surgeon may then pull on the rod of the separate instrument whereby the shaft 2204 begins to retract out from the incision. This pulling causes the expandable portion 2216 of the incision seal 2200 to expand outwardly to the expanded position shown in FIG. 22. In the expanded position, the expandable portion 2216 abuts against the posterior surface of the anterior capsule in the vicinity surrounding the incision. The shaft 2204 and the expandable portion 2216 thus form a fluid-tight seal in and around the incision. Moreover, because the expandable portion 2216 is now in its expanded position and is located on the inner side of the incision, the expandable portion 2216 cannot be removed from the anterior capsule and consequently the shaft 2204 cannot be completely retracted from the incision because the expandable portion 2216 remains anchored to the shaft 2204. However, as noted above the rod of the separate instrument is merely lightly attached to the shaft 2204. Hence, when the surgeon pulls back on the rod, the rod is detached from the shaft 2204 and then may be easily removed from the surgical site via retraction through the cannula of the surgical instrument 2100 after the incision seal 2200 has been properly installed in the incision in the manner just described.

The expandable incision seal 2200 may be constructed from any materials suitable for enabling the functions and operations described above in conjunction with FIGS. 22 and 23.

Figure 24A:
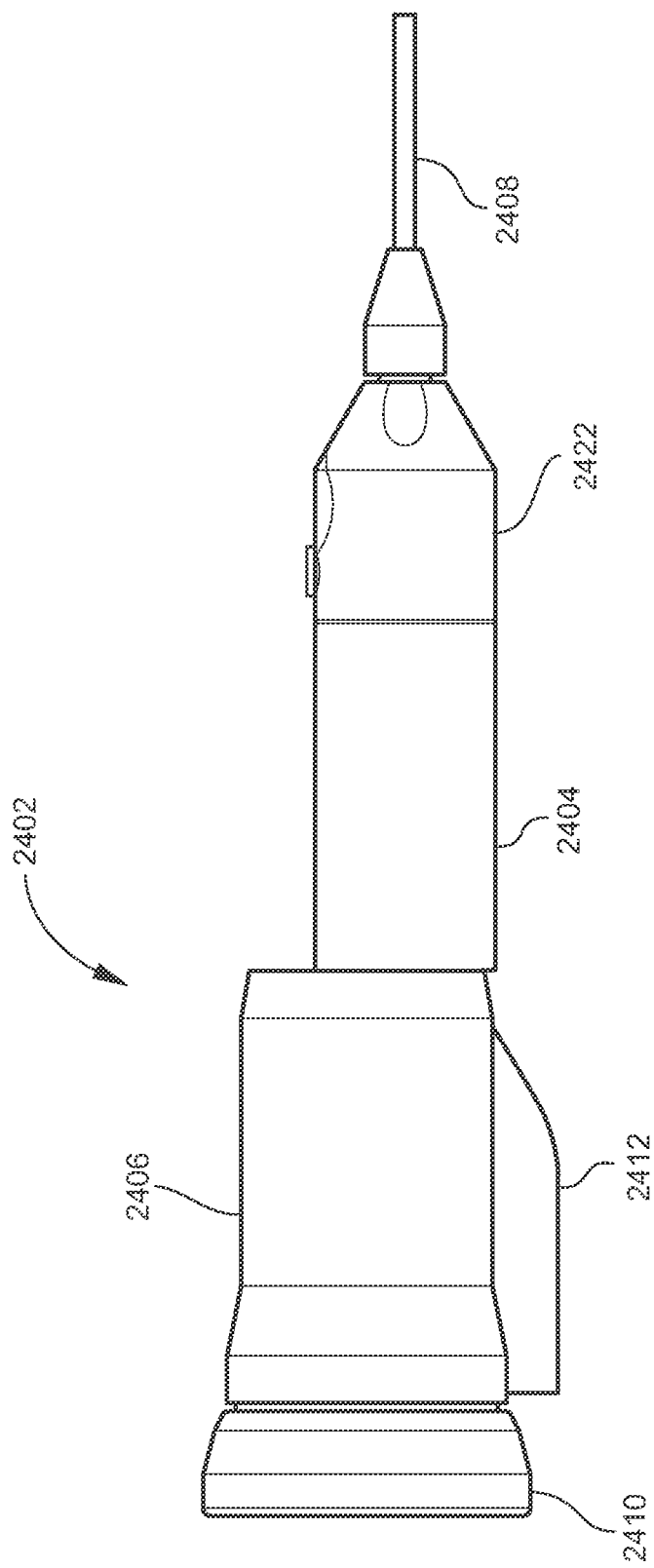
FIG. 24A is an inverted side view of an example of a tissue removal device according to yet another implementation of the present invention.
Figure 24B:
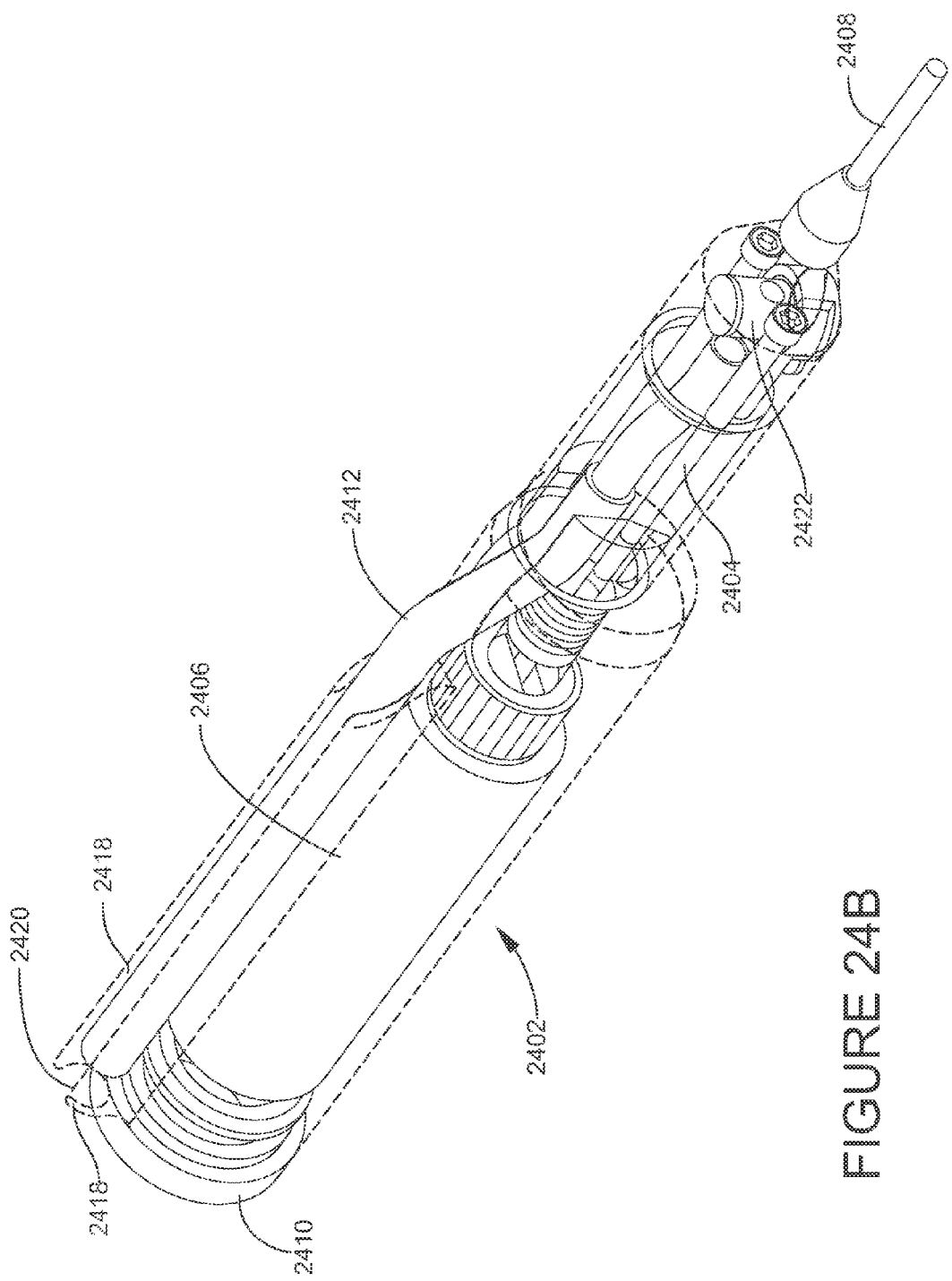
FIG. 24B is a perspective view of another example of a tissue removal device according to an implementation of the present invention.
Figure 25:
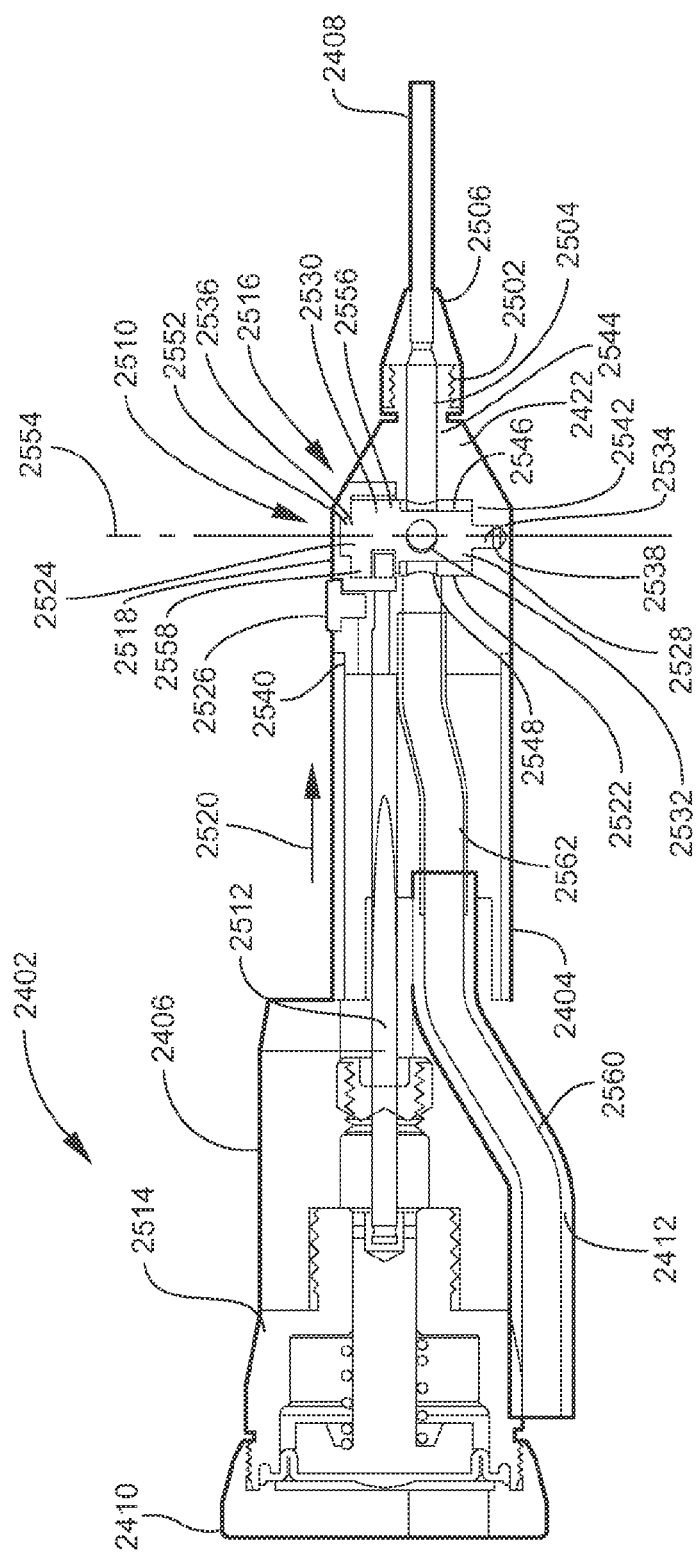
FIG. 25 is a cross-sectional view of the tissue removal device illustrated in FIG. 24A.
Figure 26:
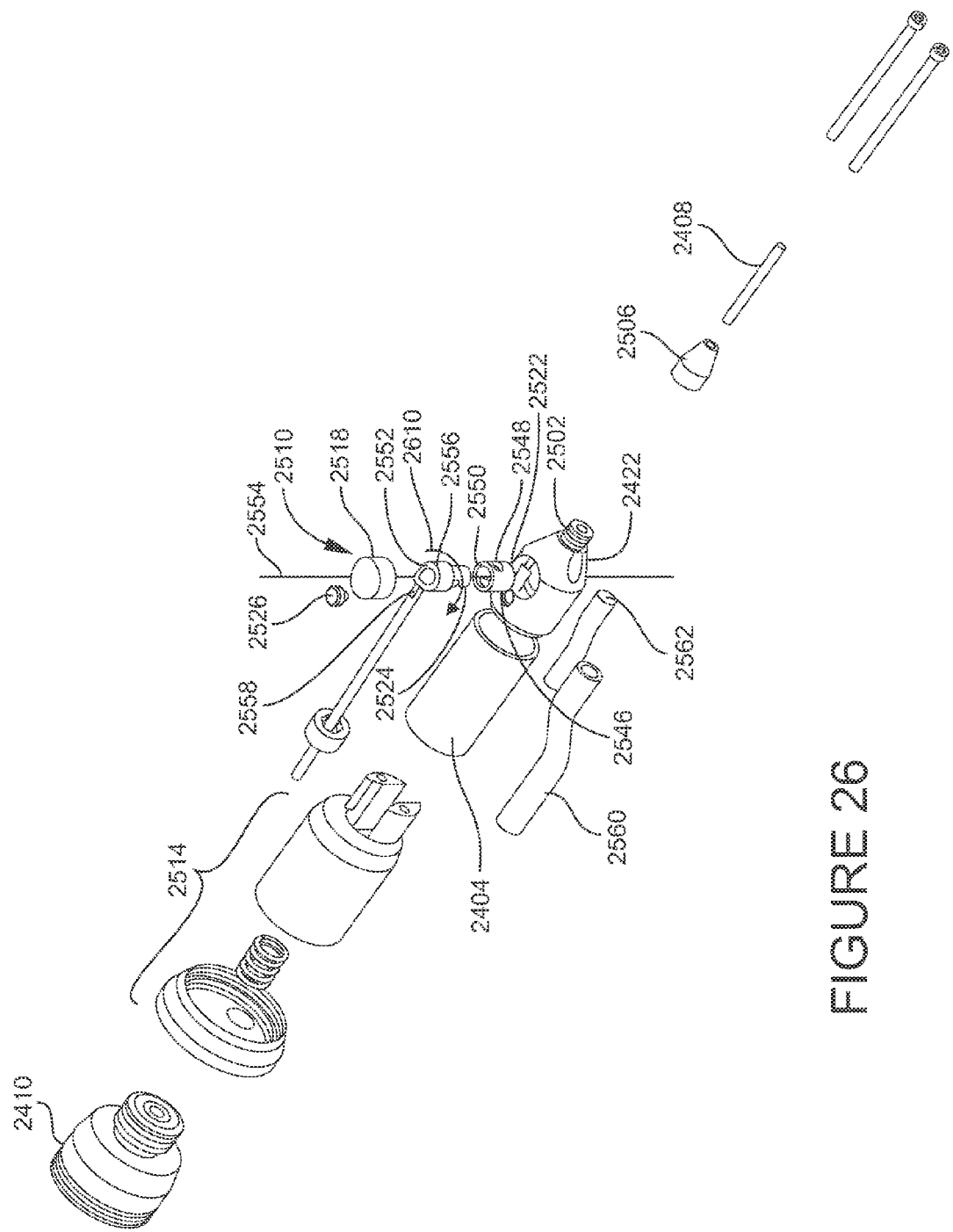
FIG. 26 is an exploded perspective view of the tissue removal device illustrated in FIG. 24A featuring the components of the rotary valve assembly.

FIGS. 24A, 24B, 25 and 26 illustrate other examples of a tissue removal device 2402 according to implementations of the present invention. Specifically, FIG. 24A is a side view of the tissue removal device 2402, FIG. 24B is a perspective view of a second implementation of the tissue removal device 2402, FIG. 25 is a cross sectional view of the tissue removal device 2402, and FIG. 26 is an exploded perspective view the tissue removal device 2402. The tissue removal device 2402 described in these exemplary implementations may be used in any implementation of a tissue removal system in accordance with the teachings of the present invention, including the tissue removal system 100 described in FIG. 1.

In the illustrated example, the tissue removal device 2402 generally includes an elongated off-center construction having a central housing 2404, an actuator housing 2406, and an end cap 2422 having a threaded tip 2502 formed at a distal end of the end cap 2422. As used herein, an "off-center construction" refers to a construction where the centerline of the central housing 2404 is offset vertically from the centerline of the actuator housing 2406. As shown, a cannula 2408 may be fastened to the central housing 2404 at the threaded tip 2502 and the tissue removal device 2402 may further include an end cap 2410 for enclosing the actuator housing 2406 at its proximal end.

The central housing 2404 may include an annular construction having a hollow interior with dimensions sufficient to house one or more aspiration lines passing to the cannula 2408. The actuator housing 2406 may likewise include an annular construction having a partially-closed distal end and a hollow interior with dimensions sufficient to house a linear actuator or other drive mechanism. In some implementations, the central housing 2404 may be detachably coupled to the actuator housing 2406 by, for example, mating threaded members. In other implementations, the central housing 2404 may be integrally formed with or welded, soldered, bonded, or otherwise permanently attached to the actuator housing 2406.

The end cap 2422 may include a generally solid cylindrical body having a tapered and threaded distal end 2502. The end cap 2422 may also include at its proximal end an annular seat 2540 that is configured to mate with a distal end of the central housing 2404. The end cap 2422 may be constructed of a material that is both electrically and thermally insulating such as, for non-limiting examples, thermoplastics and other polymeric compositions.

In this example, the tissue removal device 2402 is configured for operation with one aspiration line 2412 extending from an opening 2414 formed at the distal end of the actuator housing 2406. Alternatively, the tissue removal device 2402 may be configured for operation with two aspiration lines, in which one aspiration line may be utilized during the continuous vacuum mode and the other aspiration line may be utilized during the pulsed vacuum mode.

In the implementation shown in FIG. 24B, the aspiration line 2412 may be secured to actuator housing 2406 by an elongated retaining member 2416 coupled to the outer surface of the actuator housing 2406. The retaining member 2416 may include a C-shaped construction having a pair of retaining ends 2418 that form a circular channel 2420 for passing the aspiration line 2412 from the central housing 2404.

In some implementations, the retaining member 2416 may be integrally formed with the actuator housing 2406. In other implementations, the retaining member 2416 may be a separate part that attaches to and detaches from the actuator housing 2406 or, alternatively, the retaining member 2416 may be permanently secured to the actuator housing 2406 by, for example, welding, soldering, an adhesive, or other securing means. In some implementations, the retaining member 2416 may be constructed of the same material as the actuator housing 2406, especially in implementations where the retaining member 2416 is integrally formed with or permanently attached to the actuator housing 2406. In other implementations, the retaining member 2416 may be constructed of a resilient material to enable the aspiration line 2412 to be "snap-fitted" into the channel 2420.

In this example, as best shown in FIG. 25, the cannula 2408 is connected to an internal aspiration tube 2504 within the central housing 2404. The cannula 2408 may include a cannula tip with one or more thermal elements incorporating any one of the cannula tip designs previously described in this disclosure. As discussed above, the cannula 2408 may be fastened to threaded end 2502 of the central housing 2404 at its hub 2506, which includes a coaxial, threaded locking mechanism to enable quick assembly and disassembly of the tissue removal device 2402.

Also in the example illustrated in FIGS. 25 and 26, the tissue removal device 2402 includes an actuator-driven vacuum pulsing device 2510 (also referred to herein as a pulsating gate) coupled to the internal aspiration tube 2504. In this example, the pulsating gate 2510 may include an actuator rod 2512 coupled between an actuator 2514 and a rotary valve assembly 2516.

As shown, the actuator rod 2512 may include an elongated rod that extends through the hollow interior of the central housing 2404. The actuator rod 2512 may be made of non-corrosive material, such as stainless steel or other suitable material. The actuator rod 2512 may be coupled to actuator 2514 at one end by conventional means, for example by a pivot pin, and supported in a cantilevered fashion at an opposite distal end by a valve cap 2518 coupled to a distal end of the central housing 2404. The valve cap 2518 may include a cap-shaped design having a slot (not shown) formed in a rearward face of the valve cap 2518 for allowing the distal end of the actuator rod 2512 to extend therethrough and, further, translate in a linear direction 2520 when actuated by the actuator 2514.

The actuator 2514 may be stored in the actuator housing 2406 and, further, may include, for example, a pneumatic, hydraulic, or electro-mechanical linear motion actuator. In other implementations, the actuator 2514 may be directly coupled to the central housing 2404. In the non-limiting example shown in FIGS. 24, 25 and 26, the actuator 2514 includes a (push-type) pneumatic linear solenoid actuator. In operation, the actuator 2514 is configured to translate the distal end of the actuator rod 2512 towards the rotary valve assembly 2516 such that the actuator rod 2512 engages a rotary valve of the rotary valve assembly 2516. As will be discussed in further detail below, when the actuator rod 2512 engages the rotary valve, the rotary valve is configured to obstruct all or part of the fluid path of the internal aspiration tube 2504, such that the cyclical rotation of the rotary valve generates vacuum pulses and alters the flow rate and volume of fluid passing through the aspiration line 2412. In some implementations, the actuator 2514 may be in electrical communication with the control console 112 and/or the foot-operated control device 116. In these instances, the frequency of the actuator rod's 2512 linear translation may be controlled by computer software operating the control console 112 and/or by operating the foot-operated control device 116.

Turning now to the rotary valve assembly 2516, as best illustrated in FIGS. 25 and 26, the valve assembly 2516 may include a valve connector 2522, a rotary valve 2524, the valve cap 2518, and a valve key 2526 for securing the valve cap 2518 within in the end cap 2422. In the example shown, the valve connector 2522 may include an annular body having annular sidewalls 2546, a hollow interior 2604, and an aperture 2548 extending through the annular sidewalls 2546 of the body. The valve connector 2522 is retained within a hollowed-out portion 2542 formed in the end cap 2422. The valve connector 2522 is configured to rest within the hollowed-out portion 2542 such that the aperture 2548 is aligned within a passage 2544 extending through the end cap 2422 for passing the internal aspiration tube 2504.

In this example, the rotary valve 2524 includes a body 2528 and a teardrop shaped lobe 2530. The body 2528 is a solid cylindrical member configured to be received by and rotatable within the interior 2604 of the valve connector 2522. The body 2528 includes an orifice 2532 extending therethrough. The lobe 2530 acts as a camming element for rotating the rotary valve 2524 within the valve connector 2522. The lobe 2530 includes a base circle or heel 2556 and a flank 2558. The diametrical dimensions of the heel 2556 may be greater than the diameter of the body 2528 such that a top annular surface 2550 of the valve connector 2522 acts as a bearing surface for the lobe 2530. The lobe 2530 is further designed to confine and concentrically align the orifice 2532 with the valve connector aperture 2548.

The rotary valve 2524 may further include a bottom pin 2534 and a top pin 2536. In this example, the bottom pin 2534 extends from a bottom surface of the body 2528 into a circular notch 2538 formed in the end cap 2422. The top pin 2536 extends from a top surface of the lobe 2530 into a circular notch 2552 formed in the underside of the valve cap 2518. The bottom and top pins 2534, 2536 define a pivot axis 2554 about which the rotary valve 2524 may rotate between a first position to a second position, as will be discussed in further detail below.

In operation, vacuum pulses may be generated by repetitive movement of the rotary valve 2524. In this example, the actuator 2514 is configured to translate the actuator rod 2512 in the linear direction 2520. As the actuator rod 2512 is translated it engages the flank 2558 of the lobe 2530, which causes the rotary valve 2524 to rotate, in the present example counterclockwise along 2610, about the pivot axis 2554 between a first (open) position and a second (closed) position. The rotary valve 2524 is designed such that, in the open position, the orifice 2532 in the rotary valve 2524 is aligned in fluid communication with the aperture 2548 in the valve connector 2522, thereby enabling fluid to flow freely through the internal aspiration tube 2504. The rotary valve 2524 is further designed such that, in the closed position, the orifice 2532 is rotated approximately 90°, thereby interrupting the fluid flow through the internal aspiration tube 2504.

In some implementations, the rotary valve assembly 2516 may include a "fail-safe" design. In these implementations, the rotary valve 2524 may be biased by a spring (i.e., spring-loaded) towards the open position. Thus, the actuator rod 2512 must apply enough force to the flank 2558 to overcome the force of the spring. Once the force applied to the flank 2558 is discontinued, the rotary valve 2524 is returned to its open position. In this example, vacuum pulses are generated by the repetitive movement of the rotary valve 2524 against the spring bias, between the open and closed positions. In this way, the vacuum pulsing device 2510 is adapted to generate vacuum pulses by rapidly applying and releasing the force applied to the lobe flank 2558 against the spring bias so as to alternately open and close the fluid path in the internal aspiration tube 2504.

In some implementations, the valve assembly 2516 may also be hermetically sealed to prevent fluid from leaking from the aspiration line 2412 and, therefore, reducing the vacuum pressure. In some implementations, all of the components of the rotary valve assembly 2516 may be made from non-corrosive material including, as non-limiting examples, plastic, ceramic, stainless steel, or any other suitable material. In further implementations, the orifice 2532 may include sharpened outer edges to break up any tissue flowing through the rotary valve 2524 while the rotary valve 2524 is being cycled between the open and closed positions. In yet further implementations of the present invention, the valve cap 2518 may include a stop for limiting the rotation of the rotary valve 2524.

The exemplary rotary valve 2524 described herein is non-limiting. Persons skilled in the art will appreciate that other rotary valve devices and configurations may be used without departing from the broad aspects of the present teachings.

As best shown in FIG. 25, the aspiration line 2412 may include multiple tube sections. In this example, the aspiration line 2412 may include an external aspiration tube 2560, the internal aspiration tube 2504, and an intermediate aspiration tube 2562 coupled between the internal aspiration tube 2504 and the external aspiration tube 2560. As discussed above, the internal aspiration tube 2504 is coupled at its distal end to the cannula 2408, and extends therefrom through the end cap 2422 where its proximal end is coupled to the intermediate aspiration tube 2562. As shown, in some implementations, the vacuum pulsing gate 2510 may be coupled to the internal aspiration tube 2504. In other implementations, the vacuum pulsing gate 2510 may be coupled to other sections of the aspiration line 2412. In further implementations, the vacuum pulsing gate 2510 include a coupling for adjoining sections of the aspiration line 2412. In this example, the external aspiration tube 2560 communicates with the vacuum pump 108 and is coupled at its distal end to the intermediate aspiration tube 2562. In some implementations, adjoining tube sections may be coupled together by press fit, friction fit, medical grade adhesive, or any other suitable means.

While the aspiration line 2412 is described herein as including three tube sections, persons skilled in the art will appreciate that four or more tube sections and other tube couplings may be used without departing from the broad aspects of the present teachings.

Figure 27:
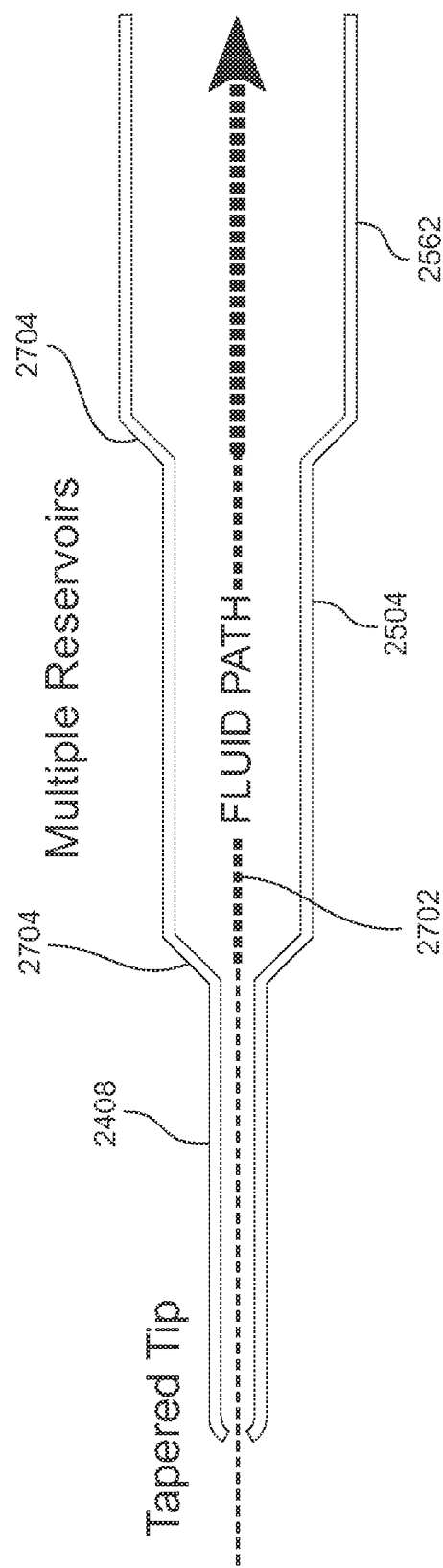
FIG. 27 is a schematic view of the fluid path flow of the tissue removal device illustrated in FIG. 24A featuring an example of an expanding aspiration line configuration.

In some implementations, as best illustrated in FIG. 27, the tip of the cannula 2408 may be tapered to not only break up the tissue passing through the cannula 2408, but also to increase the back pressure inside of the aspiration line 2412. In addition to tapering the cannula 2408 tip, in some implementations, the internal diameter of adjoining tube sections (e.g., the internal aspirating tube 2504 and the intermediate aspiration tube 2562) of the aspiration line 2412 may be increased along its fluid path 2702 to increase or "supercharge" the vacuum fluid flow. Under the laws governing fluid dynamics, including the Bernoulli's principle and the principle of continuity, a fluid's velocity must decrease as it is expanded, while its pressure must increase to satisfy the principle of conservation of energy. Applying these principles to the present invention, the vacuum pressure in the aspiration line 2412 may be increased due to the successive expansion of the aspiration line 2412 tube sections. In some implementations, a tapered diffuser section 2704 may be coupled between adjoining tube sections to reduce turbulence and other frictional losses caused by the expansion of the flow path 2702 along the aspiration line 2412. In other implementations, a bevel or other means may be coupled to the diffuser section 2704 to further condition the expanding fluid flow.

As partially explained in the Background, the process of phacoemulsification typically involves a two-step process. First, the phaco ultrasound device (phaco handpiece) is used to remove the cataract nucleus from the eye. After the cataract nucleus is removed, a second irrigation and aspiration (I/A) instrument (I/A handpiece) is used to remove the remaining soft cortex from the posterior lens capsule area of the eye where the cataract was located. Removing the cortex from around the delicate posterior lens capsule cannot be performed with the phaco handpiece because it may possibly rupture the posterior capsule, which is a membrane that prevents the vitreous from migrating forward during the procedure. Thus, the I/A handpiece performs an irrigation and aspiration function where the aspiration port is 0.3 mm in diameter and is located on the side of the cannula. An irrigating attachment is often used on the I/A handpiece, but the attachment can be removed to allow a bimanual approach involving a second cannula in the eye to provide the irrigation. A typical phaco tip may include an open distal end titanium cannula having dimensions of 1 mm in diameter, but other sizes and shapes are available.

After the cataract is removed, the surgical technician must remove the irrigation tubing and the aspiration tubing from the connectors of the phaco handpiece located at the rear of the handpiece, and then connect them to the I/A handpiece. The technician must make certain there is no air located in the irrigation line because the air can be placed in the eye, which impacts the visibility by the surgeon.

Figure 28:
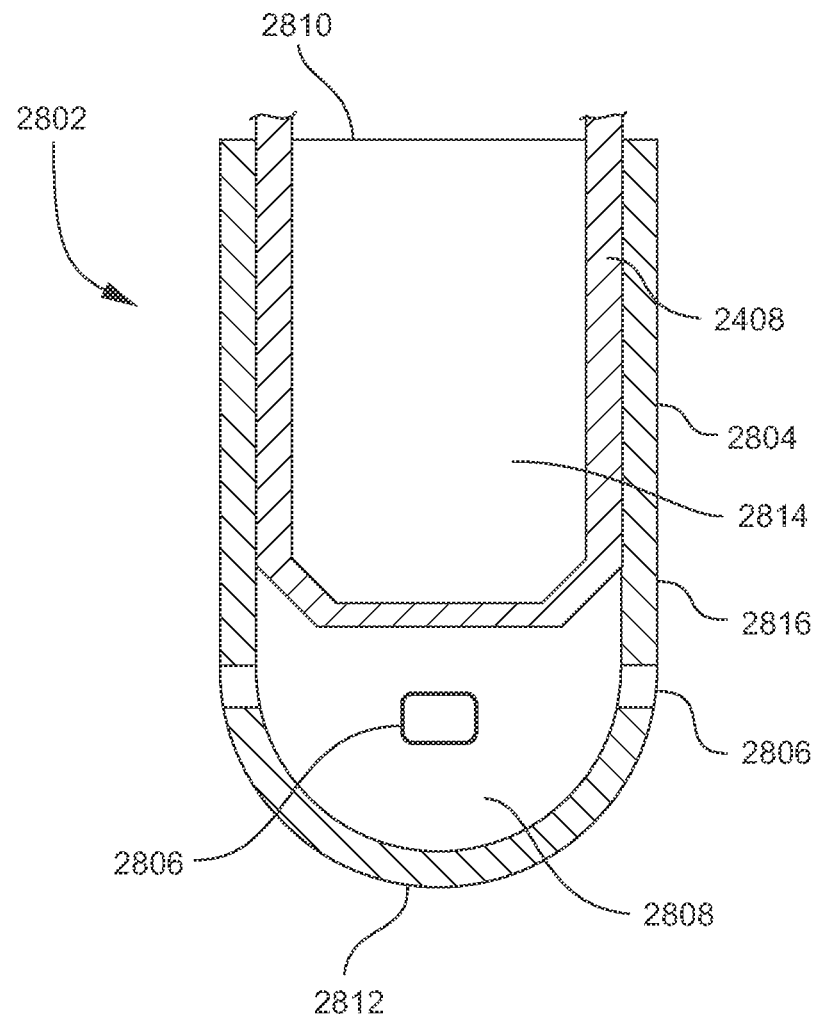
FIG. 28 is a cross-sectional view of an I/A tip membrane of the present invention applied to a distal end of the cannula.

One implementation of the present invention provides for a single handpiece to perform the functions of cataract and cortex removal. As shown in FIG. 28, this may be accomplished by the use of a soft tip membrane 2802 configured to fit snugly over the distal end of the cannula 2408. In the example shown, the tip membrane 2802 may include an elastic sleeve 2804 having an interior 2814 defined by one or more annular sidewalls 2816 extending between an open end 2810 for receiving a distal end of the cannula 2408, and a cup-shaped closed end 2812. The tip membrane 2802 may further include one or more vacuum ports 2806 disposed along the sidewall(s) 2816 of the sleeve 2804. The sleeve 2804 may be made of acrylic, silicone, or other flexible materials having suitable elastic properties. The sleeve 2804 may be adapted to conform to the shape of the cannula 2408 to provide an air-tight interference or compression fit therewith. A pocket 2808 may be formed between the distal end of the cannula 2408 and the closed end 2812 to provide a flow path for fluid and tissue passing from the side port 2806 to the cannula 2408. In some implementations, the side ports 2806 may be approximately 0.3 mm in diameter, or any other suitable dimensions for aspirating cortical material.

According the present teachings, the thickness of the sleeve 2804 may be very thin (on the order of several hundred micrometers) to enable the sleeve 2804 to be stretched over the distal end of the cannula 2408 and, further, to enable the distal tip of a cannula 2408 to reenter an incision, without tearing or further opening the incision, after the tip membrane 2802 is applied to its distal end. Further, the sleeve 2804 may be made of a material having material properties that enable the sleeve 2804 to adhere to the outer surface of the cannula 2408. In some implementations, the inner diameter of the sidewalls 2816 of the tip membrane 2802 may be slightly smaller than the outer diameter of the cannula 2408 to ensure a compression-fit between the tip membrane 2802 and the cannula 2408.

Figure 29:
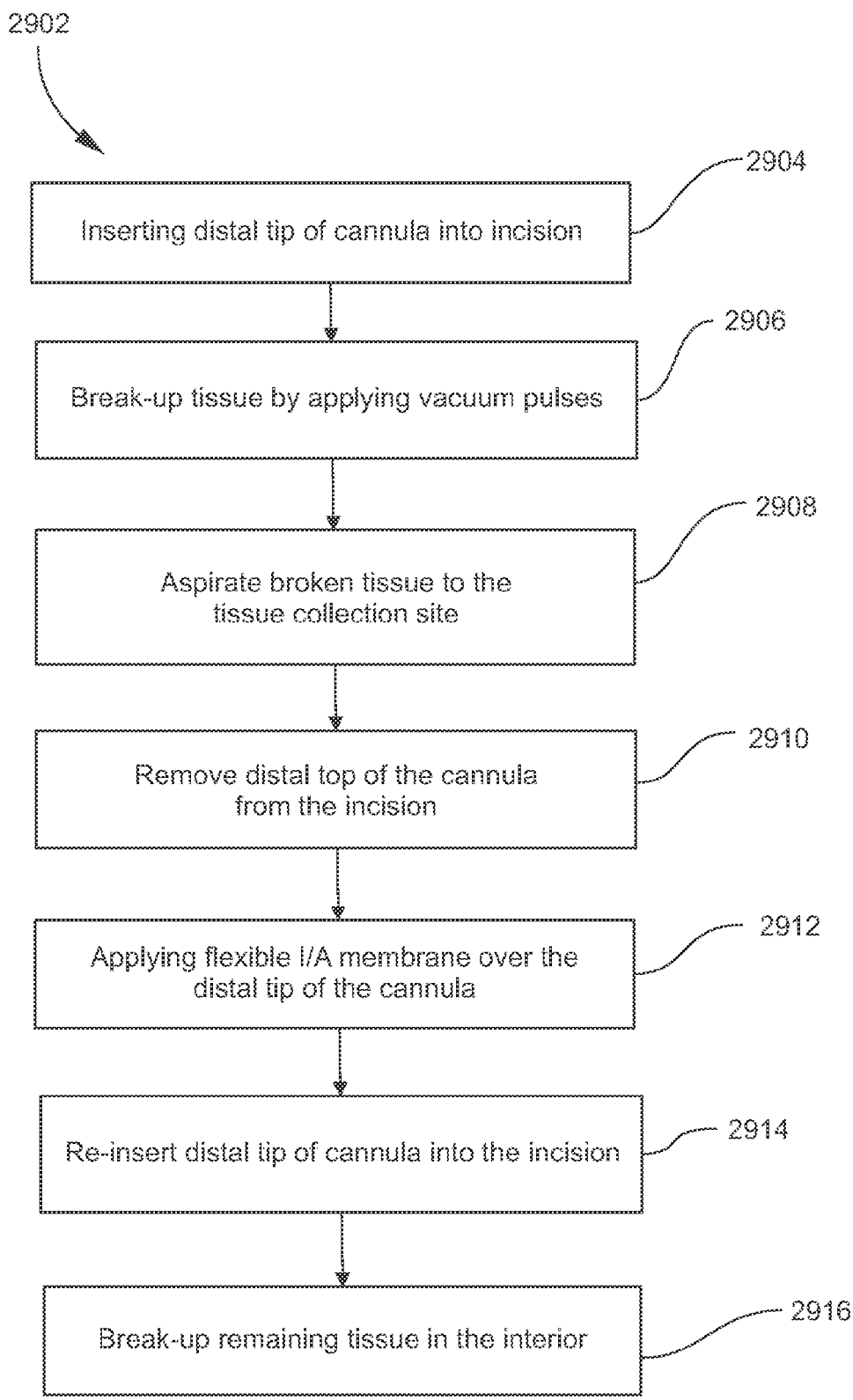
FIG. 29 is a flow diagram illustrating one example of a method of removing tissue from an incision in the eye in accordance with the present invention

In one implementation of the present teachings, a method 2902 for removing tissue from an eye using a single handpiece is illustrated in FIG. 29. As shown, the method 2902 includes a first step 2904 of inserting a distal tip of the cannula 2408 through an incision formed in the eye and into its interior, in a fashion previously described herein. In a next step 2906, cataract tissue in the interior of the eye may be broken-up by applying a series of vacuum pulses to the eye tissue via the cannula 2408. In this step, vacuum pulses may be applied to the eye tissue by actuating a vacuum pulsing device, such as for example, the rotary valve 2524, alternately between an open state and a closed state. After breaking up the tissue, the broken-up tissue may be aspirated through the aspiration line 2412 to the tissue collection site 218, in step 2908. After aspirating the cataract tissue, in step 2910 the distal tip of the cannula 2408 may be removed from the incision in the eye. Once the distal tip of the cannula 2408 is displaced from the eye, in step 2912 a flexible tip membrane 2802 may be applied to the distal end of the cannula 2408 by manual or mechanical means. In step 2914, the distal tip of the cannula 2408, carrying the tip membrane 2802, may be re-inserted into the incision to break-up any remaining cortical tissue in the interior of the eye by, again, applying a series of vacuum pulses to the tissue via the cannula 2408 (step 2916).

To aid the aspiration process, in some implementations the tip membrane 2802 may be applied to the distal end of the cannula 2408 by automated means. FIG. 29 is a cross sectional view of an apparatus 3002 for applying the tip membrane 2802 over the open distal end of the cannula 2408. As shown, the apparatus 3002 may include an enclosure 3004 having an upper section 3006 and a corresponding base 3008. In some implementations, the enclosure 3004 may include a square cross-section. In other implementations, the enclosure 3004 may include a circular, polygon, or other suitable shape. In some implementations, the enclosure 3004 may be constructed from plastic. In other implementations, the enclosure 3004 may be constructed from ceramics, stainless steel, or any other suitable material.

As shown, the upper section 3006 may include a planar top surface 3010 and a circular alignment canal 3016 extending from the top surface 3010 into an interior 3012 of the enclosure 3004. In this example, the alignment canal 3016 may have diametrical dimensions corresponding to the outer diameter of the cannula 2408. A tight diametrical tolerance between the cannula 2408 and the alignment canal 3016 may be necessary to ensure that the cannula 2408 is properly centered with the tip membrane 2802 stored in the interior 3012 of the enclosure 3004. A properly centered cannula 2408 enables the tip membrane 2802 to be properly secured to the open end of the cannula 2408.

A membrane retractor having one or more downwardly extending finger members 3014 may be coupled to the bottom of the upper section 3006, proximate to the base 3008. In some implementations the finger members 3014 may be arranged in a conical fashion. The finger members 3014 are designed to retain the tip membrane 2802 within the interior 3012 of the enclosure 3004 by a friction, stretch, and/or compression-fit. In some implementations, the finger members 3014 may be constructed from plastic or any other suitable material. In other implementations, the membrane retractor may comprise a unitary conical member extending from the bottom of the upper section 3006.

During installation of the tip membrane 2802, the sleeve 2804 of the tip membrane 2802 may first be stretched over the finger members 3014. As the sleeve 2804 is stretched over the finger members 3014, the interior 2814 of the tip membrane 2802 is expanded to a V-shaped configuration to receive the distal end of the cannula 2408. Once the tip membrane is installed over the finger members 3014, in some implementations, the upper section 3006 is assembled with the base 3008 to form the enclosure 3004. Once the enclosure 3004 is assembled, the user may insert the distal end of the cannula 2408 into the alignment canal 3016 until the distal end of the cannula 2408 extends into the interior 2814 of the tip membrane 2802 near the closed end 2812. Near the closed end 2812 of the tip membrane 2802, the inner diameter of the sleeve sidewalls 2816 are narrowed such that the tip membrane 2802 adheres to outer surface of the cannula 2408. Once the tip membrane 2802 affixes to the distal end of the cannula 2408, the user may apply additional downward force to further urge the cannula 2408 towards the base 3008. As the cannula 2408 is moved towards the base 3008, the compression-fit between the tip membrane 2802 and the cannula 2408 may cause the tip membrane 2802 to be displaced from the finger members 3014. As the tip membrane 2802 is displaced from the fingers members 3014, the elastic sleeve 2804 may contract and affix itself to the cannula 2408 in a secure manner, and in some implementations in a permanent manner. After the tip membrane 2802 is affixed to the cannula 2408, the user may then remove the cannula 2408 from the enclosure 3004, and proceed with the removal of the cortex material. In most implementations, for the sanitary purposes, the tip membrane 2802 is designed to be a single-use accessory.

In this example, the tip membrane 2802 may be positioned in the enclosure 3004 such that it is displaced from the finger members 3014 at about the same point that the tip membrane 2802 comes into contact with the bottom of the enclosure 3004. This contact at the bottom of the enclosure 3004 provides a signal to the user that the tip membrane 2802 is connected to the cannula 2408 and, further, can be removed from the enclosure 3004.

In some implementations, the upper section 3006 may be detachable from the base 3008 to provide access to the finger members 3014 when installing the tip membrane 2802 in the apparatus 3002. In other implementations, the upper section 3006 may be integrally formed with the base 3008. In these implementations, access to the finger members 3014 may be provided by one or more openings formed in the sidewalls and/or a bottom surface of the enclosure 3004.

In accordance with the present implementation, a user may first remove the cataract nucleus from a target site using an implementation of a tissue removal device 2402 of the present invention. After the cataract is removed, the user may insert the device into the enclosure 3004 to affix the tip membrane 2802 to the distal end of the cannula 2408. Once the tip membrane 2802 is secured to the cannula 2408, the user may then use the same device to remove the remaining cortical materials from the target site.

The present implementation provides means where the tip membrane 2802 may be automatically connected to cannula 2408. The user may easily do this without the assistance of a technician if desired. And further, a technician is not required to change the instrument tubing between the cataract and cortex removal steps of the procedure. This provides an efficiency and cost savings advantage over existing phaco instrumentation and procedures. Further, because tissue removal devices of the present invention are not based on activating the tip with mechanical ultrasonic power, the tip membrane 2802 applied to the cannula 2408 is more likely to remain secured to the distal end of the cannula 2408 because mechanical ultrasound would likely vibrate the tip membrane 2802 off of the cannula tip of a traditional phaco ultrasonic device.

Figure 31:
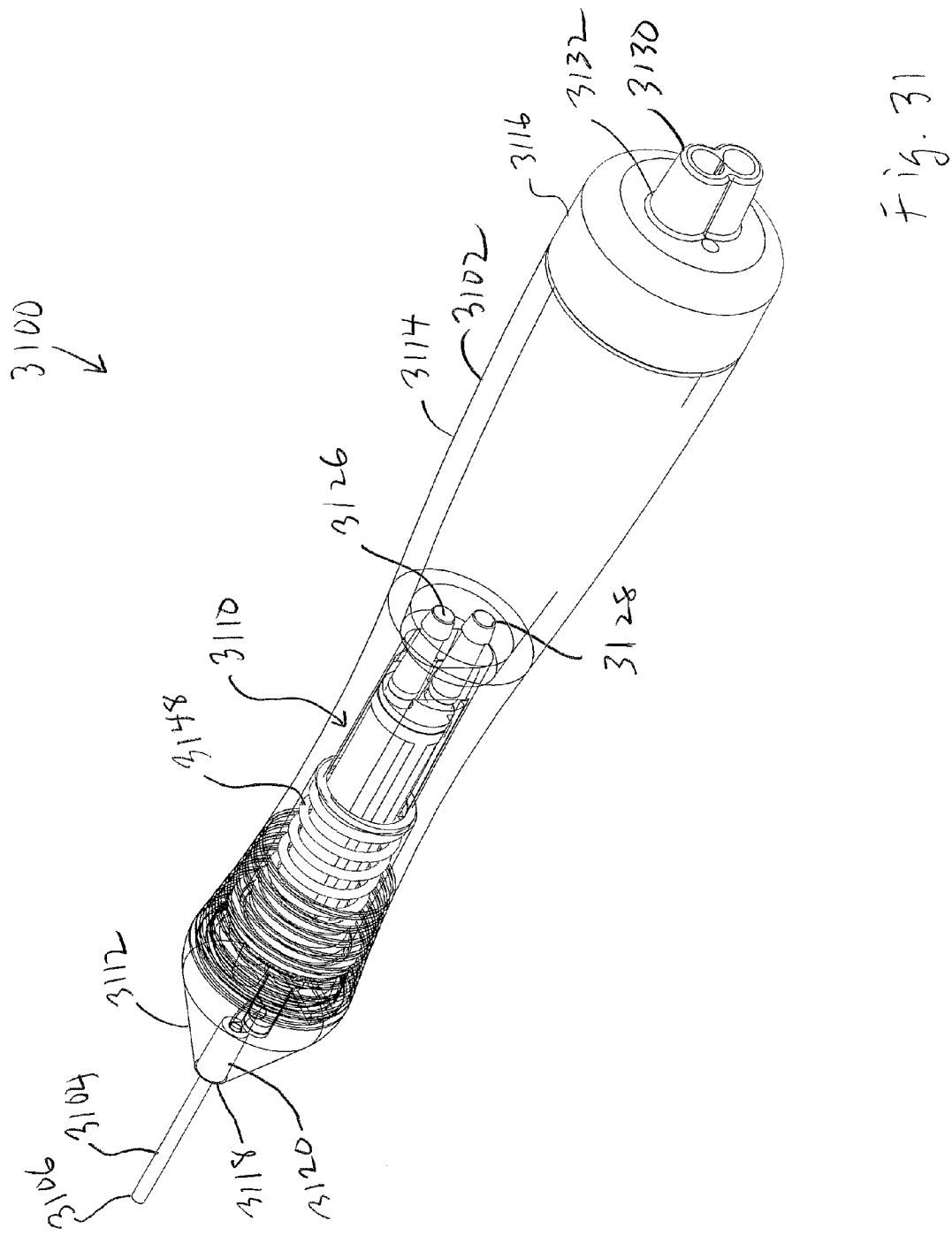
FIG. 31 is a perspective view of an example of a tissue removal device according to another implementation.
Figure 32:
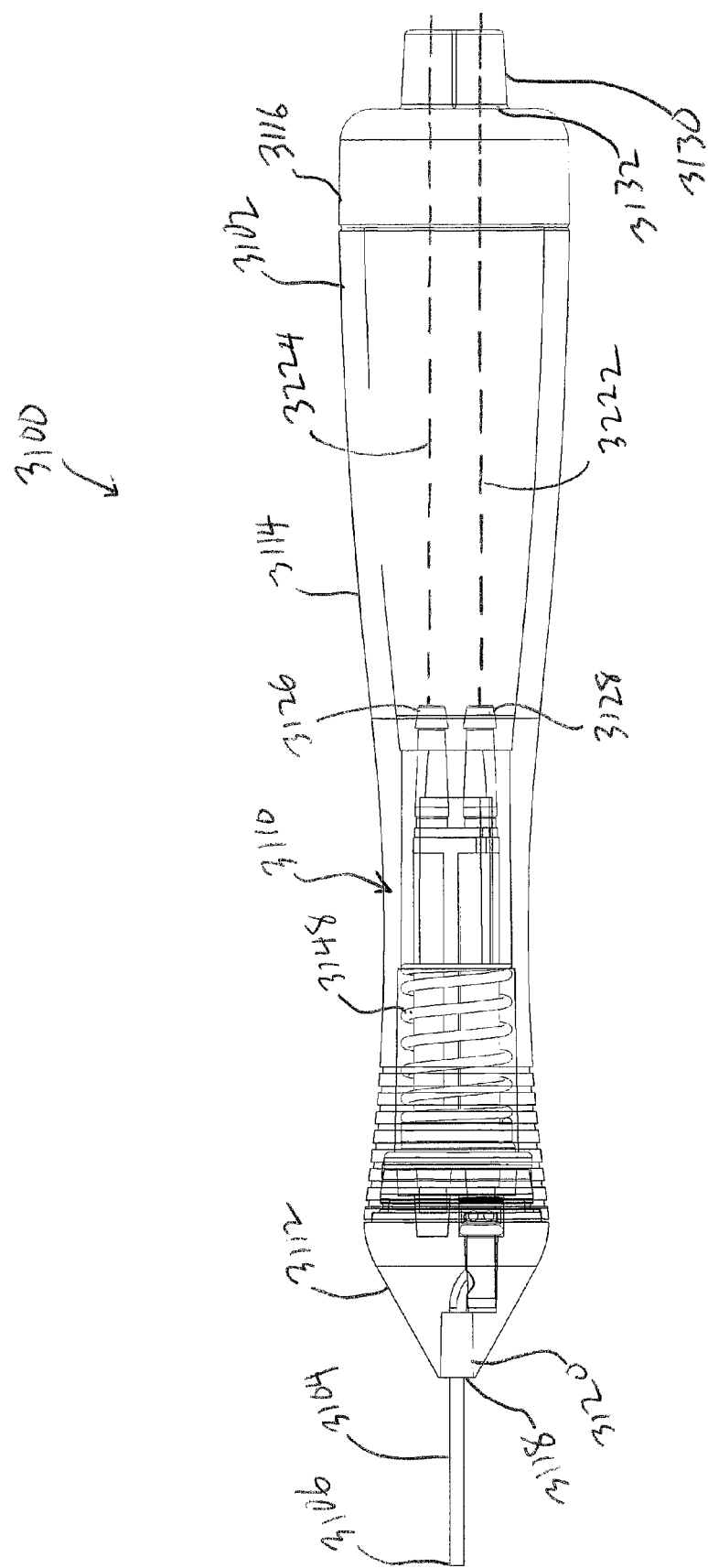
FIG. 32 is a plan view of the tissue removal device illustrated in FIG. 31.

FIGS. 31 and 32 are perspective and plan views, respectively, of an example of a tissue removal device 3100 according to another implementation. The tissue removal device 3100 is generally configured as a handpiece, or hand-held instrument, sized and shaped to be held by a user. The tissue removal device 3100 includes handpiece housing 3102 that encloses various components in its interior, an aspiration cannula 3104 of rigid composition extending from the interior to a distal tip 3106 outside the housing 3102, and a linear actuator including a valve assembly 3110 disposed in the interior. The housing 3102 may generally be elongated along a longitudinal axis of the tissue removal device 3100. The housing 3102 may include a plurality of sections assembled together. In the illustrated example, the housing 3102 includes a distal (or front) body 3112 from which the aspiration cannula 3104 extends, a main (or intermediate) body 3114 coupled to the distal body 3112 in a fluid-sealed manner and elongated along the longitudinal axis, and a proximal (or rear) body 3116 coupled to the main body 3114 opposite to the distal body 3112. In the present context, the term "fluid-sealed" means "gas-tight" or "vacuum-tight" and refers to a sealed condition that eliminates or at least substantially minimizes the transfer of gas across or through the interface or component being as described as "fluid-sealed." The distal body 3112 includes a distal housing opening 3118 through which the aspiration cannula 3104 extends in a fluid-sealed manner. For this purpose, a distal seal 3120 of suitable configuration and composition may be provided at the interface between the aspiration cannula 3104 and the distal housing opening 3118.

In some implementations, the tissue removal device 3100 is designed to be disposable, in which case the tissue removal device 3100 is provided to the user in a permanent form. In the present context, the term "permanent" (e.g., permanently assembled, installed, coupled, etc.) means that the tissue removal device 3100 is not able to be disassembled by a user without damaging the tissue removal device 3100 or rendering it inoperable. For instance, the various sections of the housing 3102 are not able to be disassembled, the aspiration cannula 3104 is not able to be removed from the housing 3102, and the fluid lines are not able to be removed from the housing 3102.

In the illustrated example, the valve assembly 3110 is pneumatically-actuated and is configured for applying vacuum to, and inducing controlled vacuum pulses in, the aspiration cannula 3104. For this purpose, the valve assembly 3110 communicates with the aspiration cannula 3104, and with an aspiration line 3222 and a pressurized gas line 3224 that are depicted as dashed lines in FIG. 32. The aspiration line 3222 and pressurized gas line 3224 may be flexible tubes that extend out from the housing 3102 via feed-through members. The valve assembly 3110 may include a gas line fitting 3126 and an aspiration line fitting 3128 configured for attachment to the tubes. In the illustrated example, a single feed-through member 3130 having two bores extends through a proximal housing opening 3132 of the proximal body 3116. A gap between the bores accommodates a dual-lumen construction in which the respective tubes for the aspiration line 3222 and pressurized gas line 3224 are integrally connected side-by-side by an intervening strip of material (not shown). In the illustrated example, the tubes are flexible to accommodate reciprocating action of the valve assembly 3110, as described below. In other implementations, the aspiration line 3222 and pressurized gas line 3224 may pass through the housing 3102 via a side opening or openings thereof, and/or may pass through housing 3102 via separate openings.

Figure 33:
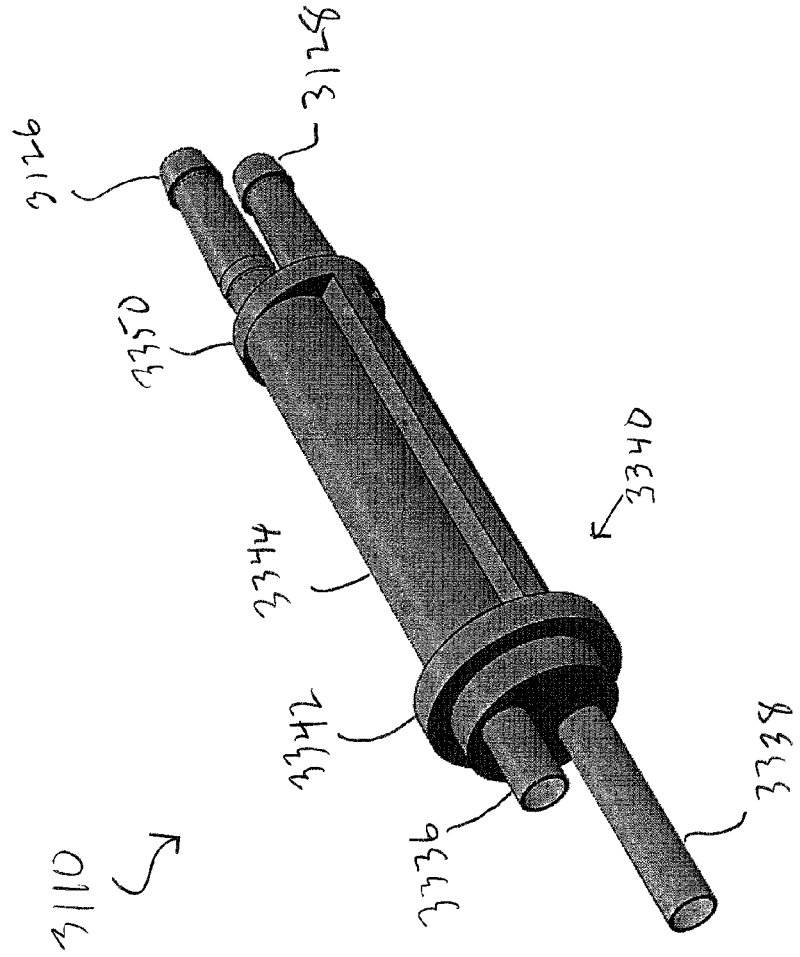
FIG. 33 is a perspective view of an example of a valve assembly that may be provided with the tissue removal device illustrated in FIGS. 31 and 32.

FIG. 33 is a perspective view of an example of the valve assembly 3110. The valve assembly 3110 includes a gas conduit (or gas cannula) 3336, an inner cannula 3338, and a piston 3340. The gas conduit 3336, inner cannula 3338 and piston 3340 may be constructed of rigid materials such as various metals and polymers. The piston 3340 may include a piston head (or flange) 3342 and a sleeve 3344 coaxially surrounding the gas conduit 3336 and inner cannula 3338. The piston 3340 (e.g., the piston head 3342 or an end portion of the sleeve 3344) may include bores through which the gas conduit 3336 and inner cannula 3338 extend. As described further below, the valve assembly 3110 is configured to be pneumatically actuated between an open position and a closed position. In the open position, the valve assembly 3110 completes an aspiration path from the aspiration cannula 3104, through the inner cannula 3338 and out from the housing 3102 to enable aspirant (e.g., tissue and fluid) to be aspirated to a collection receptacle. In the closed position, the valve assembly 3110 blocks the aspiration path. The valve assembly 3110 may be reciprocated between the open and closed positions according to a desired pulse profile such as illustrated, for example, in FIGS. 2 and 3, to control fluid flow and break up tissue as described earlier in the present disclosure. In the present implementation, the valve assembly 3110 is configured to be normally biased into the closed position by spring force and positively actuated into the open position by application of gas pressure against the spring force. That is, the forward stroke of the valve assembly 3110 (toward the closed position) is spring-actuated and the rearward stroke (toward the open position) is pneumatically actuated. For this purpose, the valve assembly 3110 includes a spring 3148 (FIGS. 31 and 32) mounted in the housing 3102 between the piston head 3342 and an internal wall of the housing 3102 and coaxially surrounding the sleeve 3344. The piston head 3342 thus has an outer diameter larger than that of the sleeve 3344 such that the piston head 3342 contacts the spring 3148. A proximal portion 3350 of the sleeve 3344 may be configured to come into abutment with a suitable stop member, such as an internal wall (not shown) of the housing 3102, to provide a limit on the maximum rearward stroke of the valve assembly 3110. The proximal portion 3350 may be provided with a resilient member (not shown) to facilitate contact with the stop member.

In the present implementation, the valve assembly 3110 is spring-biased into the closed position as a safety measure to prevent vacuum from being applied to a surgical site such as a patient's eye at undesired times. In another implementation, the components of the valve assembly 3110 may be configured such that the valve assembly 3110 is spring-biased into the open position and pneumatically actuated into the closed position. In another implementation, the valve assembly 3110 may be configured for being pneumatically actuated into both the open position and closed position.

Figure 34:
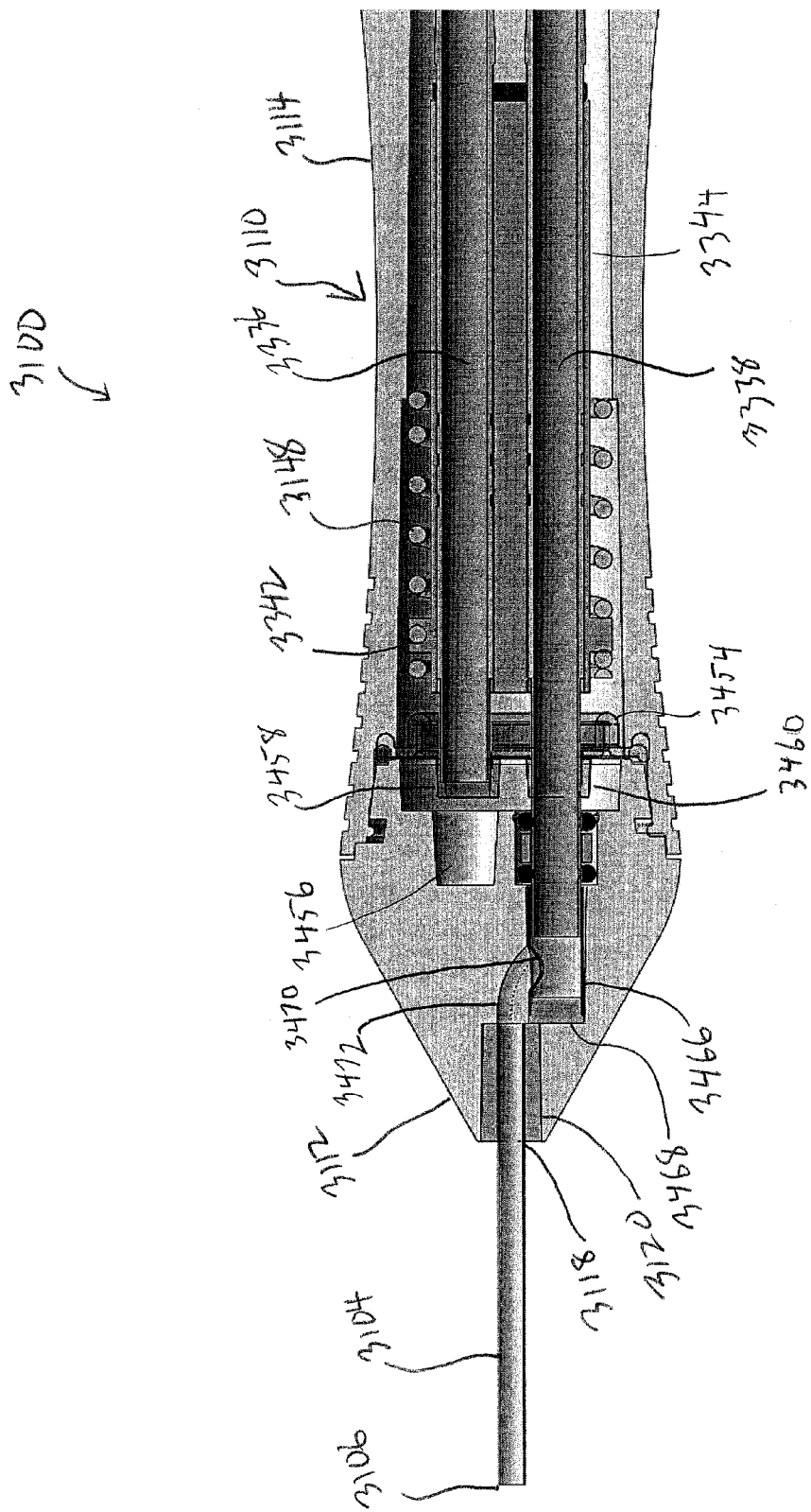
FIG. 34 is a cross-sectional view of the tissue removal device illustrated in FIGS. 31 and 32, with the valve assembly in the open position.

FIG. 34 is a cross-sectional view of the tissue removal device 3100 with the valve assembly 3110 in the open position. The distal body 3112 may be secured to the main body 3114 of the housing 3102 by any suitable fluid-sealing means, which may include the use of one or more o-rings or other types of sealing elements. In implementations where the tissue removal device 3100 is disposable, the distal body 3112 may be secured to the main body 3114 in a permanent manner. In the present implementation, the linear actuator includes a diaphragm 3454 securely mounted transversely to the longitudinal axis and coaxially surrounding the gas conduit 3336 and inner cannula 3338. The diaphragm 3454 may be composed of any suitable flexible material capable of withstanding repeated cycling of gas pressurization and forcible contact with the piston head 3342. Additionally, one or more inside walls or surfaces of the housing 3102 define a gas chamber 3456 on the distal side of the diaphragm 3454. These inside walls or surfaces may be part of the distal body 3112, the main body 3114, or both. The gas chamber 3456 is bounded on at least one side by the diaphragm 3454, whereby the diaphragm 3454 provides a fluid-sealed boundary between the gas chamber 3456 and the other portion of the interior of the housing 3102. The volume of the gas chamber 3456 varies in accordance with the degree to which the diaphragm 3454 is expanded or contracted in response to gas pressure within the gas chamber 3456.

In some implementations, the diaphragm 3454 includes a first bore 3458 through which the gas conduit 3336 passes and a second bore 3460 through which the inner cannula 3338 passes. The diaphragm material is tightly compressed around the gas conduit 3336 at the first bore 3458 and around the inner cannula 3338 at the second bore 3460. The gas conduit 3336 passes through the first bore 3458 into the gas chamber 3456, such that an open distal end of the gas conduit 3336 communicates with the gas chamber 3456. The distal end of the gas conduit 3336 translates back and forth within the gas chamber 3456 as the valve assembly 3110 reciprocates through the forward and rearward strokes. The gas chamber 3456 is shaped to accommodate this translation.

In the illustrated example, the inner cannula 3338 passes through the second bore 3460, through the gas chamber 3456, and into an outer cannula 3466 disposed in the distal body 3112. The distal body 3112 and outer cannula 3466 may be fluidly isolated from the gas chamber 3456 by any suitable manner. In the illustrated example, the interface between the inner cannula 3338 and the opening in the gas chamber 3456 leading into the distal body 3112 is sealed by a seal interposed between the gas chamber 3456 and the outer cannula 3466. In the illustrated example, the seal includes a pair of o-rings separated by an annular spacer. The outer cannula 3466 includes a distal end that is closed off in a secure, fluid-sealed manner by a resilient seal 3468 (e.g., a plug, stopper, closure, etc.). The outer cannula 3466 also includes a valve port 3470 that communicates with the aspiration cannula 3104. The inner cannula 3338 and outer cannula 3466 thus form a linearly actuated valve that communicates with the aspiration cannula 3104 in a fluid-sealed manner.

The valve port 3470 may be formed through the cylindrical wall of the outer cannula 3466. In some implementations, the valve port 3470 is a side port oriented ninety degrees to the aspiration cannula axis. In the present context, the term "ninety degrees" is not limited to exactly ninety degrees, and thus encompasses the terms "substantially ninety degrees" and "about ninety degrees." The valve port 3470 may communicate with the aspiration cannula 3104 via a transition 3472 disposed between, and fluidly communicating with, the aspiration cannula 3104 and the valve port 3470. The transition 3472 may be an angled section (e.g., a bent section, curved section, elbow section, etc.). In some implementations, depending on construction, the transition 3472 may be considered to be integrally part of, or an extension of, a distal section of the aspiration cannula 3104 that extends along an aspiration cannula axis in a straight manner. In other implementations, the transition 3472 may be considered to be a separate component disposed between the aspiration cannula 3104 and the outer cannula 3466. The transition 3472 is "angled" relative to the aspiration cannula axis—that is, the transition 3472 follows a curved or bent path from the aspiration cannula 3104 to the valve port 3470. Although the valve port 3470 is oriented 90 degrees to the aspiration cannula axis, in some implementations it is preferred that the transition 3472 terminate with a profile by which the transition 3472 transitions to the valve port 3470 at an angle less than 90 degrees. This configuration is illustrated by a dotted line in FIG. 34, and may provide a smoother (less abrupt) aspiration pathway from the aspiration cannula 3104 into the inner cannula 3338. The transition 3472 is adjoined (e.g., welded, bonded, etc.) to the surface of the outer cannula 3466 surrounding the valve port 3470 in a fluid-sealed manner. If the transition 3472 is a separate component from the aspiration cannula 3104, the transition 3472 is likewise adjoined to the aspiration cannula 3104 in a fluid-sealed manner.

In the present implementation, the aspiration cannula 3104, transition 3472, outer cannula 3466 and inner cannula 3338 are all composed of a rigid material, such as a metal or rigid polymer. By this configuration, the entire aspiration path from the distal tip 3106 of the aspiration cannula 3104 to the valve assembly 3110 is defined by rigid structures, which facilitates the application of very precise and controlled vacuum pulses in accordance with the present teachings. In some implementations, the inside diameter of the valve port 3470 is equal to or greater than the inside diameter of the distal tip 3106. In some implementations, the inside diameter of the valve port 3470 is larger than the inside diameter of the distal tip 3106, which facilitates an expanding cross-sectional flow area of the aspiration path and prevents clogging of tissue in the aspiration path. The inside diameter of the transition 3472 may gradually increase from that of the aspiration cannula 3104 to that of the valve port 3470. In some implementations, the inside diameter of the distal tip 3106 ranges from 0.2 mm to 2 mm, and the inside diameter of the valve port 3470 ranges from 0.05 mm to 5 mm.

In operation, the rearward stroke of the valve assembly 3110 into the open position shown in FIG. 34 is effected by flowing pressurized gas from a suitable pressurized gas source (not shown) through the gas line 3224 (FIG. 32), through the gas conduit 3336, and into the gas chamber 3456. As gas pressure increases in the gas chamber 3456, it forces the diaphragm 3454 to expand in the rearward direction. The diaphragm 3454 is either already in contact with the piston head 3342 or expands into contact with the piston head 3342. In either case, the expanding diaphragm 3454 forces the piston head 3342 in the rearward direction against the biasing force imparted by the spring 3148. During expansion of the diaphragm 3454, the piston head 3342 is either already in contact with the spring 3148 or comes into contact with the spring 3148 as a result of the expansion. In the present implementation, as shown in FIG. 34, the entire valve assembly 3110 is translated in the rearward direction with the piston head 3342. In particular, the inner cannula 3338 is translated rearward through the stationary outer cannula 3466. Due to the rearward translation, an open distal end of the inner cannula 3338 clears the valve port 3470. Hence, an open aspiration path is established, which runs from the distal tip 3106, and through the aspiration cannula 3104, the transition 3472, the valve port 3470, the open space in the outer cannula 3466 between the resilient seal 3468 and the open distal end of the inner cannula 3338, the inner cannula 3338, the remaining portion of the aspiration line 3222 (FIG. 32), and to a collection receptacle (not shown) external to the tissue removal device 3100.

Figure 35:
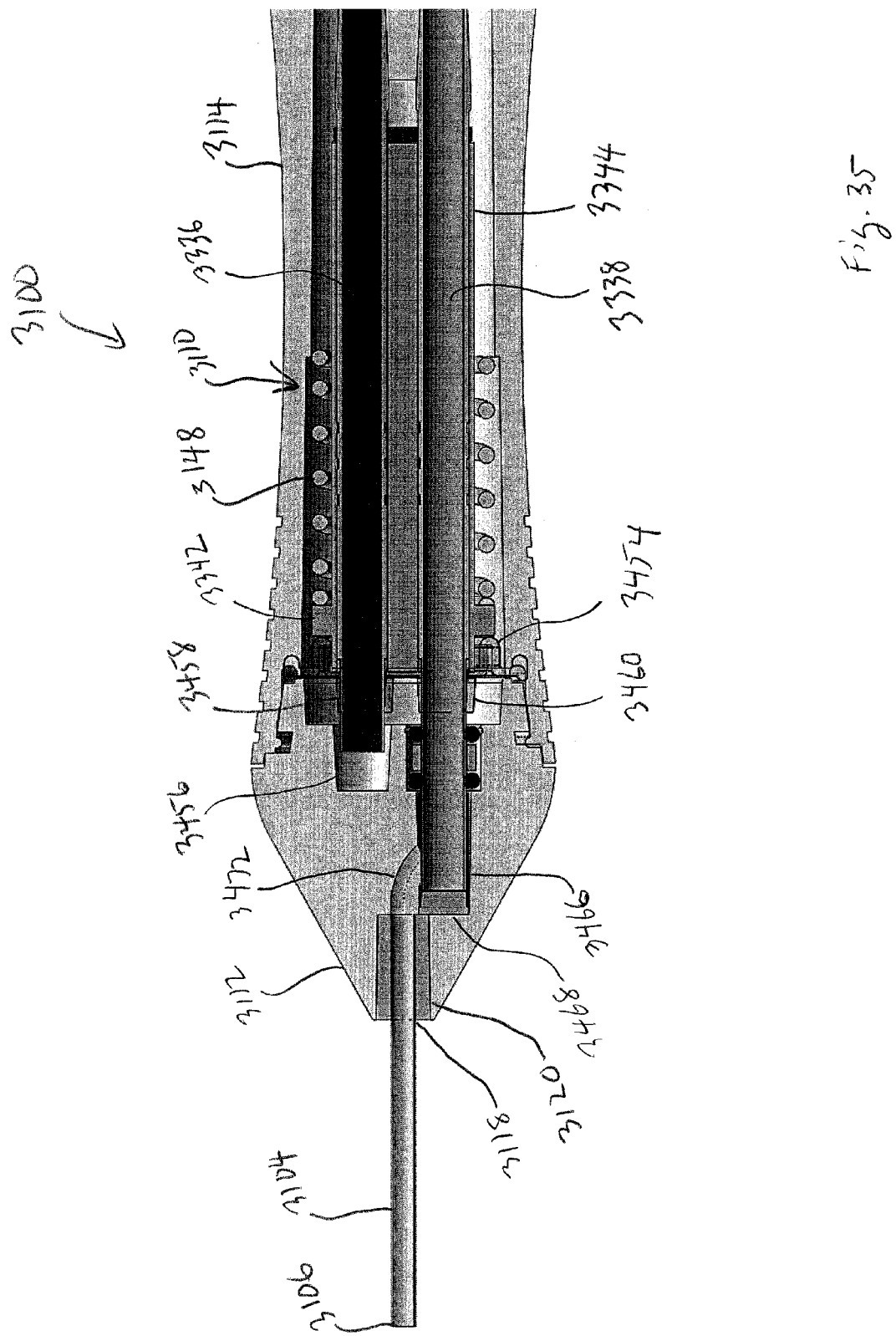
FIG. 35 is a cross-sectional view of the tissue removal device illustrated in FIGS. 31 and 32, with the valve assembly in the closed position.

FIG. 35 is a cross-sectional view of the tissue removal device 3100 with the valve assembly 3110 in the closed position. The closed position is attained by ceasing the flow of pressurized gas into the gas chamber 3456, or reducing the flow enough to enable the diaphragm 3454 to contract and the valve assembly 3110 to translate in the forward direction back to the closed position, which is assisted by the spring 3148. In the closed position, the inner cannula 3338 is translated forwardly through the outer cannula 3466 and comes into fluid-sealed contact with the resilient seal 3468. In this position, the inner cannula 3338 completely blocks (or occludes) the valve port 3470, thereby breaking the application of vacuum in the aspiration cannula 3104.

It can be seen that through appropriate control of the pressurized gas flow to the valve assembly, the valve assembly 3110 may be reciprocated back and forth between the open and closed positions at any desired frequency to achieve a desired vacuum-pulsing effect. The level of vacuum applied to the aspiration cannula 3104, the activation of vacuum pulsing, and adjustment of the pulsing parameters may be controlled by a user via a control console and/or a foot pedal, as described earlier in this disclosure.

It can be seen that in the implementation illustrated in FIGS. 31-35, the tissue removal device 3100 includes an internal valve that is reciprocated between open and closed positions by a pneumatically-driven linear actuator. A feature of the internal valve is the valve port 3470 (defined in the illustrated example by the stationary outer cannula 3466) with which the aspiration cannula 3104 is in fluid communication. The valve port 3470 is alternately opened and closed by linear movement of the inner cannula 3338, which in the illustrated example not only serves as a valve component but also as part of the aspiration line through the handheld instrument. By this configuration, the axis of the aspiration cannula 3104 is offset from the axis of the inner cannula 3338, the aspiration cannula 3104 and the inner cannula 3338 may be parallel or substantially parallel, and the valve port 3470 is oriented transversely or substantially transversely to the aspiration cannula 3104 and the inner cannula 3338. This configuration enables the internal valve to be reliably actuated between open and closed positions in a very vacuum-tight manner over a wide range of frequencies, thereby enabling precise, robust control over vacuum pulsing.

It will be understood that the tissue removal device 3100 illustrated in FIGS. 31-35 is but one implementation, and that other implementations are encompassed by the presently disclosed subject matter. As examples, the gas chamber 3456 and diaphragm 3454 may be configured such that the inner cannula 3338 does not pass through them, and such that the inner cannula 3338 and/or other components of the internal valve are fluidly isolated from the gas chamber 3456 without the use of specific sealing elements. The valve assembly 3110 and diaphragm 3454 may be configured such that the gas conduit 3336 and inner cannula 3338 do not pass through the diaphragm 3454. The valve assembly 3110 may be configured such that the gas conduit 3336 does not pass through the piston 3340 and/or the gas conduit 3336 is stationary. The valve assembly 3110 may be configured such that the inner cannula 3338 is mechanically linked to the piston 3340 but does not pass through the piston 3340. Moreover, in other implementations, the linear actuator may utilize a pneumatically-driven component other than a flexible diaphragm. In still other implementations, the operation of the linear actuator may be based on non-pneumatic means, such as electrical, electromechanical, or electromagnetic means.

Figure 36:
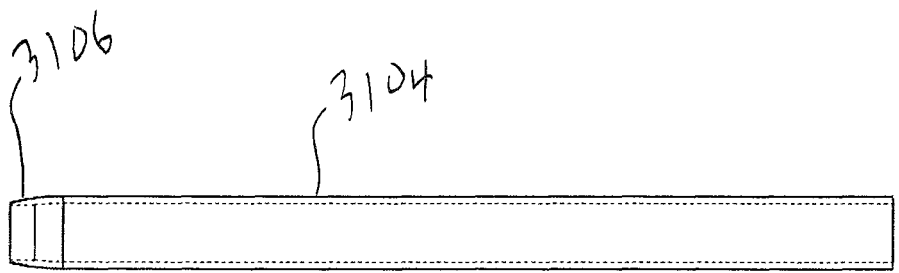
FIG. 36 is a side view of an example of an aspiration cannula according to another implementation.

FIG. 36 is a side view of an example of the aspiration cannula 3104. In this example, the distal tip 3106 is tapered such that the inside diameter of the distal tip 3106 is less than that of the remaining portion of the aspiration cannula 3104. The tapered configuration helps to prevent clogging of tissue in the aspiration cannula 3104. In other implementations, all or part of the remaining portion of the aspiration cannula 3104 may be tapered such that the inside diameter gradually increases in the direction toward the proximal end of the aspiration cannula 3104, thereby providing an expanding vacuum path through the aspiration cannula 3104. In some implementations, the wall of the aspiration cannula 3104 has a thickness (in the radial direction) of 0.3 mm or less.

Figure 37:
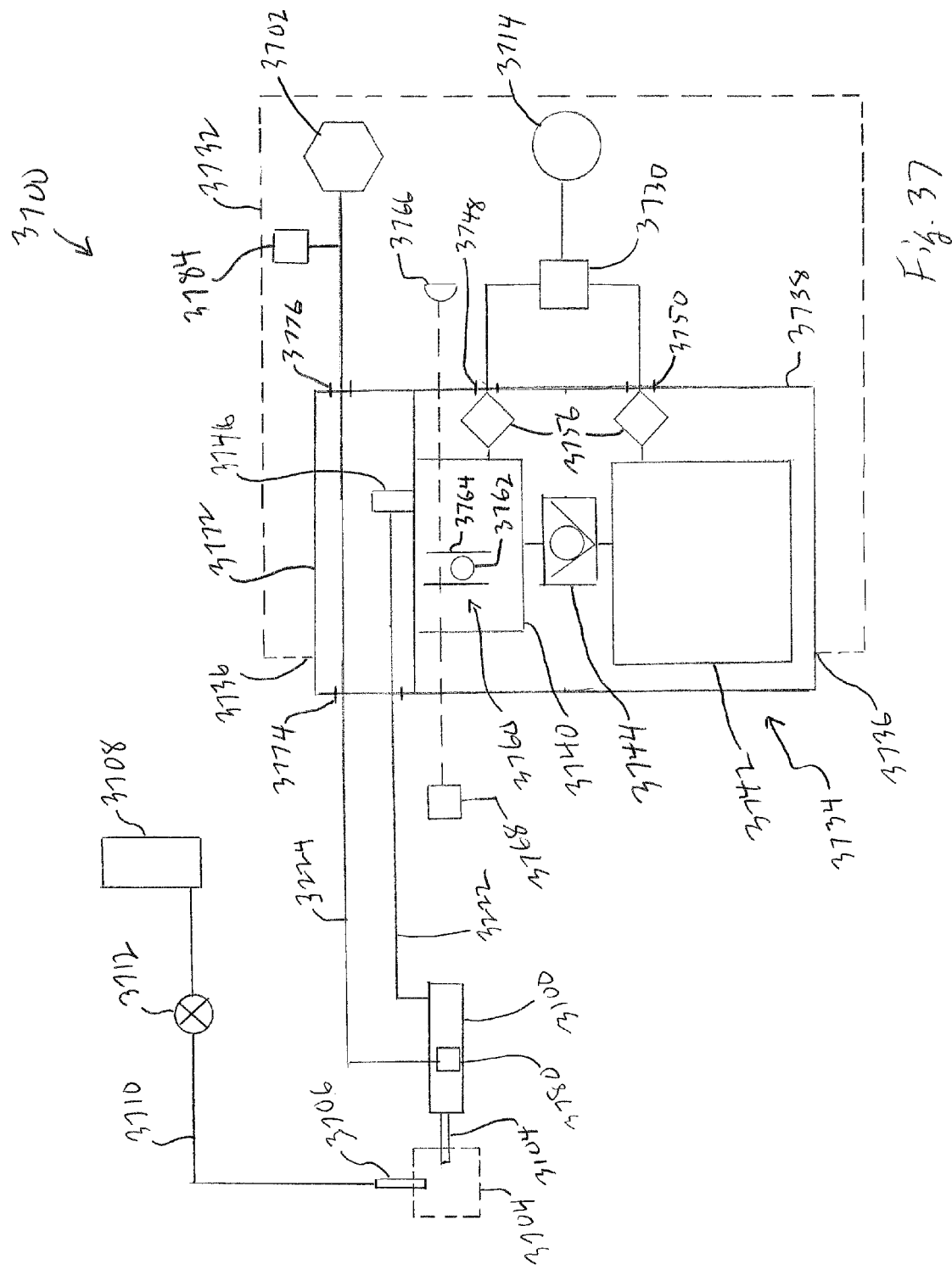
FIG. 37 is a schematic view of an example of a tissue removal system according to another implementation.

FIG. 37 is a schematic view of an example of a tissue removal system 3700 according to another implementation. The tissue removal system 3700 includes a tissue removal device and a tissue (and fluid) collection receptacle communicating with the tissue removal device via an aspiration line 3222. The tissue removal device may, for example, be the same or similar to the tissue removal device 3100 described above and illustrated in FIGS. 31-36. The tissue removal device 3100 may thus include the aspiration cannula 3104, and a linear actuator 3780 that drives the internal valve. In the present implementation, the linear actuator 3780 is pneumatically powered and thus receives pressurized gas from any suitable pressurized gas source 3702 via a gas line 3224. The aspiration cannula 3104 is schematically shown as being operatively inserted into a surgical site 3704 at which aspiration of tissue is desired, such as a patient's eye. A separate hand-held irrigation instrument 3706 is also shown as being operatively inserted into the surgical site 3704. An irrigation fluid source 3708 supplies the irrigation instrument 3706 with irrigation fluid via an irrigation fluid line 3710. The flow of irrigation fluid may be controlled by a valve 3712 or any other suitable means.

In the present implementation, the collection receptacle is positioned in-line between the tissue removal device 3100 and a vacuum source (e.g., a pump) 3714. The vacuum source 3714 may be any suitable device for generating vacuum such as, for example, the vacuum sources or pumps described earlier in the present disclosure. The collection receptacle includes at least one internal chamber for receiving aspirated tissue and fluid. The collection receptacle thus may include an inlet communicating with the aspiration line 3222 leading from the tissue removal device 3100, and an outlet communicating with a vacuum line leading to the vacuum source. At the outlet, the collection receptacle may include a filter or other device configured for separating liquid and solid material from gas, thereby ensuring that liquid and solid material do not flow through the vacuum line to the vacuum source 3714. A vacuum regulator 3730 is positioned in-line between the outlet of the collection receptacle and the vacuum source 3714. The vacuum regulator 3730 may be one or more components as needed to control the level of vacuum applied to the collection receptacle and/or tissue removal device 3100.

In the present implementation, the vacuum source 3714, or both the vacuum source 3714 and the pressurized gas source 3702, are integrated with a control console 3732. The control console 3732 may include other features as described above and illustrated in FIG. 1. A foot-operated control device may also be provided as described above and illustrated in FIG. 1. The control console 3732 may also include a valve control device 3784 configured for controlling the flow of pressurized gas from the pressurized gas source 3702 to the actuator 3780 of the tissue removal device 3100. The valve control device 3784 may have any suitable mechanical, electromechanical, or electromagnetic configuration for this purpose. The valve control device 3784 may communicate with vacuum pulse control circuitry and/or software of the control console 3732. Operating parameters of the valve control device 3784 (e.g., vacuum pulsing parameters) may be adjustable by the user via controls provided on the control console 3732 and/or the above-noted foot-operated control device. Also the present implementation, the collection receptacle is provided in the form of a cassette 3734 that is configured for removable installation by a user into a cassette receptacle 3736 (e.g., a bay, slot, etc.) of the console 3732. The console 3732 may include a device (not shown) for locking the cassette 3734 in place in the fully installed position (i.e., operative position), and for releasing the cassette 3734 from the installed position as desired by the user. The console 3732 may include a device (not shown) for providing an illuminated indication that the cassette 3734 has been installed in the installed position.

In the present implementation, the cassette 3734 includes a cassette housing 3738, a first (or primary) collection chamber 3740 in the cassette housing 3738, and a second (or secondary) collection chamber 3472 in the cassette housing 3738. The second collection chamber 3742 communicates with the first collection chamber 3740 via a cassette valve 3744 that may be a passive one-way valve or check valve. The cassette 3734 also includes an aspiration inlet 3746 communicating with the aspiration line 3222. For example, the aspiration inlet 3746 may include a fitting to which a tube of the aspiration line 3222 is coupled. The aspiration inlet 3746 communicates with the first collection chamber 3740. The cassette 3734 also includes a first vacuum port 3748 communicating with the first collection chamber 3740, and a second vacuum port 3750 communicating with the second collection chamber 3742. The first vacuum port 3748 and second vacuum 3750 port may communicate with the vacuum regulator 3730 via respective vacuum lines, and the vacuum regulator 3730 may communicate with the vacuum source 3714 via a common vacuum line. The cassette 3734 may also include one or more hydrophobic filters 3756 providing a liquid barrier between the first collection chamber 3740 and second collection chamber 3742 and the vacuum source 3714.

The vacuum regulator 3730 may be configured for controlling the respective vacuum levels in the first collection chamber 3740 and second collection chamber 3742. The cassette valve 3744 is configured such that it is closed when the pressure in the first collection chamber 3740 is lower than the pressure in the second collection chamber 3742 (i.e., when the vacuum level is higher in the first collection chamber 3740 than in the second collection chamber 3742), and is open when the pressure in the first collection chamber 3740 is higher than the pressure in the second collection chamber 3742 (i.e., when the vacuum level is lower in the first collection chamber 3740 than in the second collection chamber 3742). In a first tissue collection state (which may be a normal or initial tissue collection state), the first collection chamber 3740 may be utilized as the sole collection chamber, i.e., with the cassette valve 3744 closed. The first tissue collection state may be implemented by, for example, applying vacuum only to the first collection chamber 3740. In the first tissue collection state, the aspiration path runs from the aspiration cannula 3104, and through the aspiration line 3222 and aspiration inlet 3746, and into the first collection chamber 3740. The first collection chamber 3740 may be smaller (of lesser volume) than the second collection chamber 3742 to facilitate rapid adjustments to vacuum level. In a second tissue collection state (which may follow the first tissue collection state), both the first collection chamber 3740 and the second collection chamber 3742 may be utilized for tissue collection, i.e., with the cassette valve 3744 open. The second tissue collection state may be implemented by, for example, applying vacuum only to the second collection chamber 3742 or applying a higher level of vacuum to the second collection chamber 3742. In the second tissue collection state, the aspiration path thus additionally runs from the first collection chamber 3740, through the cassette valve 3744, and into the second collection chamber 3742. The second tissue collection state may be implemented when, for example, the amount of tissue and fluid being collected is great enough to warrant use of the larger second collection chamber 3742 to prevent the first collection chamber 3740 from completely filling up.

The cassette 3734 and/or the console 3732 may provide a fluid level indicator 3760 to monitor the level of aspirant (tissue and fluid) being accumulated in the first collection chamber 3740. The fluid level indicator 3760 may monitor one or more threshold levels and generate output signals to the console 3732 to initiate an appropriate response to the attainment of a particular threshold level. For instance, upon detecting one threshold level, the fluid level indicator 3760 may initiate a warning (audible, visual, etc.) to the user that the first collection chamber 3740 is approaching an overfill condition. Upon detecting a higher threshold level, the fluid level indicator 3760 may cause the vacuum regulator 3730 to switch from the first tissue collection state to the second tissue collection state, thereby opening the cassette valve 3744 and enabling aspirant to drain into the second collection chamber 3742. Upon detecting a yet higher threshold level, or detecting successive threshold levels at an undesirably short period of time (indicating that the first collection chamber 3740 is filling up too rapidly, the fluid level indicator 3760 may cause the vacuum regulator 3730 to divert application of vacuum away from the first and second vacuum ports 3748, 3750 and/or cause the vacuum source 3714 to be shut down. For such purposes, any suitable fluid level indicator may be provided. In the illustrated example, the fluid level indicator 3760 includes a floating ball 3762 that rises and falls with the level of aspirant in the first collection chamber 3740. The ball 3762 may be constrained to move substantially only in the direction of rising and falling aspirant by guide structures 3764 of the cassette housing 3738. One or more light sources 3766 (e.g., light emitting diodes, lasers, etc.) may be provided to direct one or more light beams through the first collection chamber 3740 to one or more light detectors 3768 (e.g., photodiodes, photomultiplier tubes, etc.). Each light beam may correspond to a threshold level to be detected. As the surface of the aspirant rises, the ball 3762 moves into the path of a light beam, thereby breaking the light beam whereby attainment of the corresponding threshold level is detected. In a typical implementation, the light source(s) 3766 and light detector (s) 3768 are mounted in the console 3732, and are positioned so as to direct the light beam(s) at the correct elevation(s) through the first collection chamber 3740 when the cassette 3734 is installed in the console 3732.

In some implementations, the cassette 3734 (i.e., the cassette housing 3738) includes a fluid-routing chamber 3772 that is fluidly isolated from the first collection chamber 3740 and second collection chamber 3742. The fluid-routing chamber 3772 may be utilized, for example, to provide a coupling with the aspiration line 3222 (or with both the aspiration line 3222 and the gas line 3224), whereby the vacuum source 3714 (or both the vacuum source 3714 and the pressurized gas source 3702) are operatively coupled with the tissue removal device 3100 simply by installing the cassette 3734 in the console 3732. The fluid-routing chamber 3772 may also be utilized to provide permanent fluid couplings that cannot be disassembled by the user, thereby rendering the tissue removal device 3100 and the cassette 3734 a permanently assembled single unit, which single unit may be disposable by the user and replaced with a new or sterilized unit.

In the implementation specifically illustrated in FIG. 37, the fluid-routing chamber 3772 includes a cassette inlet 3774 through which the aspiration line 3222 and gas line 3224 pass from outside the cassette 3734. In this example, the aspiration inlet 3746 to which the aspiration line 3222 is coupled is located in the fluid-routing chamber 3772. Also in this example, the fluid-routing chamber 3772 includes a gas port 3776 leading to the outside of the cassette 3734. The gas line 3224 passes through the fluid-routing chamber 3772 and is coupled to the gas port 3776. The gas port 3776 may be located on the same side of the cassette 3734 as the first vacuum port 3748 and second vacuum port 3750. The console 3732 may include complementary respective couplings, such that upon installation of the cassette 3734, the gas line 3224 is automatically placed in communication with the pressurized gas source 3702, and the first collection chamber 3740 and second collection chamber 3742 are automatically placed in communication with the vacuum source 3714. The cassette 3734, particularly the cassette inlet 3774, may be configured such that the user cannot decouple the aspiration line 3222 and gas line 3224 from the cassette 3734. Moreover, the cassette 3734 may be configured such that the user cannot disassemble the cassette housing 3738 or access the cassette interior via the cassette inlet 3774, gas port 3776, first vacuum port 3748 or second vacuum port 3750.

Figure 38:
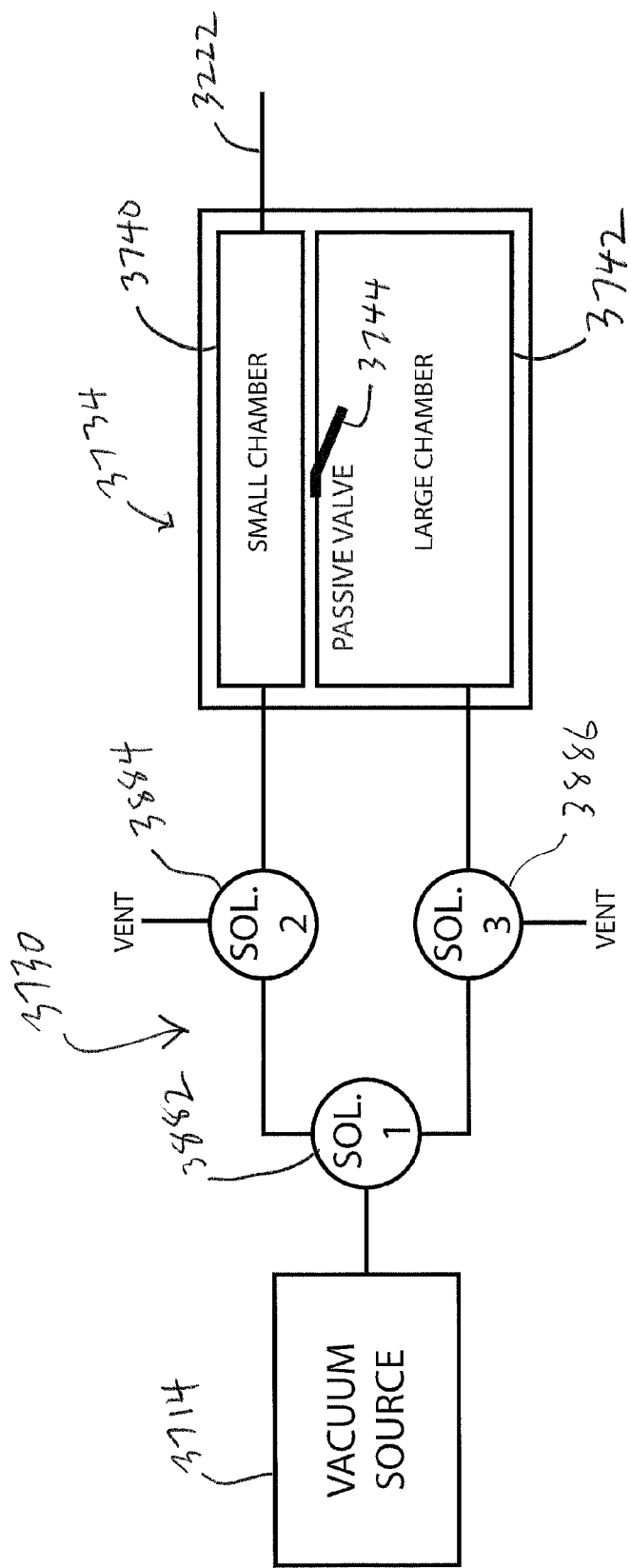
FIG. 38 is a schematic view of an example of a cassette, vacuum regulator and vacuum source that may be provided with the tissue removal system illustrated in FIG. 37.

FIG. 38 is a schematic view of an example of the cassette 3734, vacuum regulator 3730 and vacuum source 3714. In this implementation, the vacuum regulator 3730 includes a first valve 3882, a second valve 3884 and a third valve 3886. The first valve 3882 is in-line between the vacuum source 3714 and the second valve 3884 and third valve 3886, the second valve 3884 is in-line between the first valve 3882 and the first collection chamber 3740, and the third valve 3886 is in-line between the first valve 3882 and the second collection chamber 3742. The valves 3882, 3884, 3886 may be of any suitable design, typically an active design, such as solenoid valves. In one example of a valve configuration, the valves 3882, 3884, 3886 are each movable to three positions. The first valve 3882 is movable to a closed position, an open position allowing vacuum to the second valve 3884, and an open position allowing vacuum to the third valve 3886. The second valve 3884 is movable to a closed position, an open position allowing vacuum to the first collection chamber 3740, and an open position leading to a vent. The third valve 3886 is movable to a closed position, an open position allowing vacuum to the second collection chamber 3742, and an open position leading to a vent. Hence, for example, the first tissue collection state (in which only the first collection chamber 3740 is utilized) may be implemented by opening the first valve 3882 to the second valve 3884, opening the second valve 3884 to the first collection chamber 3740, and closing the third valve 3886. The second tissue collection state (in which both the first collection chamber 3740 and second collection chamber 3742 are utilized) may be implemented by opening the first valve 3882 to the third valve 3886, opening the third valve 3886 to the second collection chamber 3742, and opening the second valve 3884 to vent.

It will be understood that other configurations of the valves 3882, 3884, 3886 are possible. For example, the first valve 3882 may be configured to have a position at which vacuum is open to both the second valve 3884 and third valve 3886 simultaneously. In this case, the second valve 3884 and third valve 3886 may be configured to have variable valve positions that enable the respective vacuum levels applied to the first collection chamber 3740 and second collection chamber 3742 to be independently adjusted.

Figure 39:
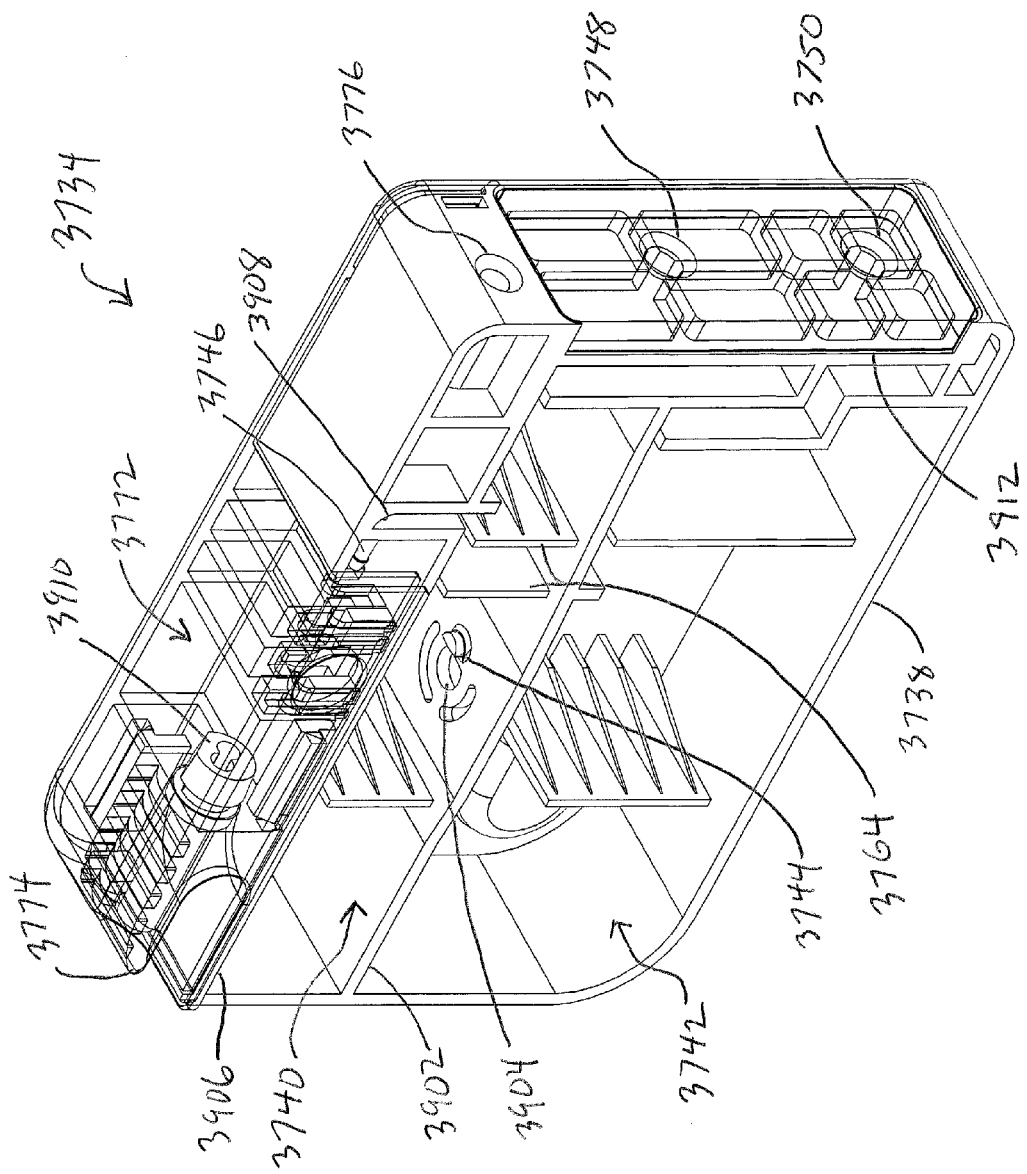
FIG. 39 is a partially cut-away perspective view of an example of a cassette that may be provided with the tissue removal system illustrated in FIG. 37.
Figure 40:
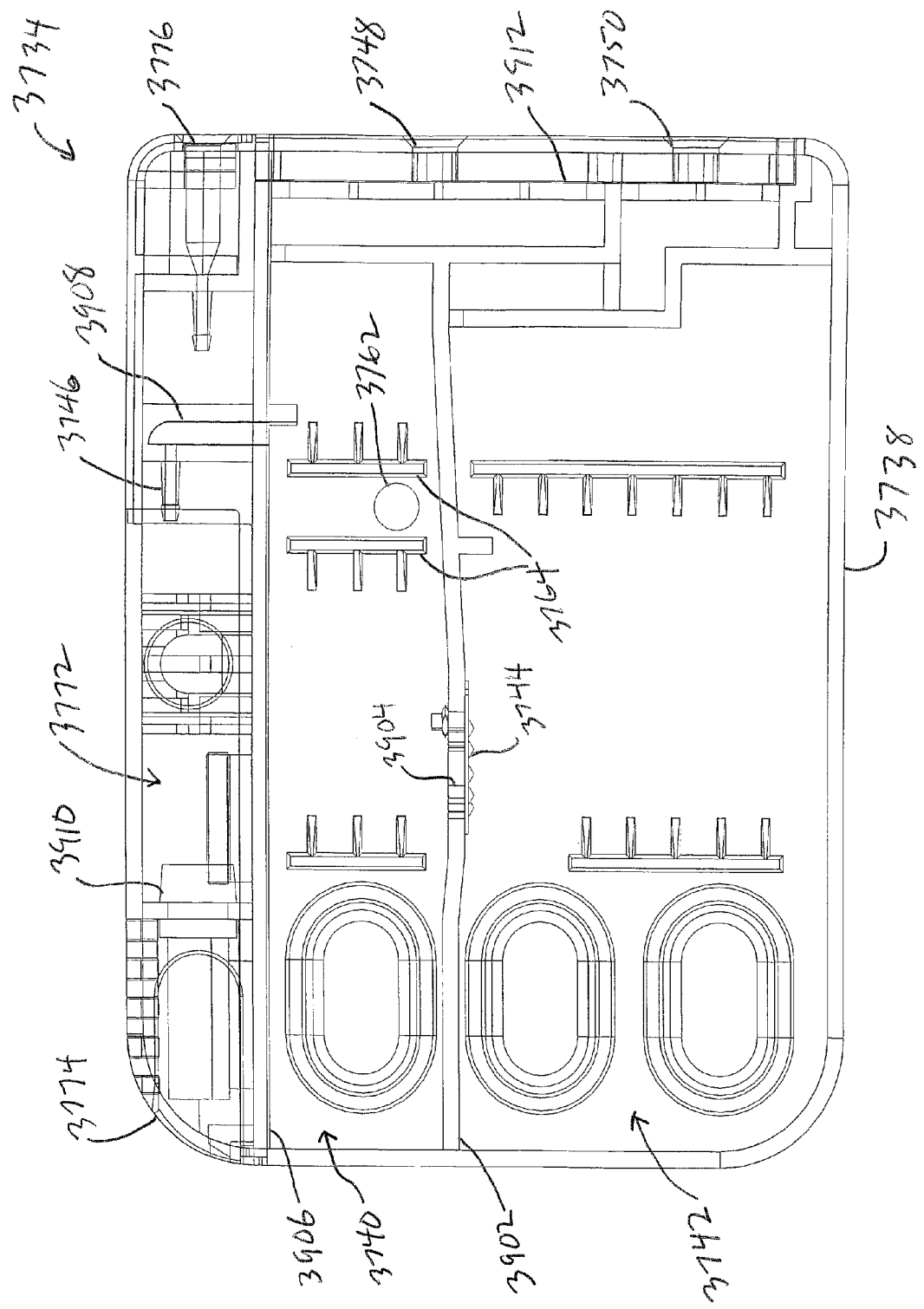
FIG. 40 is a partially cut-away side view of the cassette illustrated in FIG. 39.

FIGS. 39 and 40 are partially cut-away perspective and side views, respectively, of an example of the cassette 3734. The cassette housing 3738 includes an interior structure 3902 such as a wall that fluidly isolates the first collection chamber 3740 from the second collection chamber 3742. In this example, the cassette valve 3744 is a flapper valve that alternately opens and closes a bore 3904 formed through the interior structure 3902. The cassette housing 3738 also includes another interior structure 3906 such as a wall that fluidly isolates the fluid-routing chamber 3772 from the first collection chamber 3740. The aspiration inlet 3746 is mounted in communication with a fluid transfer passage 3908 that leads to the first collection chamber 3740. Inside the fluid-routing chamber 3772, the aspiration inlet 3746 and gas port 3776 are configured for coupling to tubing of the aspiration line 3222 and gas line 3224, respectively. The aspiration line 3222 and gas line 3224 pass through a feed-through member (or tube support member) 3910 that is securely mounted at the cassette inlet 3774. The feed-through member 3910 may serve as a strain relief for flexible tubing of the aspiration line 3222 and gas line 3224. In the illustrated example (similar to the feed-through member 3130 of the tissue removal device 3100 described above and illustrated in FIGS. 31 and 32), the feed-through member 3910 has a gap between two bores to accommodate a dual-lumen construction in which the aspiration line 3222 and gas line 3224 are integrally connected side-by-side. As described above, hydrophobic filters may be interposed between the first collection chamber 3740 and first vacuum port 3748 and between the second collection chamber 3742 and second vacuum port 3750. In the present implementation a single strip 3912 of hydrophobic filter material, mounted between the first vacuum port 3748 and second vacuum port 3750 on one side and the first collection chamber 3740 and second collection chamber 3742 on the other side, may be provided for this purpose.

FIGS. 41 and 42 are perspective and side views, respectively, of an example of a cylindrical cannula seal 4100. The cannula seal 4100 includes an open distal seal end 4102, an open proximal seal end 4104 of greater inside diameter than the distal seal end 4102, and a tapered section 4106 between the distal seal end 4102 and proximal seal end 4104 along which the inside diameter gradually increases. The cannula seal 4100 may be composed of a suitable resilient material such as, for example, silicone. A cannula, such as the aspiration cannula 3104 of the tissue removal device 3100, may be inserted through the cannula seal 4100 such that the cannula seal 4100 circumscribes at least a portion of the aspiration cannula 3104 that includes the distal tip 3106. In this manner, the cannula seal 4100 is compressed around the aspiration cannula 3104 in a fluid-sealing manner. When the aspiration cannula 3104 is inserted through an incision into a surgical site, such as an incision made in a patient's eye, the cannula seal 4100 provides a fluid-sealed interface between the aspiration cannula 3104 and the tissue defining the incision. Consequently, fluid (e.g., irrigation fluid) is prevented from escaping the surgical site through the incision. Another cannula seal 4100 may likewise be installed around the irrigation instrument 3706 (FIG. 37).

Figure 30:
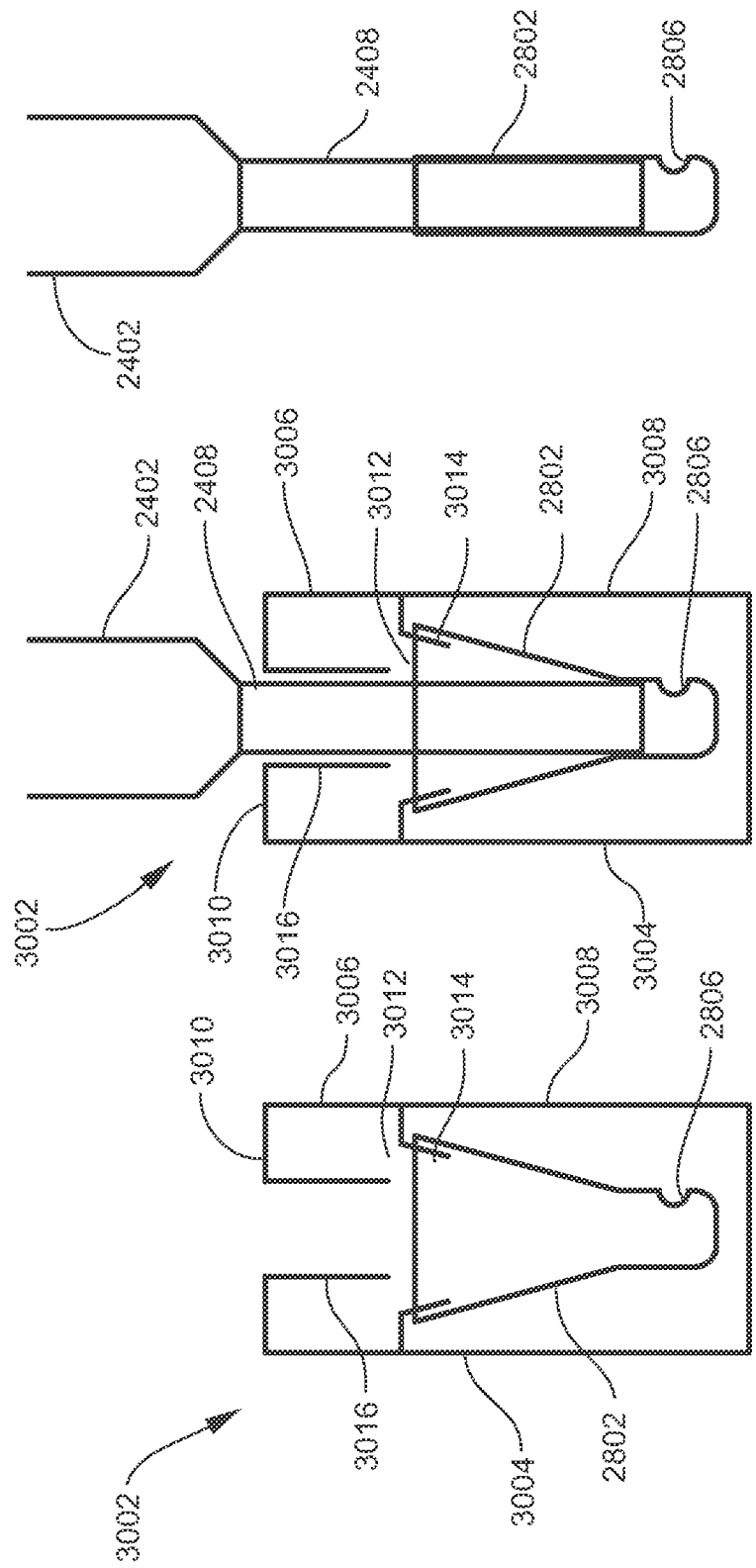
FIG. 30A is a cross-sectional view of a device for applying an I/A tip membrane to the distal end of a tissue removal device of the present invention.
FIG. 30B is a cross-sectional view of the device illustrated in FIG. 29A, showing the distal end of a tissue removal device inserted into the device.
FIG. 30C is a side view showing an I/A tip membrane applied to the distal end of a tissue removal device of the present invention.

FIGS. 43A, 43B and 43C illustrate the use of a device 4302 for applying a resilient membrane 2802 to the distal end of the aspiration cannula 3104. In some implementations, the device 4302 is a modification of the device 3002 described above and illustrated in FIGS. 30A, 30B and 30C, and accordingly like reference numerals designate like components. In the present implementation, the resilient membrane 2802 is pre-installed in the enclosure 3004 at the time the device 4302 and resilient membrane 2802 are provided to the user. The resilient membrane 2802 includes an open membrane end 4304, an opposing closed membrane end 4306, a membrane wall of nominally cylindrical cross-section between the open membrane end 4304 and closed membrane end 4306, and a membrane side port 2806 in the membrane wall proximal to the closed membrane end 4306. The resilient membrane 2802 may be composed of a suitable resilient sealing material such as, for example, silicone. In the pre-installed state, the open membrane end 4304 is held by the support member 3014 in a stretched position such that the open membrane end 4304 is of greater cross-sectional area than the closed membrane end 4306. The device 4302 additionally includes a rigid cannula extension 4312 that facilitates proper application of the resilient membrane 2802 to the aspiration cannula 3104. The cannula extension 4312 includes an open extension end 4314, an opposing closed extension end 4316, a cylindrical extension wall between the open extension end 4314 and the closed extension end 4316, and an extension side port 4320 in the extension wall. In the pre-installed state, the cannula extension 4312 is disposed in the resilient membrane 2802 such that the membrane side port 2806 is aligned with the extension side port 4320, the membrane wall is compressed around the extension wall, and the closed membrane end 4306 is compressed against the closed extension end 4316. Moreover, the open extension end 4314 is generally aligned with the canal 3016 along the canal axis. The resilient membrane 2802 is applied to the aspiration cannula 3104 by inserting the aspiration cannula 3104 through the canal 3016 and into contact with the open extension end 4314, as shown in FIG. 43B. Upon further insertion, the resilient membrane 2802 is displaced from the support member 3014 and compressively seals against the aspiration cannula 3104, as shown in FIG. 43C. The resilient membrane 2802 also secures the cannula extension 4312 to the distal end of the aspiration cannula 3104.

After application of the resilient membrane 2802 to the aspiration cannula 3104, the aspiration cannula 3104 may be utilized in a procedure such as, for example, that described above and illustrated in FIG. 29.

In some implementations, the support member 3014 includes two or more fingers that are movable (e.g., pivotable) for varying the cross-sectional area of the open membrane end 4304. The fingers may be mechanically linked to adjustment members 4326 (e.g., levers, buttons, etc.) disposed outside of the enclosure 3004, which may be manipulated by the user to adjust the resilient membrane 2802 as needed to facilitate proper insertion of the aspiration cannula 3104 into the resilient membrane 2802.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

Further, terms such as "coupled to," and "configured for coupling to" and "secured to" (for example, a first component is "coupled to" or "is configured for coupling to" or is "secured to" a second component) are used herein to indicate a structural, functional, mechanical, electrical, signal, optical, magnetic, electromagnetic, ionic or fluidic relationship between two or more components or elements. As such, the fact that one component is said to be coupled with a second component is not intended to exclude the possibility that additional components may be present between, and/or operatively associated or engaged with, the first and second components.

Although the previous description only illustrates particular examples of various implementations, the invention is not limited to the foregoing illustrative examples. A person skilled in the art is aware that the invention as defined by the appended claims can be applied in various further implementations and modifications. In particular, a combination of the various features of the described implementations is possible, as far as these features are not in contradiction with each other. Accordingly, the foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A tissue removal device, comprising:
    a housing;
    a rigid aspiration cannula extending from the housing to a distal tip outside the housing;
    a valve disposed in the housing and configured for communicating with a vacuum source, the valve comprising a valve port communicating with the aspiration cannula in a fluid-sealed manner, wherein an inside diameter of the valve port is equal to or greater than an inside diameter of the distal tip; and
    a pneumatically-driven actuator configured for moving the valve between an open position and a closed position, wherein:
    at the open position, the valve port is open wherein the valve defines an aspiration path through the aspiration cannula and the valve;
    at the closed position, the valve port is closed wherein the valve prevents vacuum from being applied at the distal tip;
    the valve comprises an inner cannula and an outer cannula coaxially disposed about at least a portion of the inner cannula;
    the inner cannula is configured for communicating with the vacuum source and is linearly movable by the actuator between the open position and the closed position;
    the valve port is formed in the outer cannula;
    at the open position the aspiration path passes through the outer cannula via the valve port and into the inner cannula; and
    at the closed position the inner cannula blocks the valve port.

2. The tissue removal device of claim 1, comprising a transition adjoining the outer cannula at the valve port in a fluid-sealed manner, wherein the aspiration cannula extends along a first cannula axis from the transition to the distal tip, and the inner cannula extends along a second cannula axis offset from the first cannula axis.

3. The tissue removal device of claim 2, wherein the valve port is oriented at ninety degrees relative to the second cannula axis, and the transition turns at an angle of less than 90 degrees relative to the first cannula axis.

4. The tissue removal device of claim 1, wherein the outer cannula comprises a distal outer cannula end and a resilient seal closing the distal outer cannula end in a fluid-sealed manner, and at the closed position the inner cannula contacts the resilient seal in a fluid-sealed manner.

5. The tissue removal device of claim 1, wherein the inside diameter of the valve port ranges from 0.05 mm to 5 mm, and the inside diameter of the distal tip ranges from 0.2 mm to 2 mm.

6. The tissue removal device of claim 1, comprising a gas conduit and a diaphragm, wherein the housing comprises a chamber wall, the diaphragm and the chamber wall cooperatively define a gas chamber with which the gas conduit communicates, the diaphragm is expandable in response to gas flowing from the gas conduit into the gas chamber, and the actuator is reciprocable in response to alternating expansion and contraction of the diaphragm.

7. The tissue removal device of claim 6, wherein the diaphragm comprises a diaphragm opening and the gas conduit passes through the diaphragm opening in a fluid-sealed manner.

8. The tissue removal device of claim 6, wherein the diaphragm comprises a first diaphragm opening and a second diaphragm opening, the gas conduit passes through the first diaphragm opening in a fluid-sealed manner, and the inner cannula passes through the second diaphragm opening and the gas chamber in a fluid-sealed manner.

9. The tissue removal device of claim 6, wherein the actuator comprises a piston mechanically communicating with the inner cannula and positioned to contact the diaphragm.

10. The tissue removal device of claim 9, wherein the piston mechanically communicates with the gas conduit, and the inner cannula and the gas conduit are linearly movable together with the piston.

11. The tissue removal device of claim 9, comprising a spring positioned to impart a biasing force against movement of the piston in a direction toward the open position, wherein the inner cannula is biased toward the closed position.

12. The tissue removal device of claim 9, wherein the piston comprises a piston head positioned to contact the diaphragm, and a sleeve surrounding the inner conduit.

13. The tissue removal device of claim 1, wherein the actuator is configured for communicating with a valve control device such that the inner cannula is reciprocable between the open position and the closed position to induce vacuum pulses in the aspiration cannula at a controllable pulse rate.

14. The tissue removal device of claim 1, comprising a cylindrical cannula seal composed of a resilient material, the cylindrical cannula seal circumscribing at least a portion of the aspiration cannula in fluid-sealing contact therewith, the cylindrical cannula seal comprising a distal seal end, a proximal seal end of greater inside diameter than the distal seal end, and a tapered section between the distal seal end and the proximal seal end.

15. The tissue removal device of claim 1, comprising a spring positioned to impart a biasing force against movement of the actuator in a direction toward the open position, wherein the valve is biased toward the closed position.

16. The tissue removal device of claim 1, comprising a gas conduit disposed in the housing and communicating with the actuator, the gas conduit configured for communicating with a pressurized gas source.

17. The tissue removal device of claim 16, comprising a diaphragm, wherein the housing comprises a chamber wall, the diaphragm and the chamber wall cooperatively define a gas chamber with which the gas conduit communicates, the diaphragm is expandable in response to gas flowing from the gas conduit into the gas chamber, and the valve is reciprocable in response to alternating expansion and contraction of the diaphragm.

18. The tissue removal device of claim 1, wherein the actuator comprises a piston communicating with the valve.

19. The tissue removal device of claim 18, comprising a gas conduit disposed in the housing and communicating with the piston, the gas conduit configured for communicating with a pressurized gas source, wherein the valve and the gas conduit are movable together with the piston.

20. The tissue removal device of claim 1, wherein at least a portion of the aspiration cannula is tapered such that an inside diameter of the distal tip is smaller than an inside diameter of a proximal end of the aspiration cannula.

21. The tissue removal device of claim 1, wherein the actuator is configured for communicating with a valve control device such that the valve is movable between the open position and the closed position to induce vacuum pulses in the aspiration cannula at a controllable pulse rate.

22. A tissue removal system, comprising:
a tissue removal device comprising:
a housing;
a rigid aspiration cannula extending from the housing to a distal tip outside the housing;
a valve disposed in the housing and configured for communicating with a vacuum source, the valve comprising a valve port communicating with the aspiration cannula in a fluid-sealed manner, wherein an inside diameter of the valve port is equal to or greater than an inside diameter of the distal tip; and
a pneumatically-driven actuator configured for moving the valve between an open position and a closed position, wherein:
at the open position, the valve port is open wherein the valve defines an aspiration path through the aspiration cannula and the valve; and
at the closed position, the valve port is closed wherein the valve prevents vacuum from being applied at the distal tip;
an aspiration line communicating with the valve and passing through the housing of the tissue removal device; and
a cassette comprising a cassette interior, an aspiration inlet communicating with the aspiration line and the cassette interior, and a vacuum outlet communicating with the cassette interior and configured for communication with the vacuum source, wherein the cassette is configured for being operated in an installed position at which the cassette is removably inserted into a console, and at the installed position the vacuum outlet communicates with the vacuum source,
wherein the aspiration path runs from the inner cannula, through the aspiration line and into the cassette interior.

23. The tissue removal system of claim 22, wherein:
the cassette comprises a fluid-routing chamber, a collection chamber communicating with the vacuum outlet, an interior structure fluidly isolating the fluid-routing chamber from the collection chamber, and a cassette inlet leading from outside the cassette into the fluid-routing chamber;
the interior structure comprises a transfer passage between the fluid-routing chamber and the collection chamber;
the aspiration inlet communicates with the transfer passage; and
the aspiration line passes through the cassette inlet and into communication with the aspiration inlet, wherein the aspiration path runs through the transfer passage and into the collection chamber.

24. The tissue removal system of claim 23, wherein the aspiration inlet is disposed in the fluid-routing chamber, and the cassette is configured such that the fluid-routing chamber and the aspiration inlet are inaccessible by a user, and such that the tissue removal device and the cassette comprise a permanently assembled single unit.

25. The tissue removal system of claim 23, comprising a gas conduit disposed in the housing of the tissue removal device and communicating with the actuator, the gas conduit configured for communicating with a pressurized gas source, wherein the cassette comprises a gas port leading from outside the cassette into the fluid-routing chamber, the gas conduit passes through the housing of the tissue removal device, through the cassette inlet and into communication with the gas port, and at the installed position the gas port communicates with the pressurized gas source.

26. The tissue removal system of claim 22, wherein the cassette comprises a hydrophobic filter disposed in the cassette interior and configured for preventing liquid in the cassette interior from passing through the vacuum outlet.

27. The tissue removal system of claim 22, wherein:
the cassette comprises a first collection chamber communicating with the aspiration inlet, a second collection chamber of larger volume than the first collection chamber, an interior structure separating the first collection chamber from the second collection chamber and comprising a bore leading from the first collection chamber to the second collection chamber;
the cassette comprises a cassette valve alternately opening and closing the bore and configured to be closed when pressure in the first collection chamber is lower than pressure in the second collection chamber; and
the vacuum outlet comprises a first vacuum port communicating with the first collection chamber and a second vacuum port communicating with the second collection chamber.

28. The tissue removal system of claim 27, wherein the cassette comprises a fluid level indicator configured for indicating a level of fluid in the first collection chamber.

29. The tissue removal system of claim 28, wherein the fluid level indicator is configured for generating an output signal in response to fluid reaching a threshold level in the first collection chamber, and the console is configured for adjusting vacuum applied to the cassette based on the output signal.

30. The tissue removal system of claim 28, wherein the console is configured for adjusting by applying a vacuum to the second collection chamber sufficient to open the cassette valve, or ceasing application of vacuum to the cassette.

31. The tissue removal system of claim 27, comprising a vacuum regulator communicating with the vacuum source and configured for controlling vacuum levels respectively applied to the first vacuum port and the second vacuum port.

32. The tissue removal system of claim 22, comprising the console, wherein the vacuum source is located in the console, and the console comprises:
a receptacle for removably receiving the cassette at the installed position;
a vacuum coupling configured for detachably coupling with the vacuum outlet at the installed position; and
a valve control device configured for communicating with the actuator at the installed position to control movement of the valve of the tissue removal device between the open position and the closed position to induce vacuum pulses in the aspiration cannula at a controllable pulse rate.

33. The tissue removal system of claim 32, comprising a gas conduit disposed in the housing of the tissue removal device and communicating with the actuator, wherein:
the cassette comprises a collection chamber communicating with the aspiration inlet and the vacuum outlet, a fluid-routing chamber fluidly isolated from the collection chamber, a cassette inlet leading from outside the cassette into the fluid-routing chamber, and a gas port leading from outside the cassette into the fluid-routing chamber;
the console comprises a pressurized gas source communicating with the valve control device, and a gas coupling configured for detachably coupling with the gas port at the installed position; and
the gas conduit passes through the housing of the tissue removal device, through the cassette inlet and into communication with the gas port, wherein at the installed position the gas conduit communicates with the valve control device.

34. The tissue removal system of claim 22, wherein the aspiration line is permanently installed in the housing of the tissue removal device and in the cassette, the tissue removal device is configured such that an interior thereof is inaccessible by a user, and the cassette is configured such that the cassette interior is inaccessible by the user, and such that the tissue removal device and the cassette comprise a permanently assembled single unit.

* * * * *